(12) United States Patent
Lange et al.

(10) Patent No.: US 7,928,134 B2
(45) Date of Patent: Apr. 19, 2011

(54) 5-ARYL-4,5-DIHYDRO-(1H)-PYRAZOLINES AS CANNABINOID CB1 RECEPTOR AGONISTS

(75) Inventors: Josephus H. M. Lange, Weesp (NL); Hicham Zilaout, Weesp (NL); Bernard J. Van Vliet, Weesp (NL)

(73) Assignee: Solvay Pharmaceuticals B.V., Weesp (NL)

( * ) Notice: Subject to any disclaimer, the term of this patent is extended or adjusted under 35 U.S.C. 154(b) by 57 days.

(21) Appl. No.: 12/234,080

(22) Filed: Sep. 19, 2008

(65) Prior Publication Data

US 2009/0082396 A1   Mar. 26, 2009

Related U.S. Application Data

(60) Provisional application No. 60/973,863, filed on Sep. 20, 2007.

(51) Int. Cl.
*A01N 43/56* (2006.01)
*A61K 31/415* (2006.01)
*C07D 231/06* (2006.01)
*C07C 233/00* (2006.01)
*C07C 235/00* (2006.01)
*C07C 237/00* (2006.01)
*C07C 239/00* (2006.01)

(52) U.S. Cl. ............ 514/403; 514/406; 548/379.4; 564/200; 564/204; 564/207

(58) Field of Classification Search .......... 548/379.4; 514/403, 406; 564/199, 200, 204, 207
See application file for complete search history.

(56) References Cited

FOREIGN PATENT DOCUMENTS

| WO | WO 98/05046 | * | 7/1988 |
|---|---|---|---|
| WO | WO 97/21682 | | 6/1997 |
| WO | WO 01/29007 A1 | | 4/2001 |
| WO | WO 03/020217 A2 | | 3/2003 |
| WO | WO 2004/099157 A1 | | 11/2004 |
| WO | WO 2005/074920 A1 | | 8/2005 |
| WO | WO 2005/077911 A1 | | 8/2005 |
| WO | WO 2007/009689 A | | 1/2007 |

OTHER PUBLICATIONS

Kushner et. al., Canadian Journal of Physiology and Pharmacology, 1999, NRC Canada, vol. 77, issue 2, pp. 79-88.*
Bach et. al., Tetrahedron, 1994, Pergamon, vol. 50, No. 25, pp. 7543-7556.*
Shim, et al., "Molecular Interaction of the Antagonist N-(Piperidin-1-yl)-5-(4-chlorophyenyl)-1-(2,4-dichlorophenyl)-4-mthyl-1H-pyrazole-3-carboxamide with the CB1 Cannabinoid Receptor," *J. Med Chem* 2002, 45, 1447-1459.
Thomas, et al., "Synthesis of long-chain amide analogs of the cannabinoid $CB_1$ receptor antagonist N-(piperidinyl)-5-(4-chlorophyenyl)-1-(2,4-dichlorophyenyl)-4-methyl-1 H-pyrazole-3-carboxamide (SR141716) with unique binding selectivities and pharmacological activities," *Bioorg. Med. Chem* 13 (2005) 5463-5474.
Li, et al., "Candidate PET radiologands for cannabinoid $CB_1$ Receptors: [$^{18}$f]AM5144 and related pyrazole compounds," *Nuclear Medicine and Biology* 32 (2005) 361-366.
PCT International Search Report dated Jun. 16, 2009, International Application No. PCT/EP2008/062283.
Written Opinion of the International Searching Authority, dated Jun. 16, 2009, International Application No. PCT/EP2008/062283.

* cited by examiner

*Primary Examiner* — Sreeni Padmanabhan
*Assistant Examiner* — Sarah Pihonak
(74) *Attorney, Agent, or Firm* — Finnegan, Henderson, Farabow, Garrett & Dunner, L.L.P.

(57) ABSTRACT

The invention is directed to 5-(hetero)aryl-4,5-dihydro-(1H)-pyrazole (pyrazoline) derivatives as cannabinoid $CB_1$ receptor agonists, to pharmaceutical compositions comprising these compounds, to methods for their syntheses, methods for preparing novel intermediates useful for their syntheses, and methods for preparing compositions. The invention also relates to the uses of such compounds and compositions, administered to patients to achieve a therapeutic effect in disorders in which $CB_1$ receptors are involved, or that can be treated via manipulation of those receptors.

Compounds of the present invention include compounds of formula (I):

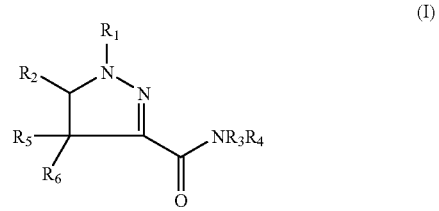

wherein the substituents have the definitions given in the specification.

11 Claims, No Drawings

5-ARYL-4,5-DIHYDRO-(1H)-PYRAZOLINES AS CANNABINOID CB1 RECEPTOR AGONISTS

This application claims the benefit of U.S. provisional application No. 60/973,863, filed Sep. 20, 2007, the disclosure of which is incoporated herein by reference.

The present disclosure relates to the fields of pharmaceutical and organic chemistry, and provides 5-(hetero)aryl-4,5-dihydro-(1H)-pyrazole (pyrazoline) derivatives, intermediates for synthesizing these compounds, formulations comprising these compounds, and methods of treatment using these compounds.

The endogenous cannabinoid receptor agonist, anandamide, is too unstable to be of practical value as a drug. The same is true for other endocannabinoids such as 2-arachidonoyl-glycerol and noladin ether. With the exception of $\Delta^9$-tetrahydrocannabinol ($\Delta^9$-THC, dronabinol, Marinol®) and Nabilone (Cesamet®) no other cannabinoid receptor agonists have been registered as drugs. In addition, Sativex® (an extract from the *Cannabis sativa* L. plant) has been recently approved as a prescription medicine (Barnes, 2006). Compounds like CP 55,940 and WIN 55,212-2 are not registered drugs, but have been, and still are, used as pharmacological tools.

It has been postulated that cannabinoid $CB_1$ receptors can occur in two different states: the active 'R*-state' to which agonists bind, and the inactive 'R-state' to which antagonists or inverse agonists—such as rimonabant—bind. Both states have considerably different three-dimensional geometries. Key interaction in the cannabinoid-$CB_1$ receptor model (based on Palczewski's X-ray structure of bovine rhodopsin) is a hydrogen bond between the carbonyl group of, e.g., the $CB_1$ receptor inverse agonist rimonabant, and the LYS192 residue of the $CB_1$ receptor. This hydrogen bond has a stabilizing effect on the Lys192-Asp366 salt bridge of the intracellular end of the transmembrane helices 3 and 6. The existence of this specific salt bridge is induced by a pronounced kink at Pro 358 in transmembrane helix 6, present in the inactive R-state of the receptor, but not in the active R*-state, which is stabilized by $CB_1$ receptor agonist binding (Hurst, 2002; Shim, 2002; Reggio, 2003; Pertwee, 2005 and Lange, 2005). Thus, it is not possible to apply structural features of known $CB_1$ receptor antagonists or inverse agonists to design novel $CB_1$ receptor agonists in a straightforward manner.

Ample evidence exists that cannabinoid receptor agonists have therapeutic possibilities as appetite stimulants, entiemetics, analgesics, anti-glaucoma agents (Croxford, 2003; Drysdale, 2003), tumor growth inhibitors (Ligresti, 2003), and agents for the treatment of neurodegenerative disorders, including multiple sclerosis and Alzheimer's disease (Smith, 2004; Croxford, 2004).

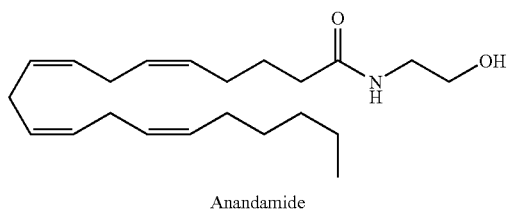

Anandamide

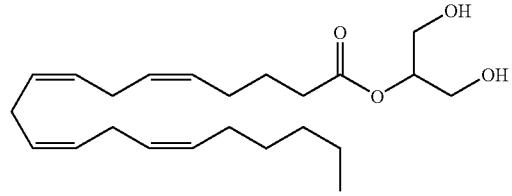

2-Arachidonoyl-glycerol (2-AG)

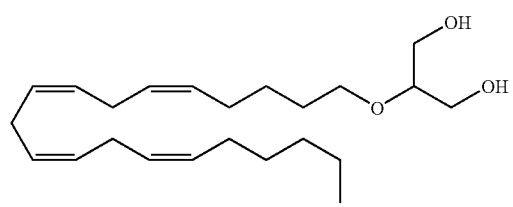

Noladin ether

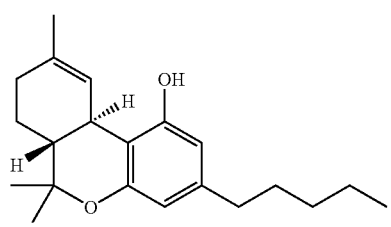

$\Delta^9$-THC (dronabinol)

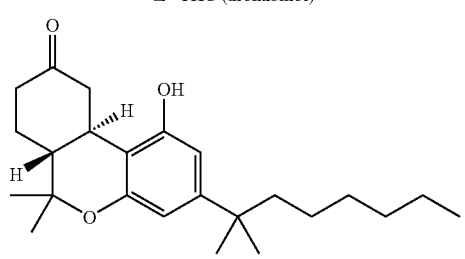

Nabilone

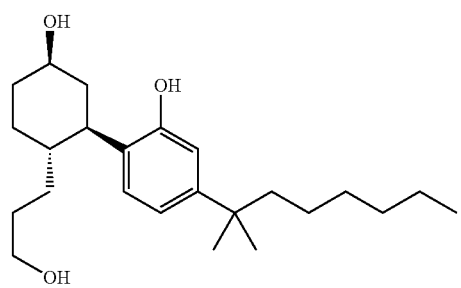

CP 55,940

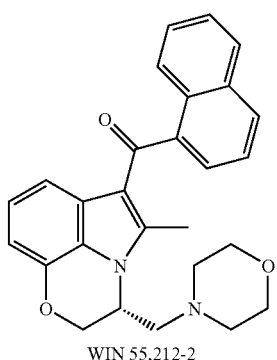

WIN 55,212-2

Thus, there is a need to develop novel compounds with $CB_1$ receptor agonistic activity, structurally unrelated to known cannabinoid receptor agonists.

DISCLOSURE

Surprisingly, the inventors found that replacing the 1-aryl or 1-heteroaryl group in 4,5-dihydro-pyrazole $CB_1$ receptor antagonists described in WO 2005/074920, WO 2005/077911 or WO 2007/009689 by an optionally substituted alkyl moiety, resulted in novel compounds with a high affinity for $CB_1$ receptors, wherein these compounds may act as full or partial agonists at $CB_1$ receptors. Moreover, most of these compounds also showed affinity for $CB_2$ receptors.

In one embodiment, the invention relates to compounds of formula (I):

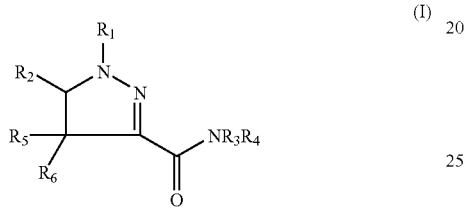

(I)

or tautomers, stereoisomers, N-oxides, isotopically-labelled analogues, or pharmaceutically acceptable salts of any of the foregoing,
wherein:
$R_1$ is chosen from:
  $C_{3-10}$ linear alkyl, $C_{4-10}$ branched alkyl, $C_{4-10}$ alkenyl, $C_{4-10}$ alkynyl, $C_{3-10}$-heteroalkyl, $C_{5-8}$-cycloalkyl-$C_{1-5}$-alky, and $C_{5-8}$-heterocycloalkyl-$C_{1-5}$-alkyl, each of which may be optionally substituted with 1-5 substituents, wherein the substituents are the same or different, and are chosen from methyl, ethyl, hydroxy, amino, cyano and fluoro,
  aryl-$C_{1-3}$-alkyl, heteroaryl-$C_{1-3}$-alkyl, aryl-$C_{1-3}$-heteroalkyl, and heteroaryl-$C_{1-3}$-heteroalkyl, wherein the aryl and heteroaryl groups are optionally substituted with 1-5 substituents Y, wherein each Y is the same or different, and is chosen from $C_{1-3}$-alkyl, $C_{1-3}$-alkoxy, hydroxy, halogen, trifluoromethyl, trifluoromethylthio, trifluoromethoxy, nitro, amino, mono- or dialkyl($C_{1-2}$)-amino, mono- or dialkyl($C_{1-2}$)-amido, ($C_{1-3}$)-alkyl sulfonyl, dimethylsulfamido, $C_{1-3}$-alkoxycarbonyl, carboxyl, trifluoromethylsulfonyl, cyano, carbamoyl, sulfamoyl, phenyl and acetyl, and
  2-cyano-ethyl;
$R_2$ is chosen from aryl and heteroaryl, each of which may be optionally substituted with 1-5 substituents Y as defined above;
$R_3$ is chosen from:
  linear and branched $C_{3-10}$ alkyl, $C_{3-8}$ cycloalkyl, $C_{5-10}$ bicycloalkyl, $C_{6-10}$ tricycloalkyl and $C_{8-11}$ tetracycloalkyl, each of which may be optionally substituted with 1-5 substituents, wherein the substituents are the same or different, and are chosen from methyl, ethyl, hydroxy, amino, and fluoro,
  $C_{3-8}$ cycloalkyl substituted with aryl and heteroaryl, wherein the aryl and heteroaryl are optionally substituted with 1-5 substituents Y as defined above,
  2,2,2-trifluoroethyl and 2-fluoroethyl,
  $C_{5-8}$ heterocycloalkyl, $C_{6-10}$ bicycloheteroalkyl, and $C_{7-10}$ tricycloheteroalkyl, each of which may be optionally substituted with 1-5 substituents, wherein the substituents are the same or different, and are chosen from methyl, ethyl, hydroxy, amino and fluoro,
  $C_{3-8}$ cycloalkyl-$C_{1-3}$-alkyl, $C_{5-10}$-bicycloalkyl-$C_{1-3}$-alkyl, and $C_{6-10}$-tricycloalkyl-$C_{1-3}$-alkyl, each of which may be optionally substituted with 1-5 substituents, wherein the substituents are the same or different, and are chosen from methyl, ethyl, hydroxy, amino and fluoro,
  branched and linear $C_{3-8}$ heterocycloalkyl-$C_{1-3}$-alkyl, $C_{5-10}$ bicycloheteroalkyl-$C_{1-3}$-alkyl, and $C_{6-10}$ tricycloheteroalkyl-$C_{1-3}$-alkyl, each of which may be optionally substituted with 1-5 substituents, wherein the substituents are the same or different, and are chosen from methyl, ethyl, hydroxy, amino and fluoro,
  aryl and heteroaryl, each of which may be optionally substituted with 1-5 substituents Y as defined above,
  aryl-$C_{1-5}$-alkyl, heteroaryl-$C_{1-5}$-alkyl, and diaryl-$C_{1-5}$-alkyl, wherein the aryl and heteroaryl groups are optionally substituted with 1-5 substituents Y as defined above,
  linear and branched $C_{4-8}$ alkenyl and $C_{4-8}$ alkynyl, each of which may be optionally substituted with 1-3 fluorine atoms, and
  branched and linear $C_{2-10}$ heteroalkyl, comprising 1-2 heteroatoms chosen from N, O, or S;
$R_4$ is chosen from hydrogen and $C_{1-4}$ alkyl;
$R_5$ is chosen from hydrogen and $C_{1-2}$ alkyl, optionally substituted with 1-3 fluorine atoms; and
$R_6$ is chosen from hydrogen and $C_{1-2}$ alkyl, optionally substituted with 1-3 fluorine atoms.

In another embodiment, the invention relates to compounds of formula (I):

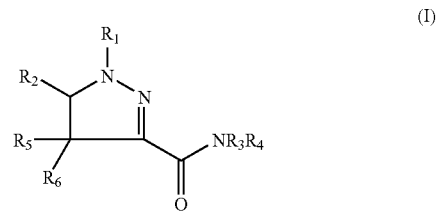

(I)

or tautomers, stereoisomers, N-oxides, isotopically-labelled analogues, or pharmaceutically acceptable salts of any of the foregoing,
wherein:
$R_1$ is chosen from:
  $C_{3-10}$ linear alkyl, $C_{4-10}$ branched alkyl, and $C_{5-8}$-cycloalkyl-$C_{1-5}$-alkyl, each of which may be optionally substituted with 1-3 substituents, wherein the substituents are the same or different, and are chosen from methyl, ethyl, cyano, and fluoro,
  aryl-$C_{1-3}$-alkyl, wherein the aryl group is optionally substituted with 1-3 substituents Y, wherein each Y is the same or different, and is chosen from $C_{1-3}$-alkyl, $C_{1-3}$-alkoxy, halogen, trifluoromethyl, trifluoro-methoxy, nitro, cyano, and phenyl, and
  2-cyano-ethyl;
$R_2$ is chosen from phenyl, thienyl, benzothienyl, and pyridyl, each of which may be optionally substituted with 1 or 2 substituents, wherein the substituents are the same or different, and are chosen from halogen, methyl, $CF_3$, $OCH_3$, and $OCF_3$;

$R_3$ is chosen from:
- linear and branched $C_{3-10}$ alkyl, $C_{3-8}$ cycloalkyl, $C_{5-10}$ bicycloalkyl, and $C_{6-10}$ tricycloalkyl, each of which may be optionally substituted with 1-3 substituents, wherein the substituents are the same or different, and are chosen from methyl, ethyl, hydroxy, amino, fluoro and aryl,
- $C_{5-8}$ heterocycloalkyl optionally substituted with 1-5 substituents, wherein the substituents are the same or different, and are chosen from methyl, ethyl, and fluoro,
- $C_{3-8}$ cycloalkyl-$C_{1-3}$-alkyl, $C_{5-10}$-bicycloalkyl-$C_{1-3}$-alkyl, and $C_{6-10}$-tricycloalkyl-$C_{1-3}$-alkyl, each of which may be optionally substituted with 1-5 substituents, wherein the substituents are the same or different, and are chosen from methyl, ethyl, and fluoro,
- aryl and heteroaryl, each of which may be optionally substituted with 1-5 substituents Y, wherein each Y is the same or different, and is chosen from $C_{1-3}$-alkyl, $C_{1-3}$-alkoxy, halogen, trifluoromethyl, trifluoromethylthio, trifluoromethoxy, nitro, cyano, and phenyl,
- aryl-$C_{1-5}$-alkyl, heteroaryl-$C_{1-5}$-alkyl, and diaryl-$C_{1-5}$-alkyl, wherein the aryl and heteroaryl groups are optionally substituted with 1-5 substituents, wherein the substituents are the same or different, and are chosen from $C_{1-3}$-alkyl, $C_{1-3}$-alkoxy, halogen, trifluoromethyl, trifluoromethylthio, trifluoromethoxy, nitro, cyano, and phenyl,
- branched and linear $C_{2-10}$ heteroalkyl, comprising 1-2 heteroatoms chosen from N, O, and S; and $R_4$, $R_5$, and $R_6$ are as defined above.

In another embodiment, the invention relates to compounds of formula (I):

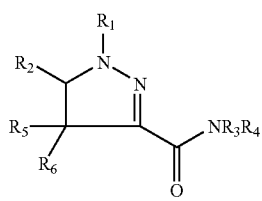

or tautomers, stereoisomers, N-oxides, isotopically-labelled analogues, or pharmaceutically acceptable salts of any of the foregoing,
wherein:
$R_1$ is chosen from:
- $C_{3-8}$ linear alkyl, $C_{4-8}$ branched alkyl, and $C_{5-6}$-cycloalkyl-$C_{1-5}$-alkyl, each of which may be optionally substituted with 1-3 substituents, wherein the substituents are the same or different, and are chosen from cyano and fluoro,
- aryl-$C_{1-3}$-alkyl and 2-cyano-ethyl;

$R_2$ is chosen from phenyl, thienyl, benzothienyl, and pyridyl, each of which may be optionally substituted with halogen, methyl, $CF_3$, $OCH_3$, and $OCF_3$; and $R_3$, $R_4$, $R_5$, and $R_6$ are as defined above.

In another embodiment, the invention relates to compounds of formula (I):

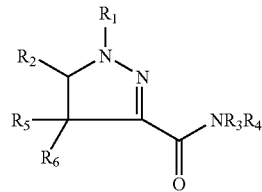

or tautomers, stereoisomers, N-oxides, isotopically-labelled analogues, or pharmaceutically acceptable salts of any of the foregoing,
wherein:
$R_1$ is chosen from 2-cyano-ethyl, n-propyl, n-butyl, 4,4,4-trifluorobutyl, isobutyl, n-pentyl, cyclohexylmethyl, and phenethyl;

$R_2$ is chosen from 2-fluorophenyl, 3-(trifluoromethyl)phenyl, 3-chlorophenyl, 3-fluorophenyl, 3-methoxyphenyl, 4-chlorophenyl, 4-fluorophenyl, benzothien-3-yl, pyrid-2-yl, thien-3-yl, and phenyl;

$R_3$ is chosen from 3-(trifluoromethyl)benzyl, 3-(trifluoromethyl)benzyl, 1-(4-fluorophenyl)-1-methyl-ethyl, 1-phenyl-1-methyl-ethyl, 1-phenyl-ethyl, 2-indanyl, 2-(4-fluorophenyl)-1,1-dimethyl-ethyl, 2-(trifluoromethyl)benzyl, 2,2-dimethylpropyl, 2,2-diphenylethyl, 2,2-diphenylpropyl, 2-methoxybenzyl, 2-phenyl-propyl, 2-phenyl-trans-cyclopropyl, 2-trifluoromethyl)phenyl, 3,4,5-trimethoxybenzyl, 3,4-dimethoxybenzyl, 3-fluorobenzyl, 3-methoxybenzyl, 4-chlorobenzyl, 4-methoxybenzyl, 5-methyl-thiazol-2-yl, adamant-1-yl, adamant-2-yl, adamantylmethyl, benzyl, cycloheptyl, cyclohexylmethyl, cyclooctyl, endo-bicyclo[2.2.1]hept-2-yl, exo-bicyclo[2.2.1]hept-2-yl, indan-2-yl, N,2,2,6,6-pentamethylpiperidin-4-yl, naphth-1-yl, naphthalen-1-yl-methyl, noradamant-1-yl, pyridin-3-ylmethyl, quinolin-3-yl, tert-butyl, (1-ethyl)propyl, (1R,2S,5R)-rel-6,6-dimethylbicyclo[3.1.1.]heptan-2-methyl, (3-dimethylamino)-2,2-dimethylpropyl, (furan-2-yl)methyl, (pyridin-3-yl)-methyl, 1-(4-fluorophenyl)-1-methyl-ethyl, 1-(adamant-1-yl)-ethyl, 1-phenyl-1-methyl-ethyl, 2-(4-fluorophenyl)ethyl, 2-(7-methyl-indol-3-yl)ethyl, 2-(indol-3-yl)ethyl, 2-(thien-2-yl)ethyl, 3-(trifluoromethyl)benzyl, 3,3-diphenylpropyl, 3,4-difluorobenzyl, 4-(trifluoromethyl)benzyl, endo-(1R,2S,4R)-1,7,7-trimethylbicyclo[2.2.1]hept-2-yl, naphthalen-1-yl-methyl, benzyl, cyclohexylmethyl, cyclopentyl, methyl-N-(Naphthalen-1-yl-methyl), and phenyl;

$R_4$ is chosen from hydrogen and methyl;
$R_5$ is chosen from hydrogen and methyl; and
$R_6$ is hydrogen.

In another embodiment, the invention relates to compounds of formula (I):

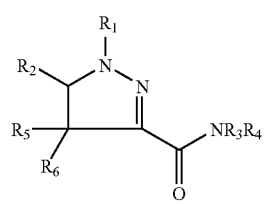

or tautomers, stereoisomers, N-oxides, isotopically-labelled analogues, or pharmaceutically acceptable salts of any of the foregoing, wherein the compounds of formula (I) are optically active enantiomers.

In a further embodiment, the invention relates to compounds of formula (I):

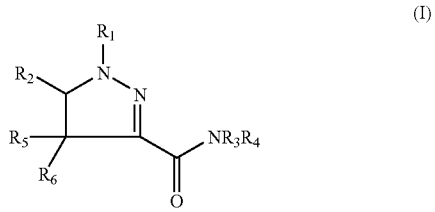

or tautomers, stereoisomers, N-oxides, isotopically-labelled analogues, or pharmaceutically acceptable salts of any of the foregoing, having cannabinoid $CB_1$ receptor agonistic activity.

In a further embodiment, the invention relates to compounds of formula (I), or pharmaceutically acceptable salts thereof, for the treatment of disorders in which cannabinoid receptors are involved, and in addition, that can be treated via manipulation of those receptors.

In one embodiment, the invention relates to compounds of formula (I), or pharmaceutically acceptable salts thereof, for the treatment of multiple sclerosis, traumatic brain injury, pain including chronic pain, neuropathic pain, acute pain and inflammatory pain, osteoporosis, appetite disorders, epilepsy, Alzheimer's disease, Tourette's syndrome, cerebral ischaemia and gastrointestinal disorders.

Other embodiments of the invention include, but are not limited to:

pharmaceutical compositions for treating, for example, at least one disorder or condition that may be treated by activating at least one cannabinoid $CB_1$ receptor, the compositions comprising a compound of formula (I), or a pharmaceutically acceptable salt thereof, and a pharmaceutically acceptable carrier;

methods of treatment of at least one disorder or condition that may be treated by activating at least one cannabinoid $CB_1$ receptor, the methods comprising administering to a mammal in need of such treatment a compound of formula (I) or a pharmaceutically acceptable salt thereof;

pharmaceutical compositions for treating, for example, at least one disorder or condition chosen multiple sclerosis, traumatic brain injury, pain including chronic pain, neuropathic pain, acute pain and inflammatory pain, osteoporosis, appetite disorders, epilepsy, Alzheimer's disease, Tourette's syndrome, cerebral ischaemia and gastrointestinal disorders;

methods of treatment of at least one disorder or condition chosen from the disorders listed herein, the methods comprising administering to a mammal in need of such treatment a compound of formula (I) or a pharmaceutically acceptable salt thereof;

pharmaceutical compositions for treatment of at least one disorder or condition chosen from the disorders listed herein, the compositions comprising a compound of formula (I) or a pharmaceutically acceptable salt thereof, and a pharmaceutically acceptable carrier;

methods of treatment of at least one disorder or condition that may be treated by activating at least one cannabinoid $CB_1$ receptor, the methods comprising administering to a patient in need of such treatment a compound of formula (I) or a pharmaceutically acceptable salt thereof; and methods of antagonizing at least one cannabinoid $CB_1$ receptor, which comprises administering to a subject in need thereof, an effective amount of a compound of formula (I).

The invention also provides for the use of at least one compound or salt according to formula (I) for the manufacture of a medicament.

The invention further relates to combination therapies wherein at least one compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment of one or more of the conditions listed. Such other therapeutic agent(s) may be administered prior to, simultaneously with, or following the administration of the compounds of the invention.

The invention also provides compounds, pharmaceutical compositions, kits and methods for the treatment of a disorder or condition that may be treated by activating at least one cannabinoid $CB_1$ receptor, the method comprising administering to a patient in need of such treatment a compound of formula (I) or a pharmaceutically acceptable salt thereof.

The invention also provides methods of preparing the compounds of the invention and the intermediates used in those methods.

Isolation and purification of the compounds and intermediates described herein can be affected, if desired, by any suitable separation or purification procedure such as, for example, filtration, extraction, crystallization, column chromatography, thin-layer chromatography, thick-layer chromatography, preparative low or high-pressure liquid chromatography, or a combination of these procedures. Specific illustrations of suitable separation and isolation procedures can be taken from the preparations and examples. However, other equivalent separation or isolation procedures could, of course, also be used.

The compounds of the present invention may contain one or more asymmetric centers and can thus occur as racemates and racemic mixtures, single enantiomers, diastereomeric mixtures and individual diastereomers.

All compounds of the present invention do contain at least one chiral center (at the 5-position of the 4,5-dihydropyrazole ring). Additional asymmetric centers may be present depending upon the nature of the various substituents on the molecule. Each such asymmetric center will independently produce two optical isomers, and it is intended that all of the possible optical isomers and diastereomers in mixtures and as pure or partially purified compounds are included within the ambit of this invention.

Cis and trans isomers of the compounds of formula (I) or of pharmaceutically acceptable salts thereof are also within the scope of the invention, and this also applies to tautomers of the compounds of formula (I) or pharmaceutically acceptable salts thereof.

Some of the crystalline forms for the compounds may exist as polymorphs, and as such are intended to be included in the present invention. In addition, some of the compounds may form solvates with water (i.e., hydrates) or common organic solvents, and such solvates are also intended to be encompassed within the scope of this invention.

Isotopically-labeled compounds of formula (I) or pharmaceutically acceptable salts thereof, including compounds of formula (I) isotopically-labeled to be detectable by PET or SPECT, are also included within the scope of the invention, and the same applies to compounds of formula (I) labeled with [$^{13}$C]-, [$^{14}$C]-, [$^3$H]-, [$^{18}$F]-, [$^{125}$I]- or other isotopically enriched atoms, suitable for receptor binding or metabolism studies.

The compounds of the invention may also be used as reagents or standards in the biochemical study of neurological function, dysfunction and disease.

DEFINITIONS

General terms used in the description of compounds herein disclosed bear their usual meanings. The term alkyl as used herein denotes a univalent saturated branched or straight hydrocarbon chain. Unless otherwise stated, such chains can contain from 1 to 18 carbon atoms. Representative of such alkyl groups are methyl, ethyl, propyl, isopropyl, butyl, isobutyl, sec-butyl, tert-butyl, pentyl, isopentyl, neopentyl, tert-pentyl, hexyl, isohexyl, heptyl, octyl, nonyl, decyl, undecyl, dodecyl, tridecyl, tetradecyl, pentadecyl, hexadecyl, heptadecyl, octadecyl, and the like. When qualified as 'lower', the alkyl group will contain from 1 to 6 carbon atoms. The same carbon content applies to the parent term 'alkane', and to derivative terms such as 'alkoxy'. The carbon content of various hydrocarbon containing moieties is indicated by a prefix designating the minimum and maximum number of carbon atoms in the moiety, i.e., the prefix $C_x$-$C_y$ defines the number of carbon atoms present from the integer "x" to the integer "y" inclusive. 'Alkyl($C_{1-3}$)' for example, means methyl, ethyl, n-propyl or isopropyl, and 'alkyl($C_{1-4}$)' means 'methyl, ethyl, n-propyl, isopropyl, n-butyl, sec-butyl, isobutyl or tert-butyl'. The term 'alkenyl' denotes straight or branched hydrocarbon radicals having one or more carbon-carbon double bonds, such as vinyl, allyl, butenyl, etc., and for example comprises ($C_{2-4}$)alkenyl. In 'alkynyl' groups the straight or branched hydrocarbon radicals have one or more carbon-carbon triple bonds, such as ethynyl, propargyl, 1-butynyl, 2-butynyl, etc., and e.g. includes ($C_{2-4}$)alkynyl. Unless otherwise stated, 'alkenyl' and 'alkynyl' chains can contain from 1 to 18 carbon atoms.

The term 'acyl' comprises alkyl($C_{1-3}$)carbonyl, arylcarbonyl or aryl-alkyl($C_{1-3}$)carbonyl. 'Aryl' embraces mono- or polycyclic aromatic groups, including phenyl, naphthyl, 1,2,3,4-tetrahydro-naphtyl, indenyl, fluorenyl, anthracenyl, phenanthrenyl, naphthacenyl and azulenyl. 'Heteroaryl' embraces mono- or polycyclic hetero-aromatic, including furyl, thienyl, pyrrolyl, oxazolyl, thiazolyl, imidazolyl, imidazo[2,1-b][1,3]thiazolyl, pyrazolyl, isoxazolyl, isothiazolyl, pyridyl, pyridazinyl, pyrimidinyl, pyrazinyl, 1,3,5-triazinyl, indazolyl, indolyl, indolizinyl, isoindolyl, benzo[b]furanyl, 1,2,3,4-tetrahydroiso-quinolinyl, indanyl, indenyl, benzo[b]thienyl, 2,3-dihydro-1,4-benzodioxin-5-yl, benzimidazolyl, cinnolinyl, carbazolyl, acridinyl, phenazinyl, phenothiazinyl, phenoxazinyl, benzothiazolyl, benzo[1,2,5]thia-diazolyl, purinyl, quinolinyl, isoquinolinyl, quinolizinyl, phtalazinyl, quinazolinyl, quinoxalinyl, 1,8-naphthyridinyl and pteridinyl.

'Halo' or 'Halogen' means chloro, fluoro, bromo or iodo; 'hetero' as in 'heteroalkyl, heteroaromatic' etc. means containing one or more N, O or S atoms. 'heteroalkyl' includes alkyl groups with heteroatoms in any position, thus including N-bound O-bound or S-bound alkyl groups.

The term "substituted" means that the specified group or moiety bears one or more substituents. Where any group may carry multiple substituents, and a variety of possible substituents is provided, the substituents are independently selected, and need not to be the same. The term "unsubstituted" means that the specified group bears no substituents. With reference to substituents, the term "independently" means that when more than one of such substituents are possible, they may be the same or different from each other.

'$C_{3-8}$-cycloalkyl' means cyclopropyl, cyclobutyl, cyclopentyl, cyclohexyl, cycloheptyl or cyclooctyl; '$C_{5-8}$ heterocycloalkyl' refers to heteroatom containing rings including but not limited to piperidinyl, morpholinyl, azepanyl, pyrrolidinyl, thiomorpholinyl, piperazinyl, tetrahydrofuryl, tetrahydropyranyl; '$C_{5-10}$ bicycloalkyl group' refers to carbobicyclic ring systems including but not limited to bicyclo[2.2.1]heptanyl, bicyclo[3.3.0]octanyl or the bicyclo[3.1.1]heptanyl group; '$C_{6-10}$ tricycloalkyl group' refers to carbotricyclic ring systems including but not limited to the 1-adamantyl, noradamantyl or the 2-adamantyl group. The abbreviation '$C_{8-11}$ tetracycloalkyl group' refers to carbotetracyclic ring systems including but not limited to the cubyl, homocubyl or bishomocubyl group.

The terms "oxy", "thio" and "carbo" as used herein as part of another group respectively refer to an oxygen atom, a sulphur atom and a carbonyl (C=O) group, serving as linker between two groups, such as for instance hydroxyl, oxyalkyl, thioalkyl, carboxyalkyl, etc. The term "amino" as used herein alone, or as part of another group, refers to a nitrogen atom that may be either terminal, or a linker between two other groups, wherein the group may be a primary, secondary or tertiary (two hydrogen atoms bonded to the nitrogen atom, one hydrogen atom bonded to the nitrogen atom and no hydrogen atoms bonded to the nitrogen atom, respectively) amine. The terms "sulfinyl" and "sulfonyl" as used herein as part of another group respectively refer to an —SO— or an —SO$_2$— group.

To provide a more concise description, the terms 'compound' or 'compounds' include tautomers, stereoisomers, N-oxides, isotopically-labelled analogues, or pharmacologically acceptable salts, also when not explicitly mentioned.

As used herein, the term "leaving group" (L) shall mean a charged or uncharged atom or group that departs during a substitution or displacement reaction. The term refers to groups readily displaceable by a nucleophile, such as an amine, a thiol or an alcohol nucleophile. Such leaving groups are well known in the art (Smith, 2001). Examples include, but are not limited to, N-hydroxysuccinimide, N-hydroxybenzotriazole, halides (Br, Cl, I), triflates, mesylates, tosylates, and the like.

N-oxides of the compounds mentioned above belong to the invention. Tertiary amines may or may not give rise to N-oxide metabolites. The extent to what N-oxidation takes place varies from trace amounts to a near quantitative conversion. N-oxides may be more active than their corresponding tertiary amines, or less active. Whilst N-oxides can easily be reduced to their corresponding tertiary amines by chemical means, in the human body this happens to varying degrees. Some N-oxides undergo nearly quantitative reductive conversion to the corresponding tertiary amines, in other cases conversion is a mere trace reaction, or even completely absent (Bickel, 1969).

'Form' is a term encompassing all solids: polymorphs, solvates, amorphous forms. 'Crystal form' refers to various solid forms of the same compound, for example polymorphs, solvates and amorphous forms. 'Cocrystals' are multicomponent crystals with a unique lattice: new chemical species produced with neutral compounds. 'Amorphous forms' are non-crystalline materials with no long range order, and generally do not give a distinctive powder X-ray diffraction pattern. Crystal forms in general have been described by Byrn (1995) and Martin (1995). 'Polymorphs' are crystal structures in which a compound can crystallize in different crystal packing arrangements, all of which have the same elemental composition. Polymorphism is a frequently occurring phenomenon, affected by several crystallization conditions such as temperature, level of supersaturation, the presence of impurities, polarity of solvent, rate of cooling. Different polymorphs usually have different X-ray diffraction patterns, solid state NMR spectra, infrared or Raman spectra, melting points, density, hardness, crystal shape, optical and electrical properties, stability, and solubility. Recrystallization solvent, rate of crystallization, storage temperature, and other factors may cause one crystal form to dominate.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

Throughout the description and the claims of this specification the word "comprise" and variations of the word, such as "comprising" and "comprises" is not intended to exclude other additives, components, integers or steps.

While it may be possible for the compounds of formula (I) to be administered as the raw chemical, in at least one embodiment, they are presented in a 'pharmaceutical composition'. According to a further aspect, the present invention provides a pharmaceutical composition comprising a compound of formula (I), or a pharmaceutically acceptable salt or solvate thereof, together with one or more pharmaceutically acceptable carriers thereof, and optionally one or more other therapeutic ingredients. The carrier(s) must be 'acceptable' in the sense of being compatible with the other ingredients of the formulation and not deleterious to the recipient thereof.

The term "composition" as used herein encompasses a product comprising specified ingredients in predetermined amounts or proportions, as well as any product that results, directly or indirectly, from combining specified ingredients in specified amounts. In relation to pharmaceutical compositions, this term encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. The pharmaceutical composition includes enough of the active object compound to produce the desired effect upon the progress or condition of diseases. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

Within the context of this application, the term 'combination preparation' comprises both true combinations, meaning a compound of formula (I) and other medicaments physically combined in one preparation such as a tablet or injection fluid, as well as 'kit-of-parts', comprising a compound of formula (I) and another medicament in separate dosage forms, together with instructions for use, optionally with further means for facilitating compliance with the administration of the component compounds, e.g., label or drawings. With true combinations, the pharmacotherapy by definition is simultaneous. The contents of 'kit-of-parts', can be administered either simultaneously or at different time intervals. Therapy being either concomitant or sequential will be dependant on the characteristics of the other medicaments used, characteristics like onset and duration of action, plasma levels, clearance, etc., as well as on the disease, its stage, and characteristics of the individual patient.

The affinity of the compounds of the invention for cannabinoid $CB_1$ receptors was determined as described below. From the binding affinity measured for a given compound of formula (I), one can estimate a theoretical lowest effective dose. At a concentration of the compound equal to twice the measured $K_i$-value, nearly 100% of the cannabinoid $CB_1$ receptors likely will be occupied by the compound. Converting that concentration to mg of compound per kg of patient—assuming ideal bioavailability—results in a theoretical lowest effective dose. Pharmacokinetic, pharmacodynamic, and other considerations may alter the dose actually administered to a higher or lower value. The dose of the compound to be administered will depend on the relevant indication, the age, weight and sex of the patient and may be determined by a physician. In general, the dosage may be in amounts, for example from 0.01 mg/kg to 10 mg/kg. The typical daily dose of the active ingredients varies within a wide range and will depend on various factors such as the relevant indication, the route of administration, the age, weight and sex of the patient and may be determined by a physician. In general, total daily dose administration to a patient in single or individual doses, may be in amounts, for example, from 0.001 to 10 mg/kg body weight daily, and more usually from 0.01 to 1,000 mg per day, of total active ingredients. Such dosages will be administered to a patient in need of treatment from one to three times each day, or as often as needed for efficacy, and for periods of at least two months, more typically for at least six months, or chronically.

The term "therapeutically effective amount" as used herein refers to an amount of a therapeutic agent to treat a condition treatable by administrating a composition of the invention. That amount is the amount sufficient to exhibit a detectable therapeutic or ameliorative response in a tissue system, animal or human. The effect may include, for example, treating the conditions listed herein. The precise effective amount for a subject will depend upon the subject's size and health, the nature and extent of the condition being treated, recommendations of the treating physician (researcher, veterinarian, medical doctor or other clinician), and the therapeutics, or combination of therapeutics, selected for administration. Thus, it is not useful to specify an exact effective amount in advance.

A "pharmaceutical salt" refers to an acid:base complex containing an active pharmaceutical ingredient (API) along with additional non-toxic molecular species in the same crystal structure. The term "pharmaceutically acceptable salt" refers to those salts that are, within the scope of sound medical judgment, suitable for use in contact with the tissues of humans and lower animals without undue toxicity, irritation, allergic response, etc., and are commensurate with a reasonable benefit/risk ratio. Pharmaceutically acceptable salts are well-known in the art. They can be prepared in situ when finally isolating and purifying the compounds of the invention, or separately by reacting them with pharmaceutically acceptable non-toxic bases or acids, including inorganic or organic bases and inorganic or organic acids (Berge, 1977). Common anions used in pharmaceutically acceptable salts include: chloride, bromide, sulfate, nitrate, phosphate, bicarbonate, mesylate, esylate, isothianate, tosylate, napsylate, besylate, acetate, propionate, maleate, benzoate, salicylate, fumarate, citrate, lactate, maleate, tartrate, pamoate, succinate, glycolate, hexanoate, octanoate, decanoate, stearate, oleate, aspartate and glutamate. Common cations used as counterions in pharmaceutically acceptable salts include: sodium, potassium, calcium, magnesium, lithium, zinc, aluminum, arginine, lysine, histidine, triethylamine, ethanolamine, triethanolamine, ethilenediamine, meglumine, procaine and benzathine.

The 'free base' form may be regenerated by contacting the salt with a base or acid, and isolating the parent compound in the conventional matter. The parent form of the compound differs from the various salt forms in certain physical properties, such as solubility in polar solvents, but otherwise the salts are equivalent to the parent form of the compound for the purposes of the present invention.

The term "treatment" as used herein refers to any treatment of a mammalian, for example human condition or disease, and includes: (1) inhibiting the disease or condition, i.e., arresting its development, (2) relieving the disease or condition, i.e., causing the condition to regress, or (3) stopping the symptoms of the disease. The term 'inhibit' includes its generally accepted meaning which includes restraining, alleviating, ameliorating, and slowing, stopping or reversing progression, severity, or a resultant symptom. As used herein, the term "medical therapy" intendeds to include diagnostic and therapeutic regimens carried out in vivo or ex vivo on humans or other mammals. 'Mammals' include animals of economic importance such as bovine, ovine, and porcine animals, especially those that produce meat, as well as domestic animals, sports animals, zoo animals, and in at least one embodiment humans. The term "subject" as used herein, refers to an animal, in at least one embodiment, a mammal, for example a human, who has been the object of treatment, observation or experiment.

EXAMPLES

Example 1

Materials and Methods $^1$H NMR spectra were recorded on a Varian UN400 instrument (400 MHz) using DMSO-$d_6$ or CDCl$_3$ as solvents with tetramethylsilane as an internal standard. Chemical shifts are given in ppm ($\delta$ scale) downfield from tetramethylsilane. Coupling constants (J) are expressed in Hz. Flash chromatography was performed using silica gel 60 (0.040-0.063 mm, Merck). Column chromatography was performed using silica gel 60 (0.063-0.200 mm, Merck). Sepacore chromatographic separations were carried out using Supelco equipment, VersaFLASH™ columns, VersaPak™ silica cartridges, Büchi UV monitor C-630, Büchi Pump module C-605, Büchi fraction collector C-660 and Büchi pump manager C-615. Melting points were recorded on a Büchi B-545 melting point apparatus or determined by DSC (differential scanning calorimetry) methods. Optical rotations ($[\alpha]_D$) were measured on an Optical Activity polarimeter. Specific rotations are given as deg/dm, the concentration values are reported as g/100 mL of the specified solvent and were recorded at 23° C., unless indicated otherwise.

Example 2

General Aspects of Syntheses

Pyrazoline derivatives can be obtained by published methods (Bach, 1994). The synthesis of compounds having formula (I) is outlined in Scheme 1. Additional information on activating and coupling methods of amines to carboxylic acids can be found in the literature (Bodanszky, 1994; Akaji, 1994; Albericio, 1997; Montalbetti, 2005).

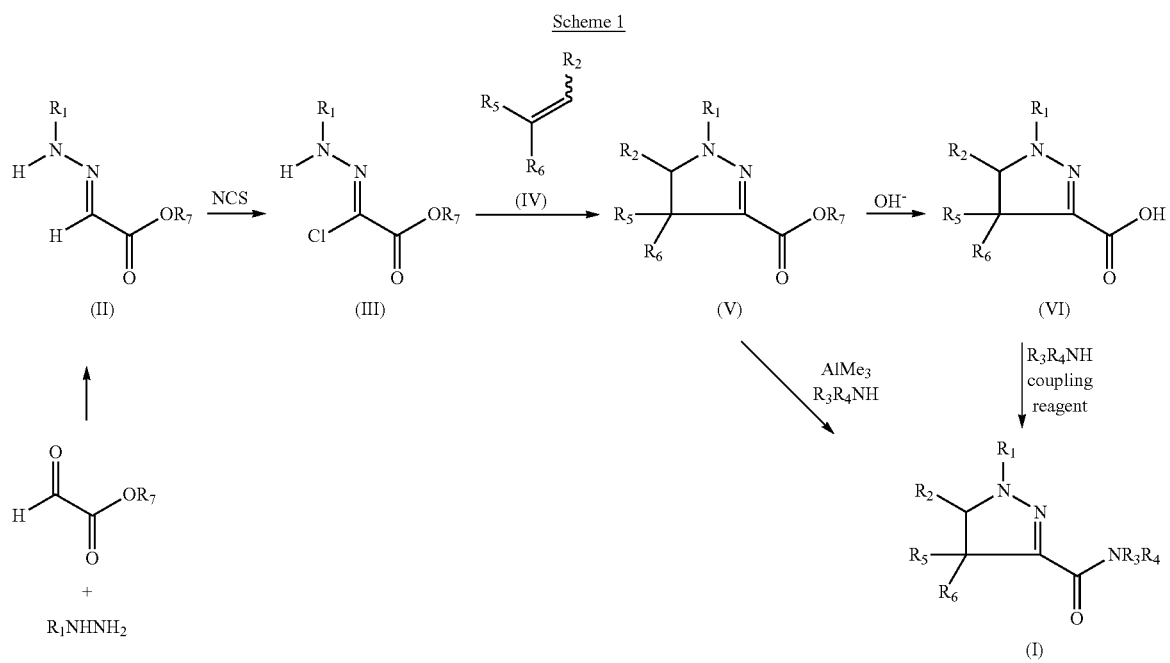

A hydrazone derivative of general formula (II) wherein $R_1$ has the abovementioned meaning and $R_7$ is a $C_{1-3}$ alkyl group, such as an ethyl group, can be obtained from a compound of general formula $R_1NHNH_2$ and ethylglyoxalate. A hydrazone derivative of general formula (II) can be reacted with a chlorinating agent such as tert-butyl hypochlorite or N-chlorosuccinimide (NCS) in an inert solvent to give a compound of general formula (III). A compound of general formula (III) wherein $R_1$ has the abovementioned meaning, and $R_7$ is a $C_{1-3}$ alkyl group can be reacted with a compound of general formula (IV), wherein $R_2$, $R_5$ and $R_6$ have the abovementioned meaning, to give a compound of general formula (V) wherein $R_1$, $R_2$, $R_5$, $R_6$ and $R_7$ have the abovementioned meaning. A compound of general formula (V) can be reacted with a base such as aqueous potassium hydroxide or lithium hydroxide to give a carboxylic acid derivative of general formula (VI), or a sodium, potassium, lithium or cesium salt thereof, wherein $R_1$, $R_2$, $R_5$ and $R_6$ have the abovementioned meaning. A compound of general formula (VI) can be reacted with an amine of general formula $R_3R_4NH$, wherein $R_3$ and $R_4$ have the abovementioned meaning, in the presence of an activating or coupling reagent such as 2-chloro-1,3-dimethylimidazolinium hexafluorophosphate (CIP), O-benzotriazol-1-yl-N,N,N',N'-tetramethyluronium tetrafluoroborate (TBTU) or O-benzotriazol-1-yl-N,N,N',N'-tetramethyl-uronium hexafluorophosphate (HBTU) in an inert organic solvent such as dichloromethane to give a compound of general formula (I) wherein $R_1$, $R_2$, $R_3$, $R_4$, $R_5$ and $R_6$ have the abovementioned meaning. In one embodiment, a base such as triethylamine or Hünigs base (DIPEA) may be added in such reactions.

Alternatively, an ester derivative having formula (V) can be reacted in a so-called Weinreb amidation reaction with an amine of general formula $R_3R_4NH$ to give a compound of general formula (I). Such Weinreb amidation reactions can be promoted by the use of trimethylaluminum $Al(CH_3)_3$ (For more information on aluminum-mediated conversion of esters to amides, see Levin, 1982).

Another alternative is to chlorinate a carboxylic acid derivative having formula (VI) to the corresponding acid chloride (Va) wherein $R_8$ is a chloro atom using a chlorinating agent such as thionyl chloride ($SOCl_2$) or oxalyl chloride. The formed acid chloride derivative can subsequently be reacted with an amine of general formula $R_3R_4NH$ to give a compound of general formula (I), wherein $R_1$, $R_2$, $R_3$, $R_4$, $R_5$ and $R_6$ have the abovementioned meaning.

In one embodiment, the invention relates to compounds of formula (Va):

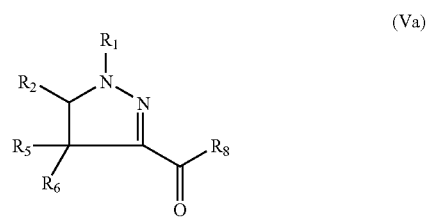

(Va)

or tautomers, stereoisomers, N-oxides, isotopically-labelled analogues, or pharmacologically acceptable salts of any of the foregoing,
wherein $R_1$, $R_2$, $R_5$ and $R_6$ have the abovementioned meaning and $R_8$ is chosen from chloro and $OR_7$, where $R_7$ is $C_{1-3}$ alkyl, provided that if $R_2$ is phenyl and $R_1$ is benzyl, then $R_7$ is not ethyl. Such compounds are useful in the synthesis of compounds of the general formula (I).

In another embodiment, the invention relates to compounds of formula (VI):

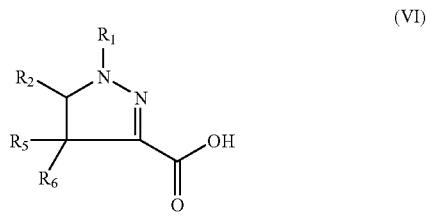

(VI)

and to sodium, potassium, lithium and cesium salts thereof, wherein:
$R_1$, $R_2$, $R_5$ and $R_6$ have the same meanings as given above, provided that if $R_2$ is phenyl, then $R_1$ is not benzyl. Such compounds are useful in the synthesis of compounds of the general formula (I).

Scheme 2

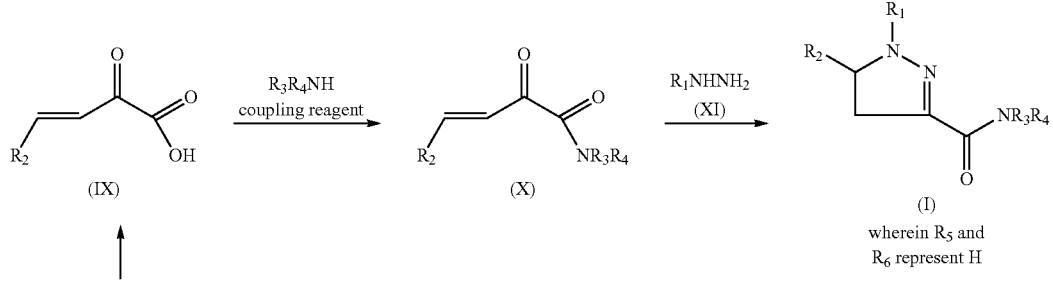

wherein $R_5$ and $R_6$ represent H

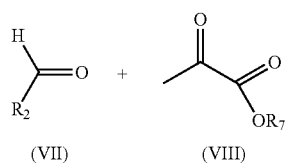 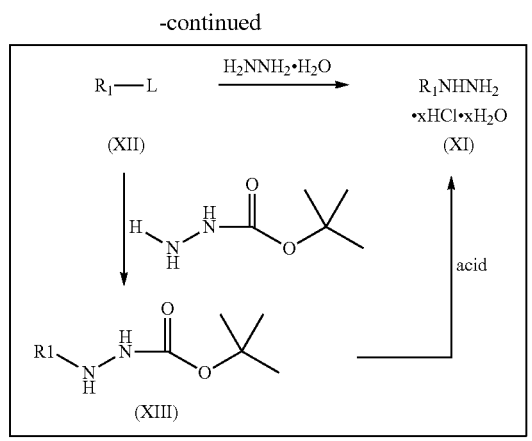

Alternatively, a compound of general formula (I) wherein $R_5$ and $R_6$ are hydrogen atoms, and $R_1$, $R_2$, $R_3$ and $R_4$ have the abovementioned meaning can be prepared according to the route described in Scheme 2. A compound of general formula (IX) wherein $R_2$ has the abovementioned meaning can be obtained from an aldehyde of general formula (VII) and a compound of general formula (VIII) in the presence of a base such as aqueous potassium hydroxide or sodium hydroxide in a solvent such as ethanol (Annan, 1989). The formed 2-oxo-buten-3-oic acid derivative (IX) can be reacted with a compound of general formula $R_3R_4NH$ in an inert organic solvent such as dichloromethane in the presence of an activating or coupling reagent such as HBTU to give an amide derivative of general formula (X), wherein $R_2$, $R_3$ and $R_4$ have the abovementioned meaning. In one embodiment, a base such as triethylamine or Hünigs base (DIPEA) may be added in such a reaction. A compound of of general formula (X) can be reacted with a hydrazine derivative of general formula $R_1NHNH_2$ or its hydrate $R_1NHNH_2.H_2O$ or a salt thereof, wherein $R_1$ has the abovementioned meaning, to give a compound of general formula (I) wherein $R_1$, $R_2$, $R_3$ and $R_4$ have the abovementioned meaning, and $R_5$ and $R_6$ are hydrogen atoms. A hydrazine of general formula $R_1NHNH_2$ (XI) can be prepared from hydrazine or hydrazine hydrate or a salt thereof and a compound of general formula $R_1$-L (XII) wherein L is a 'leaving group' such as iodide, bromide or choride in an organic solvent such as ethanol, analogously to the method described (Chem. Ber. 1965). Alternatively, a hydrazine of general formula $R_1NHNH_2$ (XI) or its hydrate $R_1NHNH_2.H_2O$ or a salt thereof, wherein $R_1$ has the abovementioned meaning, can be prepared from a compound of general formula $R_1$-L (XII) in an organic solvent such as acetonitrile, in a reaction with a protected hydrazine derivative such as tert-butylcarbazate to give a compound of general formula (XIII) which compound of general formula (XIII) is subsequently reacted with an acid such as hydrochloric acid in an inert organic solvent such as 1,4-dioxane.

In one embodiment, the invention relates to compounds of the general formula (X):

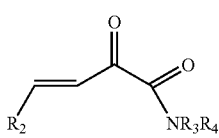
(X)

wherein $R_2$ has the same meaning as given hereinabove, $R_3$ is a hydrogen atom, and $R_4$ is chosen from $C_{6-10}$ bicycloalkyl and $C_{7-10}$ tricycloalkyl, each of which may be optionally substituted with 1-5 substituents, wherein the substituents are the same or different and are chosen from methyl, ethyl, hydroxyl, amino, and fluoro or $R_4$ is chosen from 2-phenyl-1,1-dimethyl-ethyl and 1-phenyl-1-methyl-ethyl, wherein the phenyl groups are optionally substituted with 1-5 substituents Y is as defined above. Such compounds being useful in the synthesis of compounds of the general formula (I) are new.

The selection of the particular synthetic procedures depends on factors known to those skilled in the art such as the compatibility of functional groups with the reagents used, the possibility to use protecting groups, catalysts, activating and coupling reagents and the ultimate structural features present in the final compound being prepared.

Pharmaceutically acceptable salts may be obtained using standard procedures well known in the art, for example by mixing a compound of the present invention with a suitable acid, for instance an inorganic acid such as hydrochloric acid, or with an organic acid such as fumaric acid.

According to these procedures the compounds described below have been prepared. They are intended to further illustrate the invention in more detail, and therefore are not deemed to restrict the scope of the invention in any way. Other embodiments of the invention will be apparent to those skilled in the art from consideration of the specification and practice of the invention disclosed herein. It is thus intended that the specification and examples be considered as exemplary only.

Example 3

Synthesis and Spectral Data of Intermediates

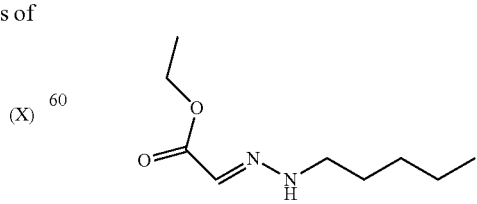

Intermediate II-1

To a magnetically stirred solution of oxo-acetic acid ethyl ester (35.08 ml, 177 mmol; 50% solution in toluene) in ethanol (450 ml) was added n-pentylhydrazine (21.7 g, 212 mmol) and the resulting solution was heated at 80° C. for 16 hours. The obtained mixture was allowed to attain room temperature and concentrated. The resulting residue was taken up in ethylacetate and water. The organic layer was separated and subsequently dried over MgSO₄, filtered and concentrated to give (pentylhydrazono)acetic acid ethyl ester (Intermediate II-1) (32.2 gram, 93% yield) as a purple colored oil. ¹H-NMR (400 MHz, CDCl₃) δ 0.87-0.94 (m, 3H), 1.25-1.42 (m, 7H), 1.55-1.68 (m, 2H), 3.17-3.23 (m, 1H), 3.35-3.45 (m, 1H), 4.28 (q, J=7, 2H), 6.51 (br s, 1H), 6.72 (s, 1H).

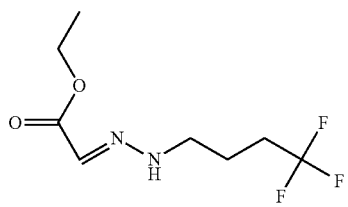

Intermediate II-2

Intermediate (II-2) was obtained in 94% yield analogously to the preparation of intermediate (II-1) from oxo-acetic acid ethyl ester and 4,4,4-trifluorobutylhydrazine.HCl.H₂O (Intermediate XI-3) in the presence of 1.2 molar equivalent of Hünig's base (DIPEA). ¹H-NMR (400 MHz, CDCl₃) δ 1.33 (t, J=7.1 Hz, 3H), 1.84-1.97 (m, 2H), 2.11-2.27 (m, 2H), 3.33-3.40 (m, 2H), 4.28 (q, J=7.2 Hz, 2H), 6.50 (br s, 1H), 6.80 (s, 1H).

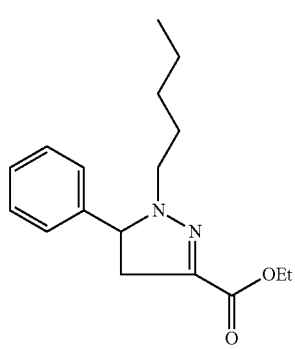

Intermediate V-1

To a magnetically stirred solution of (pentylhydrazono)acetic acid ethyl ester (Intermediate II-1) (35.16 g, 179 mmol) in ethylacetate (450 ml) was added N-chlorosuccinimide (NCS) (26.34 g, 197 mmol) and the resulting mixture was heated at 60° C. for 1 hour in a nitrogen atmosphere. To the reaction mixture was added styrene (41.1 ml, 359 mmol) and potassium bicarbonate (89.8 g, 897 mmol) and water (8 ml). The resulting mixture was heated at 70° C. for 16 hours. The resulting mixture was allowed to attain room temperature, concentrated in vacuo and the resulting residue was chromatographically separated using Sepacore equipment (eluant: dichloromethane/methanol=98/2 v/v) to give ethyl 1-(n-pentyl)-5-phenyl-4,5-dihydro-(1H)-pyrazole-3-carboxylate (Intermediate (V-1) (12.1 g, 22% yield) as an oil. ¹H-NMR (400 MHz, CDCl₃) δ 0.83 (t, J=7, 3H), 1.13-1.28 (m, 4H), 1.35 (t, J=7, 3H), 1.53-1.67 (m, 2H), 2.89 (dd, J=16 and 13, 1H), 3.01-3.09 (m, 1H), 3.14-3.22 (m, 1H), 3.41 (dd, J=16 and 12, 1H), 4.31 (double (diastereotopic) quartet, J~7, 2H), 4.63 (dd, J=13 and 12, 1H), 7.27-7.39 (m, 5H).

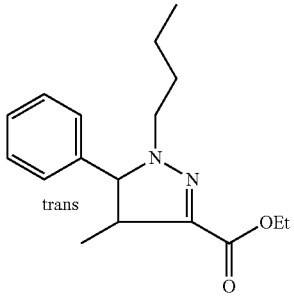

Intermediate V-2

Intermediate (V-2) was obtained analogously to the preparation of intermediate (V-1) from (butylhydrazono)acetic acid ethyl ester via successive chlorination with N-chlorosuccinimide (NCS) and treatment with trans-beta-methylstyrene. Chromatographic purification using Sepacore equipment (eluant: petroleum eter (40-60)/ethylacetate=9/1 v/v)) gave ethyl 1-(n-butyl)-trans-4-methyl-5-phenyl-4,5-dihydro-(1H)-pyrazole-3-carboxylate (Intermediate (V-2) in 14% yield. ¹H-NMR (400 MHz, CDCl₃) δ 0.95 (t, J=7, 3H), 1.18-1.43 (m, 8H), 1.49-1.66 (m, 2H), 3.03-3.26 (m, 3H), 4.09 (d, J=12 Hz, 1H), 4.27-4.37 (m, 2H), 7.28-7.40 (m, 5H).

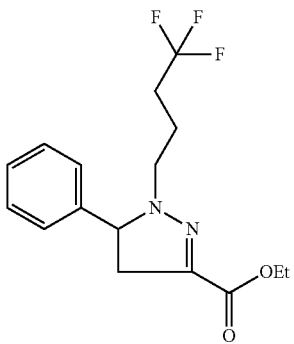

Intermediate V-3

Intermediate (V-3) was obtained analogously to the preparation of intermediate (V-1) from (4,4,4-trifluorobutylhydrazono)acetic acid ethyl ester (Intermediate II-2) via successive reactions with N-chlorosuccinimide (NCS) and styrene to give crude intermediate (V-3). This crude material was chromatographically purified by using flash chromatography (eluant gradient: petroleum ether (40-60)/ethylacetate=95/5=>petroleum ether (40-60)/ethylacetate=93/7 (v/v)) to give ethyl 1-(4,4,4-trifluorobutyl)-5-phenyl-4,5-dihydro-(1H)-pyrazole-3-carboxylate (Intermediate (V-3) (34% yield). ¹H-NMR (400 MHz, CDCl₃) δ 1.35 (t, J=7 Hz, 3H), 1.75-2.22 (m, 4H), 2.93 (dd, J=18 and 14 Hz, 1H), 3.06-3.21 (m, 2H), 3.41 (dd, J=18 and 12 Hz, 1H), 4.33 (double (diastereotopic) quartet, J~7, 2H), 4.55 (dd, J=14 and 12 Hz, 1H), 7.31-7.42 (m, 5H).

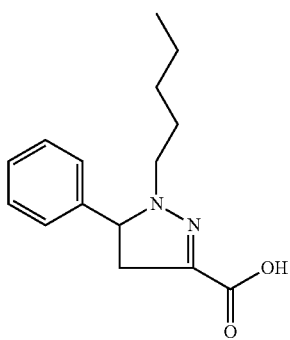

Intermediate VI-1

To a magnetically stirred solution of ethyl 1-(n-pentyl)-5-phenyl-4,5-dihydro-(1H)-pyrazole-3-carboxylate (Intermediate (V-1) (11.76 g, 38.74 mmol) in tetrahydrofuran (100 ml) and water (100 ml) was added lithium hydroxide (1.86 g, 77.5 mmol) and the resulting mixture was heated at 70° C. for 1 hour. The reaction mixture was allowed to attain room temperature and diethyl ether (200 ml) and concentrated hydrochloric acid (7 ml) were added. The organic layer was separated, washed three times with water and with brine and subsequently dried over $Na_2SO_4$, filtered and concentrated in vacuo to give 1-(n-pentyl)-5-phenyl-4,5-dihydro-(1H)-pyrazole-3-carboxylic acid (Intermediate (VI-1) (7.9 g, 74% yield) as an oil. $^1$H-NMR (400 MHz, $CDCl_3$) δ 0.84 (t, J=7, 3H), 1.15-1.28 (m, 4H), 1.53-1.65 (m, 2H), 2.92 (dd, J=17 and 13, 1H), 3.02-3.11 (m, 1H), 3.18-3.27 (m, 1H), 3.44 (dd, J=17 and 13, 1H), 4.75 t, J=13, 1H), 7.31-7.41 (m, 5H), 7.42-9.00 (br s, 1H).

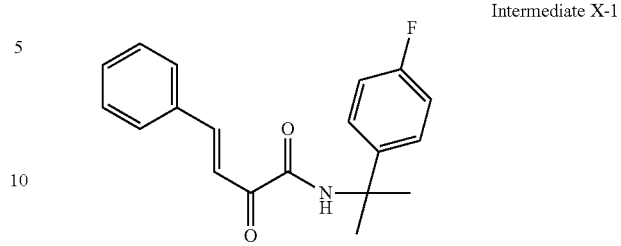

Intermediate X-1

To a magnetically stirred solution of the commercially available E-2-oxo-4-phenyl-but-3-enoic acid (4.40 gram, 25 mmol) in dichloromethane (100 ml) was successively added 1-(4-fluorophenyl)-1-methyl-ethylamine (3.83 g, 25 mmol), N-ethyldiisopropylamine (DIPEA) (8.56 ml, 50 mmol) and O-benzotriazol-1-yl-N,N,N',N'-tetramethyluronium hexafluorophosphate (HBTU) (9.48 gram, 25 mmol) and the resulting mixture was reacted at room temperature for 16 hours in a nitrogen atmosphere. The organic layer was washed twice with water and subsequently dried over $MgSO_4$, filtered and concentrated in vacuo to give crude E-2-oxo-4-phenyl-but-3-enoic acid [1-(4-fluorophenyl)-1-methyl-ethyl]amide (Intermediate X-I) as an oil. Further chromatographic purification using Sepacore equipment (eluant: petroleum ether/ethylacetate=95/5 (v/v)) gave intermediate X-I as an oil which slowly solidified on standing (5.15 g, 65% yield). $^1$H-NMR (400 MHz, $CDCl_3$) δ 1.77 (s, 6H), 7.00-7.05 (m, 2H), 7.35-7.45 (m, 5H), 7.52 (br s, 1H), 7.61-7.65 (m, 2H), 7.73 (d, J=16, 1H), 7.92 (d, J=16, 1H).

Intermediate IX-1

To a magnetically stirred solution of ethyl 2-fluorobenzaldehyde (11.7 ml, 110 mmol) and ethylglyoxalate (11.1 ml, 100 mmol) in ethanol (50 ml) was slowly added a solution of sodium hydroxide (4.4 g (110 mmol) in 50 ml water) in a nitrogen atmosphere while the temperature was kept between 0° C. and 10° C. After stirring for another 45 minutes the reaction mixture was allowed to attain room temperature and stirred for 2 hours. The formed precipitate was collected by filtration and successively washed with ethanol and a 1N HCl solution (200 ml) and subsequently dried to give E-2-oxo-4-(2-fluorophenyl)-but-3-enoic acid (11.1 gram, 57% yield) Melting point: 100-102.5° C. $^1$H-NMR (400 MHz, $CDCl_3$) δ 7.13-7.27 (m, 2H), 7.45-7.53 (m, 1H) 7.66-7.74 (m, 2H), 8.26 (d, J=16, 1H), invisible —OH proton.

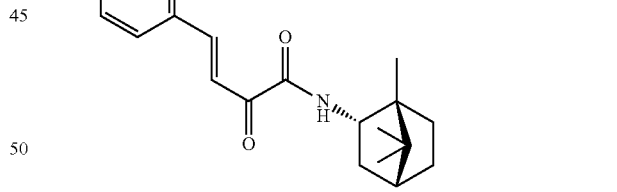

Intermediate X-2

Intermediate X-2 (E-2-oxo-4-phenyl-but-3-enoic acid [endo-(1R,2S,4R)-1,7,7-trimethylbicyclo-[2.2.1]hept-2-ylamide]) was obtained from E-2-oxo-4-phenyl-but-3-enoic acid and endo-(1R,2S,4R)-1,7,7-trimethylbicyclo[2.2.1]hept-2-ylamine (CAS 32511-34-5) analogously to the procedure described for intermediate X-1. $^1$H-NMR (400 MHz, $CDCl_3$) δ 0.84-1.00 (m, 10H), 1.21-1.29 (m, 1H), 1.38-1.48 (m, 1H), 1.53-1.62 (m, 1H), 1.70-1.86 (m, 2H), 2.33-2.44 (m, 1H), 4.22-4.30 (m, 1H), 7.20-7.26 (m, 1H), 7.39-7.46 (m, 3H), 7.65-7.70 (m, 2H), 7.78 (d, J=16, 1H), 7.95 (d, J=16, 1H).

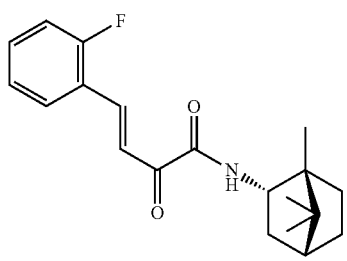

Intermediate X-3

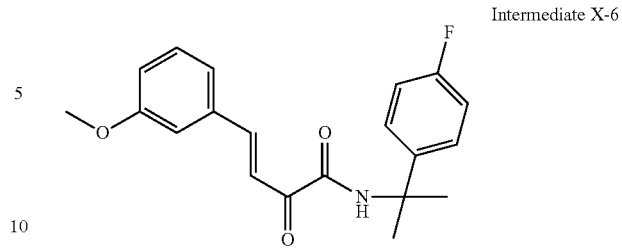

Intermediate X-6

Intermediate X-3 (E-2-oxo-4-(2-fluorophenyl)-but-3-enoic acid [endo-(1R,2S,4R)-1,7,7-trimethylbicyclo[2.2.1]hept-2-ylamide]) was obtained from E-2-oxo-4-(2-fluorophenyl)-but-3-enoic acid (Intermediate IX-1) and endo-(1R,2S,4R)-1,7,7-trimethylbicyclo[2.2.1]hept-2-ylamine analogously to the procedure described for intermediate X-1. $^1$H-NMR (400 MHz, CDCl$_3$) δ 0.84-1.00 (m, 10H), 1.21-1.30 (m, 1H), 1.38-1.48 (m, 1H), 1.53-1.62 (m, 1H), 1.70-1.87 (m, 2H), 2.34-2.44 (m, 1H), 4.21-4.30 (m, 1H), 7.10-7.25 (m, 3H), 7.38-7.45 (m, 1H), 7.70-7.75 (m, 1H), 7.85 (d, J=16, 1H), 8.12 (d, J=16, 1H).

Intermediate X-6 (E-2-oxo-4-(3-methoxyphenyl)-but-3-enoic acid [1-(4-fluorophenyl)-1-methyl-ethyl]amide was obtained from E-2-oxo-4-(3-methoxyphenyl)-but-3-enoic acid and 1-(4-fluorophenyl)-1-methyl-ethylamine analogously to the procedure described for intermediate X-1. $^1$H-NMR (400 MHz, CDCl$_3$) δ 1.77 (s, 6H), 3.81 (s, 3H), 6.95-7.05 (m, 3H), 7.13-7.16 (m, 1H), 7.18-7.22 (m, 1H), 7.28-7.33 (m, 1H), 7.36-7.40 (m, 2H), 7.54 (br s, 1H), 7.71 (d, J=16 Hz, 1H), 7.88 (d, J=16 Hz, 1H).

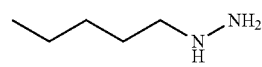

Intermediate XI-1

To a magnetically stirred solution of hydrazine hydrate (243 ml, 5 mol) was very slowly added a solution of 1-bromopentane (62 ml, 0.50 mol) in ethanol (50 ml) while keeping the temperature at 20° C. The resulting mixture was reacted at room temperature for 2 hours. The mixture was extracted with diethyl ether. The diethyl ether extract was concentrated and BaO (5 gram) was added to the residue. Distillation in vacuo gave n-pentylhydrazine (Intermediate XI-1) at 30-40 mbar pressure at 72° C.-78° C. (30.36 gram, 48% yield). $^1$H-NMR (400 MHz, CDCl$_3$) δ 0.90 (t, J=7, 3H), 1.27-1.38 (m, 4H), 1.45-1.58 (m, 2H), 2.76 (t, J=7, 2H), 2.85 (br s, 3H).

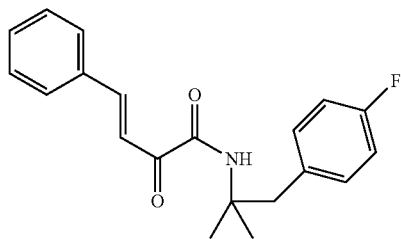

Intermediate X-4

Intermediate X-4 (E-2-oxo-4-phenyl-but-3-enoic acid [2-(4-fluorophenyl)-2,2-dimethyl-ethyl]amide was obtained from E-2-oxo-4-phenyl-but-3-enoic acid and 2-(4-fluorophenyl)-2,2-dimethyl-ethylamine analogously to the procedure described for intermediate X-1. $^1$H-NMR (400 MHz, CDCl$_3$) δ 1.40 (s, 6H), 3.08 (s, 2H), 6.91-6.99 (m, 3H), 7.06-7.11 (m, 2H), 7.38-7.47 (m, 3H), 7.65-7.70 (m, 2H), 7.82 (d, J=16, 1H), 7.92 (d, J=16, 1H).

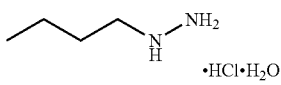

Intermediate XI-2

Step A: To a magnetically stirred solution of tert-butylcarbazate (47.5 gram, 359 mmol) in anhydrous acetonitrile (300 ml) was successively added DIPEA (Hünig's base) (37.6 ml, 216 mmol) and 1-bromobutane (19.3 ml, 180 mmol). The resulting mixture was reacted at 60° C. for 16 hours. The resulting mixture was allowed to attain room temperature and subsequently concentrated in vacuo and further purified by Sepacore chromatography (eluant: petroleum ether 40-60/ethylacetate=4/1 (v/v)) to give N'-butylhydrazine-carboxylic acid tert-butyl ester (intermediate XIII-1) (13.2 gram, 39%) as a pale yellow oil: $^1$H-NMR (400 MHz, CDCl$_3$) δ 0.91 (t, J=7, 3H), 1.30-1.49 (m, 13H), 2.81-2.87 (m, 2H), 4.00 (br s, 1H), 6.20 (br s, 1H).

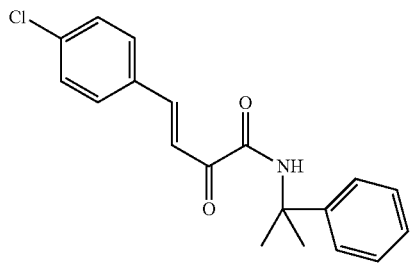

Intermediate X-5

Intermediate X-5 (E-2-oxo-4-(4-chlorophenyl)-but-3-enoic acid [1-phenyl-1-methyl-ethyl]amide was obtained from E-2-oxo-4-(4-chlorophenyl)-but-3-enoic acid and 1-phenyl-1-methyl-ethylamine analogously to the procedure described for intermediate X-1. $^1$H-NMR (400 MHz, CDCl$_3$) δ 1.79 (s, 6H), 7.23-7.28 (m, 1H), 7.32-7.43 (m, 6H), 7.51-7.57 (m, 3H), 7.71 (d, J=16 Hz, 1H), 7.85 (d, J=16 Hz, 1H).

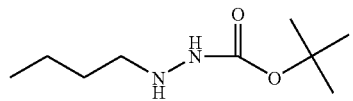

Intermediate XIII-1

Step B: To a magnetically stirred solution of N'-butylhydrazine-carboxylic acid tert-butyl ester (intermediate XIII-1) (13.17 gram, 70 mmol) in 1,4-dioxane (100 ml) was added excess (12 mol equivalents) hydrochloric acid (12 N) and the resulting mixture was reacted for 16 hours at room temperature. The resulting mixture was concentrated in vacuo and triturated with diethyl ether to give n-butylhydrazine.HCl.H$_2$O (Intermediate XI-2) (9.63 gram, 92% yield). $^1$H-NMR (400 MHz, DMSO-d$_6$/CDCl$_3$=4/1 (v/v)) δ 0.93 (t, J=7, 3H), 1.32-1.43 (m, 2H), 1.56-1.65 (m, 2H), 2.92-2.98 (m, 2H), 7.20 (br s, ~6H).

Intermediate XI-3

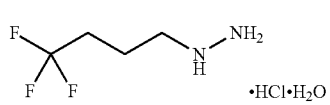

Step A: Intermediate (XI-3) was obtained analogously to the procedure described for intermediate (XI-2) from tert-butylcarbazate and 1-bromo-4,4,4-trifluorobutane via N'-(4,4,4-trifluorobutyl)hydrazine-carboxylic acid tert-butyl ester (intermediate XIII-2): Intermediate XIII-2: $^1$H-NMR (400 MHz, CDCl$_3$) δ 1.46 (s, 9H), 1.67-1.76 (m, 2H), 2.10-2.24 (m, 2H), 2.87-2.94 (m, 2H), 3.97 (br s, 1H), 6.05 (br s, 1H).

Intermediate XIII-2

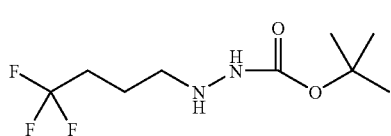

Step B: N'-(4,4,4-trifluorobutyl)hydrazine-carboxylic acid tert-butyl ester (intermediate XIII-2) was converted with excess hydrochloric acid to intermediate (XI-3) (4,4,4-trifluorobutylhydrazine.HCl.H$_2$O) analogously as described for the preparation of intermediate XI-2 (part B). Intermediate (XI-3): $^1$H-NMR (400 MHz, DMSO-d$_6$ δ 1.77 (quintet, J=7.7 Hz, 2H), 2.28-2.43 (m, 2H), 2.94 (t, J=7.4 Hz, 2H), 7.95 (br s, ~3H).

Example 4

Synthesis of Specific Compounds

Compound 1

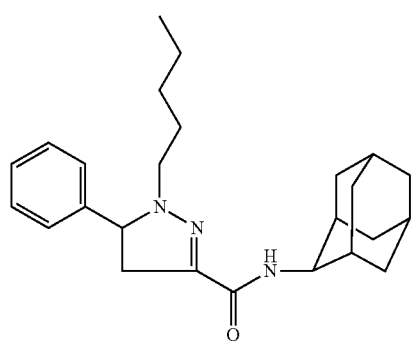

N-(Adamant-2-yl)-1-(n-pentyl)-5-phenyl-4,5-dihydro-(1H)-pyrazole-3-carboxamide

To a magnetically stirred solution of 1-(n-pentyl)-5-phenyl-4,5-dihydro-(1H)-pyrazole-3-carboxylic acid (Intermediate (VI-1) (0.70 g, 2.55 mmol) in dichloromethane (40 ml) was successively added 2-adamantanamine.HCl (480 mg, 2.55 mmol), N-ethyldiisopropylamine (DIPEA) (1.78 ml, 10.22 mmol) and 2-chloro-1,3-dimethylimidazolinium hexafluorophosphate (CIP) (853 mg, 3.07 mol) and the resulting mixture was reacted at room temperature for 16 hours in a nitrogen atmosphere. The reaction mixture was successively washed twice with water, twice with aqueous citric acid (0.5 M), twice with NaHCO$_3$ (5% aqueous solution) and brine, and subsequently dried over Na$_2$SO$_4$, filtered and concentrated in vacuo to give crude N-(adamant-2-yl)-1-(n-pentyl)-5-phenyl-4,5-dihydro-(1H)-pyrazole-3-carboxamide (1.26 g) as an orange oil. Further chromatographic purification using Sepacore equipment (eluant: petroleum ether/diethyl ether=85/15 (v/v)) gave compound 1 (750 mg, 67% yield) as an oil. $^1$H-NMR (400 MHz, CDCl$_3$) δ 0.85 (t, J=7, 3H), 1.21-1.30 (m, 4H), 1.55-1.65 (m, 2H), 1.65-1.70 (m, 2H), 1.76 (br s, 2H), 1.75-1.92 (m, 8H), 1.97-2.01 (m, 2H), 2.82 (dd, J=17 and 14, 1H), 2.92-2.97 (m, 2H), 3.42 (dd, J=17 and 11, 1H), 4.09-4.14 (m, 1H), 4.40 (dd, J=14 and 11, 1H), 6.99-7.07 (m, 1H), 7.28-7.38 (m, 5H).

Compounds 2-100 were analogously prepared.

Compound 2

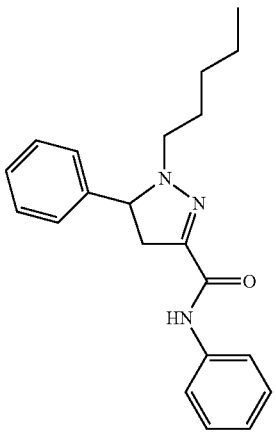

N-Phenyl-1-(n-pentyl)-5-phenyl-4,5-dihydro-(1H)-pyrazole-3-carboxamide $^1$H-NMR (400 MHz, CDCl$_3$) δ 0.87 (t, J=7 Hz, 3H), 1.17-1.34 (m, 4H), 1.55-1.73 (m, 2H), 2.85-3.08 (m, 3H), 3.49 (dd, J=17 and 11.4 Hz, 1H), 4.53 (dd, J=14 and 11.4 Hz, 1H), 7.09 (t, J=7.5 Hz, 1H), 7.28-7.42 (m, 7H), 7.62 (d, J=7.5 Hz, 2H), 8.43 (s, 1H).

Compound 3

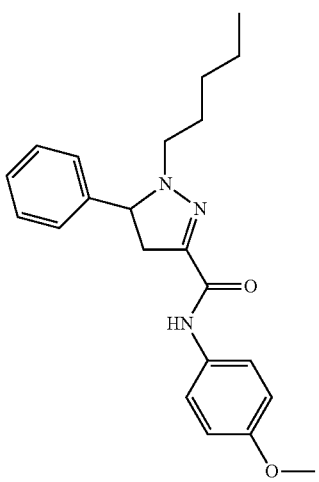

N-(4-Methoxyphenyl)-1-(n-pentyl)-5-phenyl-4,5-dihydro-(1H)-pyrazole-3-carboxamide $^1$H-NMR (400 MHz, CDCl$_3$) δ 0.86 (t, J=6.9 Hz, 3H), 1.19-1.34 (m, 4H) 1.57-1.69 (m, 2H), 2.85-3.06 (m, 3H), 3.48 (dd, J=17 and 11 Hz, 1H), 3.80 (s, 3H), 4.50 (dd, J=14 and 11.4 Hz, 1H), 6.88 (d, J=9 Hz, 2H), 7.28-7.40 (m, 5H) 7.54 (d, J=9 Hz, 2H), 8.35 (br s, 1 H).

Compound 5

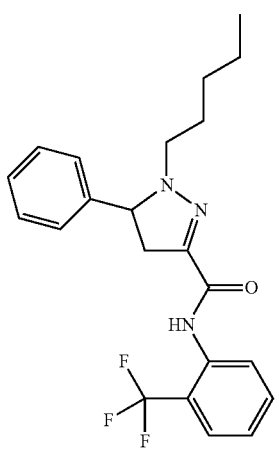

N-(2-Trifluoromethyl)phenyl-1-(n-pentyl)-5-phenyl-4,5-dihydro-(1H)-pyrazole-3-carboxamide $^1$H-NMR (400 MHz, CDCl$_3$) δ 0.88 (t, J=7.2 Hz, 3H), 1.18-1.38 (m, 4H), 1.61-1.70 (m, 2H), 2.86-3.11 (m, 3H), 3.49 (dd, J=17 and 11.7 Hz, 1H), 4.59 (dd, J=14 and 11.4 Hz, 1H), 7.17 (t, J=7.7 Hz, 1H), 7.29-7.42 (m, 5H), 7.55 (t, J=7.8 Hz, 1H), 7.61 (d, J=7.8 Hz, 1H), 8.45 (d, J=8.4 Hz, 1H), 9.05 (br s, 1H).

Compound 4

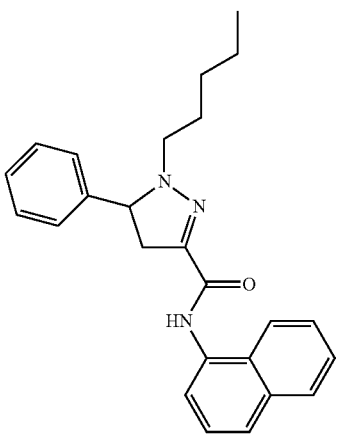

N-(Napht-1-yl)-1-(n-pentyl)-5-phenyl-4,5-dihydro-(1H)-pyrazole-3-carboxamide $^1$H-NMR (400 MHz, CDCl$_3$) δ 0.86 (t, J=7 Hz, 3H), 1.20-1.40 (m, 4H), 1.66-1.77 (m, 2H), 2.92-3.14 (m, 3H), 3.55 (dd, J=17 and 11.4 Hz, 1 H), 4.59 (dd, J=14 and 11.4 Hz, 1H), 7.30-7.44 (m, 5H), 7.46-7.61 (m, 3H), 7.67 (d, J=8.4 Hz, 1H), 7.88 (d, J=7.5 Hz, 1H), 7.95 (d, J=8.4 Hz, 1H), 8.20 (d, J=7.5 Hz, 1H), 9.05 (br s, 1H).

Compound 6

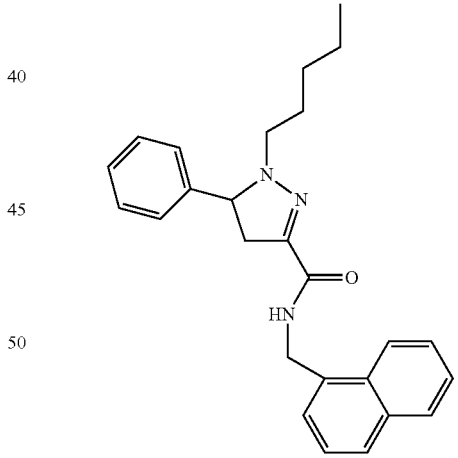

N-(Naphthalen-1-ylmethyl)-1-(n-pentyl)-5-phenyl-4,5-dihydro-(1H)-pyrazole-3-carboxamide $^1$H-NMR (400 MHz, CDCl$_3$) δ 0.79 (t, J=6.9 Hz, 3H), 1.07-1.25 (m, 4H), 1.44-1.58 (m, 2H), 2.78-2.92 (m, 3H), 3.46 (dd, J=17.3, and 11.3 Hz, 1H), 4.41 (dd, J=14.3 and 11.3 Hz, 1H), 5.00 (d, J=5.7 Hz, 2H), 6.90 (br t, J=5.6 Hz, 1H), 7.27-7.37 (m, 5H), 7.42-7.60 (m, 4H), 7.83 (d, J=7.8 Hz, 1H), 7.88 (d, J=1.2 Hz, 1H), 8.10 (d, J=8.1 Hz, 1H).

Compound 7

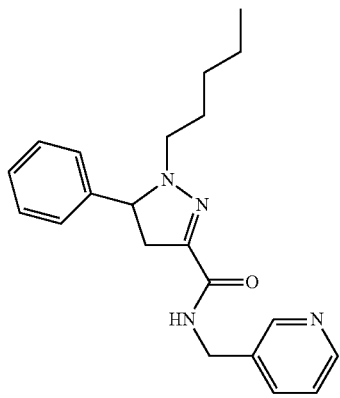

N-(Pyridin-3-ylmethyl)-1-(n-pentyl)-5-phenyl-4,5-dihydro-(1H)-pyrazole-3-carboxamide $^1$H-NMR (400 MHz, CDCl$_3$) δ 0.83 (t, J=6.9 Hz, 3H), 1.14-1.30 (m, 4H), 1.51-1.64 (m, 2H), 2.81-2.99 (m, 3H), 3.44 (dd, J=17.3 and 11.3 Hz, 1H), 4.45 (dd, J=14.30 and 11.29 Hz, 1H), 4.56 (d, J=6.3 Hz, 2H), 7.00 (br t, J=5.9 Hz, 1H), 7.26-7.39 (m, 6H), 7.70 (br d, J=7.8 Hz, 1H), 8.54 (dd, J=4.8 and 1.50 Hz, 1H), 8.60 (d, 1H).

Compound 9

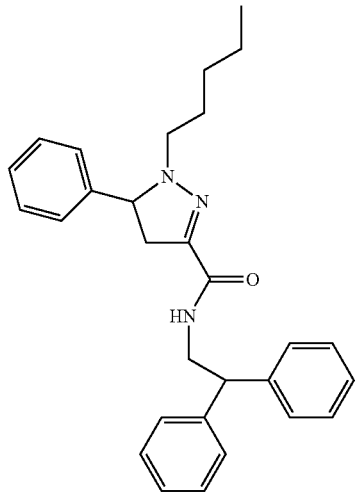

N-(2,2-diphenylethyl)-1-(n-pentyl)-5-phenyl-4,5-dihydro-(1H)-pyrazole-3-carboxamide $^1$H-NMR (400 MHz, CDCl$_3$) δ 0.83 (t, J=7.07 Hz, 3H), 1.09-1.28 (m, 4H), 1.43-1.58 m, 2H), 2.73-2.91 (m, 3H), 3.37 (dd, J=17.2 and 11.1 Hz, 1H), 3.98 (dd, J=7.8 and 6.2 Hz, 2H), 4.26 (t, J=7.8 Hz, 1H), 4.36 (dd, J=14.3 and 11.3 Hz, 1H), 6.62 (br t, J=5.9 Hz, 1H), 7.18-7.37 (m, 15H).

Compound 8

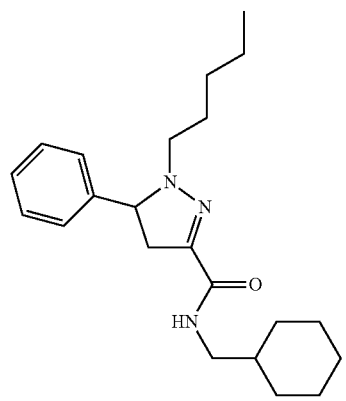

N-(Cyclohexylmethyl)-1-(n-pentyl)-5-phenyl-4,5-dihydro-(1H)-pyrazole-3-carboxamide $^1$H-NMR (400 MHz, CDCl$_3$) δ 0.85 (t, J=6.9 Hz, 3H), 0.90-1.04 (m, 2H), 1.12-1.33 (m, 7H), 1.47-1.82 (m, 8H), 2.76-2.98 (m, 3H), 3.18 (dq, J=12.9 and 6.6 Hz, 2H), 3.41 (dd, J=17.3 and 11 Hz, 1H), 4.39 (dd, J=14.3 and 11 Hz, 1H), 6.68 (br t, J=5.9 Hz, 1H), 7.27-7.41 (m, 5H).

Compound 10

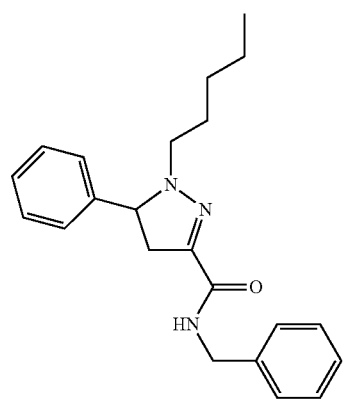

N-(Benzyl)-1-(n-pentyl)-5-phenyl-4,5-dihydro-(1H)-pyrazole-3-carboxamide $^1$H-NMR (400 MHz, CDCl$_3$) δ 0.83 (t, J=6.9 Hz, 3H), 1.13-1.29 (m, 4H), 1.49-1.64 (m, 2H), 2.81-2.96 (m, 3H), 3.44 (dd, J=17.3 and 11.3 Hz, 1H), 4.42 (dd, J=14.5 and 11.1 Hz, 1H), 4.54 (d, J=6 Hz, 2H), 6.94 (br t, J=5.7 Hz, 1H), 7.26-7.40 (m, 10H).

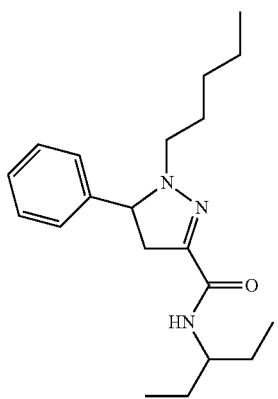

Compound 11

N-[(1-Ethyl)propyl]-1-(n-pentyl)-5-phenyl-4,5-dihydro-(1H)-pyrazole-3-carboxamide ¹H-NMR (400 MHz, CDCl₃) δ 0.85 (t, J=6.9 Hz, 3H), 0.94 (t, J=7, 6H), 1.17-1.31 (m, 4H), 1.39-1.52 (m, 2H), 1.53-1.69 (m, 4H), 2.78-2.98 (m, 3H), 3.42 (dd, J=17.3 and 11 Hz, 1H), 3.79-3.90 (m, 1H), 4.40 (dd, J=14.4 and 11.1 Hz, 1H), 6.35 (d, J=9.3 Hz, 1H), 7.27-7.40 (m, 5H).

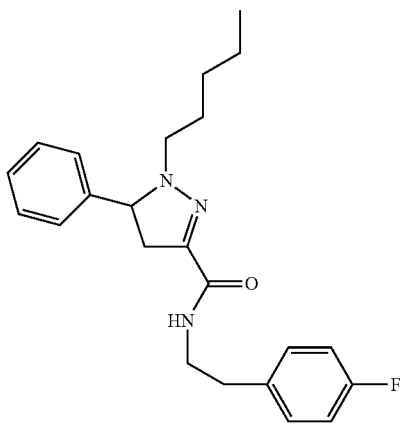

Compound 13

N-[2-(4-Fluorophenyl)ethyl]-1-(n-pentyl)-5-phenyl-4,5-dihydro-(1H)-pyrazole-3-carboxamide ¹H-NMR (400 MHz, CDCl₃) δ 0.85 (t, J=6.9 Hz, 3H), 1.15-1.31 (m, 4H), 1.51-1.65 (m, 2H), 2.78-2.97 (m, 5H), 3.41 (dd, J=17.1 and 11.1 Hz, 1H), 3.52-3.60 (m, 2H), 4.41 (dd, J=14.3 and 11.3 Hz, 1H), 6.69 (br t, J=5.9 Hz, 1H), 7.00 (br t, J=8.7 Hz, 2H), 7.19 (dd, J=8.4 and 5.4 Hz, 2H), 7.27-7.40 (m, 5H).

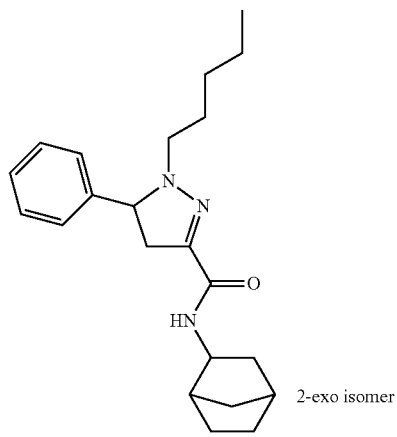

Compound 12

2-exo isomer

N-(Exo-bicyclo[2.2.1]hept-2-yl)-1-(n-pentyl)-5-phenyl-4,5-dihydro-(1H)-pyrazole-3-carboxamide (diastereomeric mixture)

¹H-NMR (400 MHz, CDCl₃) δ 0.85 (d, J=6.9 Hz, 3H), 1.10-1.65 (m, 13H), 1.83 (ddd, J=13.1 and 8 and 2.1 Hz, 1H), 2.25-2.34 (m, 2H), 2.76-2.97 (m, 3H), 3.40-3.41 (2x dd, J=18.4 and 11.1 Hz, 1H), 3.79 (br td, J=7.7 and 3.6 Hz, 1H), 4.37-4.38 (2x dd, J=14.4 and 11.1 and 3.3 Hz, 1H), 6.46 (br d, J=7.2 Hz, 1H), 7.27-7.40 (m, 5H).

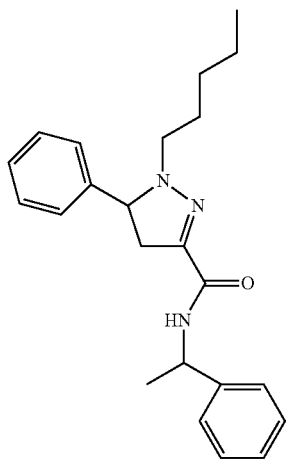

Compound 14

N-(1-Phenyl-ethyl)-1-(n-pentyl)-5-phenyl-4,5-dihydro-(1H)-pyrazole-3-carboxamide (1:1 diastereomeric mixture)

¹H-NMR (400 MHz, CDCl₃) δ 0.84 (t, J=6.5 Hz, 3H), 1.15-1.30 (m, 4H), 1.48-1.67 (m, 5H), 2.76-2.96 (m, 3H), 3.39-3.40 (2 x dd, J=17.4 and 11.1, 1H), 4.39-4.40 (2 x dd, J=14.3 and 11.1 Hz, 1H), 5.14-5.25 (m, 1H), 6.86 (br d, J=8.1 Hz, 1H), 7.26-7.41 (m, 10H).

Compound 15

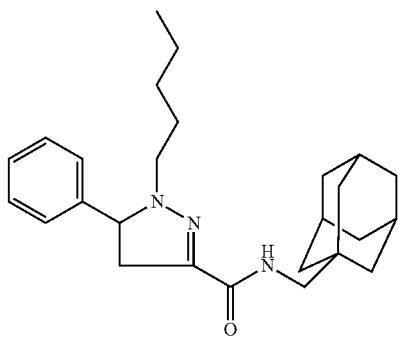

N-(Adamantylmethyl)-1-(n-pentyl)-5-phenyl-4,5-dihydro-(1H)-pyrazole-3-carboxamide $^1$H-NMR (400 MHz, CDCl$_3$) δ 0.85 (t, J=6.9 Hz, 3H), 1.18-1.32 (m, 4H), 1.49-1.78 (m, 14H), 2.00 (br s, 3H), 2.78-3.11 (m, 5H), 3.42 (dd, J=17.1 and 11.1 Hz, 1H), 4.40 (dd, J=14.4 and 11.1 Hz, 1H), 6.69 (br t, J=6.3 Hz, 1H), 7.26-7.40 (m, 5H).

Compound 16

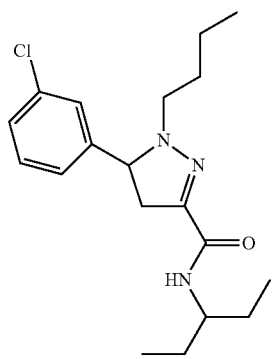

N-[(1-Ethyl)propyl]-1-(n-butyl)-5-(3-chlorophenyl)-4,5-dihydro-(1H)-pyrazole-3-carboxamide $^1$H-NMR (400 MHz, CDCl$_3$) δ 0.87 (t, J=7.4 Hz, 3H), 0.94 (t, J=7.4 Hz, 6H), 1.19-1.70 (m, 8H), 2.79 (dd, J=17.3 and 14.3 Hz, 1H), 2.89-2.95 (m, 2H), 3.43 (dd, J=17.4 and 11.1 Hz, 1H), 3.79-3.90 (m, 1H), 4.36 (dd, J=14.4 and 11.1 Hz, 1H), 6.33 (br d, J=9.3 Hz, 1H), 7.23-7.36 (m, 3H), 7.38 (br s, 1H).

Compound 17

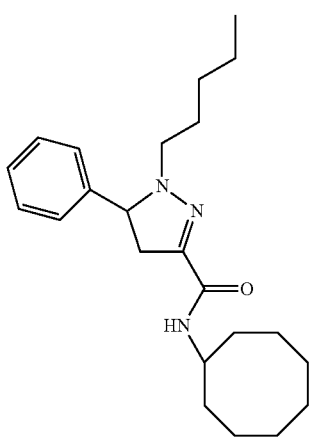

N-(Cyclooctyl)-1-(n-pentyl)-5-phenyl-4,5-dihydro-(1H)-pyrazole-3-carboxamide $^1$H-NMR (400 MHz, CDCl$_3$) δ 0.85 (t, J=6.92 Hz, 3H), 1.16-1.31 (m, 4H), 1.48-1.75 (m, 14H), 1.82-1.94 (m, 2H), 2.76-2.97 (m, 3H), 3.40 (dd, J=17.4 and 11.1 Hz, 1H), 4.00-4.10 (m, 1H), 4.37 (dd, J=14.3 and 11 Hz, 1H), 6.58 (br d, J=8.4 Hz, 1H), 7.27-7.39 (m, 5H).

Compound 18

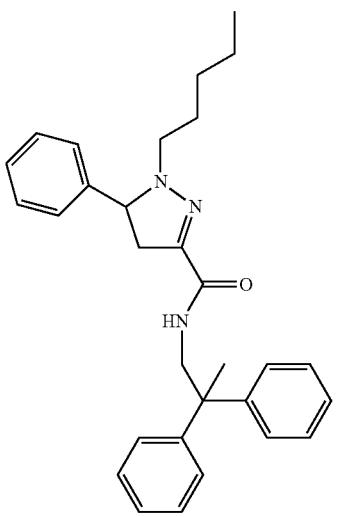

N-(2,2-diphenylpropyl)-1-(n-pentyl)-5-phenyl-4,5-dihydro-(1H)-pyrazole-3-carboxamide $^1$H-NMR (400 MHz, CDCl$_3$) δ 0.85 (t, J=7.1 Hz, 3H), 1.10-1.28 (m, 4H), 1.44-1.55 (m, 2H), 1.71 (s, 3H), 2.71-2.87 (m, 3H), 3.37 (dd, J=17.1 and 11.1 Hz, 1H), 4.02 (d, J=6.3 Hz, 2H), 4.34 (dd, J=14.4 and 11.1 Hz, 1H), 6.41 (br t, J=5.87 Hz, 1H), 7.19-7.37 (m, 15H).

Compound 19

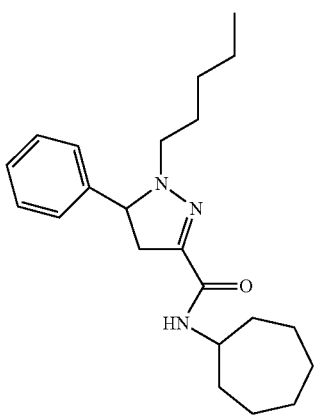

N-(Cycloheptyl)-1-(n-pentyl)-5-phenyl-4,5-dihydro-(1H)-pyrazole-3-carboxamide $^1$H-NMR (400 MHz, CDCl$_3$) δ 0.85 (t, J=6.9 Hz, 3H), 1.15-1.31 (m, 4H), 1.45-1.72 (m, 12H), 1.91-2.03 (m, 2H), 2.76-2.97 (m, 3H), 3.40 (dd, J=17.1 and 11.1 Hz, 1H), 3.95-

4.08 (m, 1H), 4.38 (dd, J=14.3 and 11 Hz, 1H), 6.57 (br d, J=8.4 Hz, 1H), 7.27-7.40 (m, 5H).

2.76-2.98 (m, 4H), 3.41 and 3.43 (2x dd, J=17.2 and 11.2 Hz, 1H), 4.42 (dd, J=14.1 and 11.1 Hz, 1H), 6.84 (br s, 1H), 7.15-7.39 (m, 10H).

Compound 20

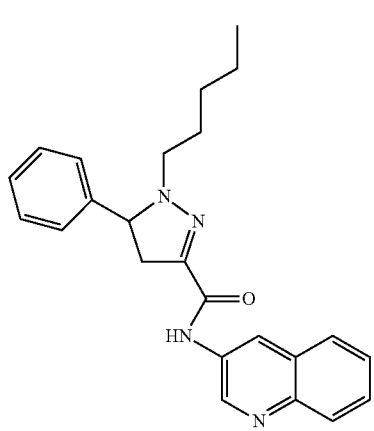

N-(Quinolin-3-yl)-1-(n-pentyl)-5-phenyl-4,5-dihydro-(1H)-pyrazole-3-carboxamide $^1$H-NMR (400 MHz, CDCl$_3$) δ 0.88 (t, J=6.92 Hz, 3H), 1.18-1.36 (m, 4H), 1.58-1.71 (m, 2H), 2.91-3.14 (m, 3H), 3.53 (dd, J=17.3 and 11.6 Hz, 1H), 4.62 (dd, J=13.8 and 11.7 Hz, 1H), 7.29-7.45 (m, 5H), 7.53 (br t, J=6.9 Hz, 1H), 7.62 (dt, J=7.7 and 1.50 Hz, 1H), 7.81 (d, J=7.5 Hz, 1H), 8.05 (d, J=8.4 Hz, 1H), 8.69 (s, 1H), 8.83 (d, J=2.4 Hz, 1H), 8.86 (d, J=2.7 Hz, 1H).

Compound 22

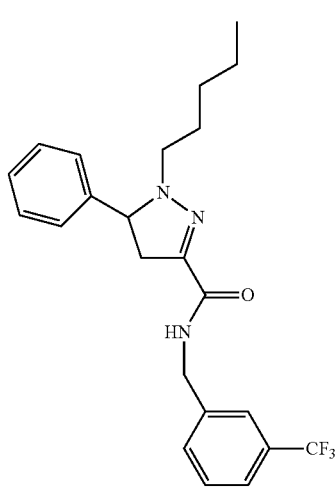

N-[3-(Trifluoromethyl)benzyl)]-1-(n-pentyl)-5-phenyl-4,5-dihydro-(1H)-pyrazole-3-carboxamide $^1$H-NMR (400 MHz, CDCl$_3$) δ 0.83 (t, J=6.92 Hz, 3H), 1.15-1.30 (m, 4H), 1.51-1.65 (m, 2H), 2.81-2.99 (m, 3H), 3.45 (dd, J=17.3 and 11.3 Hz, 1H), 4.46 (dd, J=14.4 and 11.4 Hz, 1H), 4.59 (s, 2H), 7.28-7.39 (m, 5H), 7.43-7.50 (m, 1H), 7.52-7.60 (m, 3H).

Compound 21

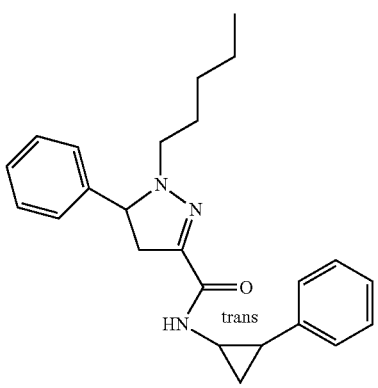

N-(2-phenyl-trans-cyclopropyl)-1-(n-pentyl)-5-phenyl-4,5-dihydro-(1H)-pyrazole-3-carboxamide (diastereomeric mixture)

$^1$H-NMR (400 MHz, CDCl$_3$) δ 0.85 (t, J=6.92 Hz, 3H), 1.15-1.33 (m, 6H), 1.52-1.68 (m, 2H), 2.11-2.19 (m, 1H),

Compound 23

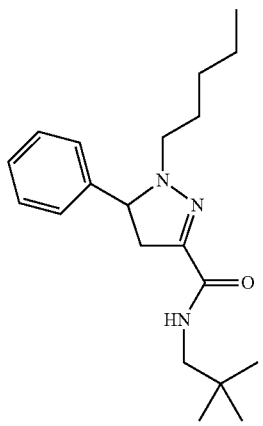

N-(2,2-Dimethylpropyl)-1-(n-pentyl)-5-phenyl-4,5-dihydro-(1H)-pyrazole-3-carboxamide $^1$H-NMR (400 MHz, CDCl$_3$) δ 0.85 (t, J=7.22 Hz, 3H), 0.96 (s, 9H), 1.16-1.32 (m, 4H), 1.53-1.67 (m, 2H), 2.77-2.97 (m, 3H), 3.15 (dd, J=6.6 and 1.8 Hz, 2H), 3.42 (dd, J=17.5 and 11.1 Hz, 1H), 4.41 (dd, J=14.4 and 11.1 Hz, 1H), 6.72 (br t, J=6.2 Hz, 1H), 7.27-7.40 (m, 5H).

Compound 24

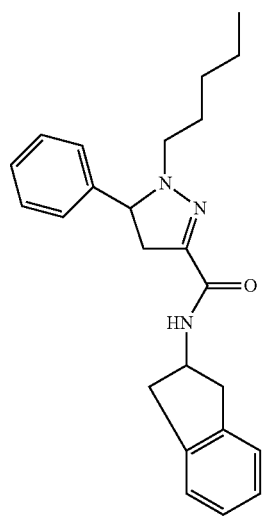

N-(2-Indanyl)-1-(n-pentyl)-5-phenyl-4,5-dihydro-(1H)-pyrazole-3-carboxamide

¹H-NMR (400 MHz, CDCl₃) δ 0.82 (t, J=6.9 Hz, 3H), 1.11-1.29 (m, 4H), 1.47-1.64 (m, 2H), 2.77-2.96 (m, 4H), 3.32-3.47 (m, 3H), 4.40 (dd, J=14.3 and 11.3 Hz, 1H), 4.76-4.87 (m, 1H), 6.80 (br d, J=7.8 Hz, 1H), 7.14-7.40 (m, 10H).

Compound 25

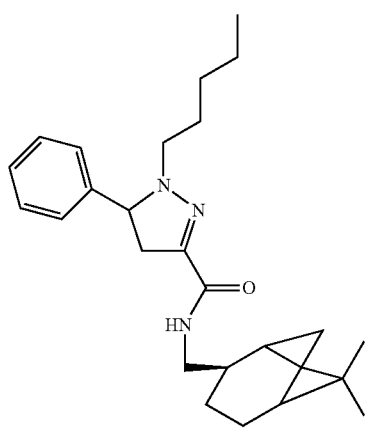

N-[(1R,2S,5R)-rel-6,6-dimethylbicyclo[3.1.1.]heptan-2-methyl]-1-(n-pentyl)-5-phenyl-4,5-dihydro-(1H)-pyrazole-3-carboxamide (diastereomeric mixture) (from (−)-cis-myrtanylamine (CAS 38235-68-6))

¹H-NMR (400 MHz, CDCl₃) δ 0.80-0.90 (m, 3H), 0.91 (d, J=9.6 Hz, 1H), 1.07 (s, 3H), 1.17-1.32 (m, 7H), 1.47-1.67 (m, 3H), 1.81-2.04 (m, 5H), 2.27-2.42 (m, 2H), 2.77-2.98 (m, 3H), 3.27-3.49 (m, 3H), 4.39 (dd, J=14.4 and 11.1 Hz, 1H), 6.64 (br t, J=5.7 Hz, 1H), 7.27-7.39 (m, 5H).

Compound 26

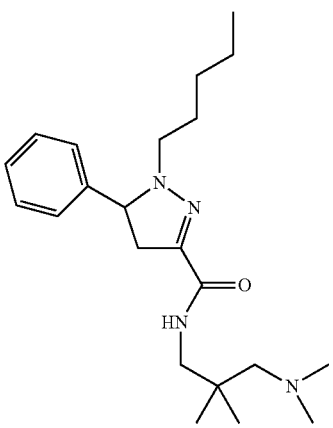

N-[(3-Dimethylamino)-2,2-dimethylpropyl]-1-(n-pentyl)-5-phenyl-4,5-dihydro-(1H)-pyrazole-3-carboxamide ¹H-NMR (400 MHz, CDCl₃) δ 0.85 (t, J=6.92 Hz, 3H), 0.94 (s, 3H), 0.95 (s, 3H), 1.17-1.34 (m, 4H), 1.58-1.70 (m, 2H), 2.26 (s, 2H), 2.33 (s, 6H), 2.78-2.94 (m, 3H), 3.24 (d, J=5.4 Hz, 2H), 3.40 (dd, J=17.1 and 10.8 Hz, 1H), 4.35 (dd, J=14.6 and 11 Hz, 1H), 7.28-7.41 (m, 5H), 8.58 (br s, 1H).

Compound 27

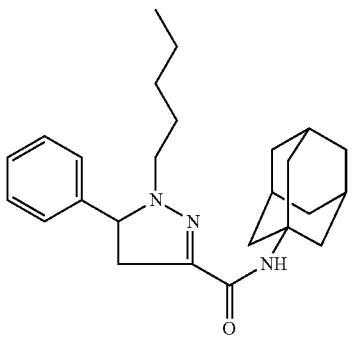

N-(Adamantyl)-1-(n-pentyl)-5-phenyl-4,5-dihydro-(1H)-pyrazole-3-carboxamide

¹H-NMR (400 MHz, CDCl₃) δ 0.84 (t, J=6.92 Hz, 3H), 1.15-1.32 (m, 4H) 1.49-1.64 (m, 2H), 1.65-1.76 (m, 7H), 2.08 (br s, 8H), 2.78 (dd, J=17.1 and 14.4 Hz, 1H), 2.89 (t, J=7.5 Hz, 2H), 3.37 (dd, J=17.3 and 11 Hz, 1H) 4.35 (dd, J=14.6 and 11 Hz, 1H), 6.40 (br s, 1H), 7.27-7.41 (m, 5H).

Compound 28

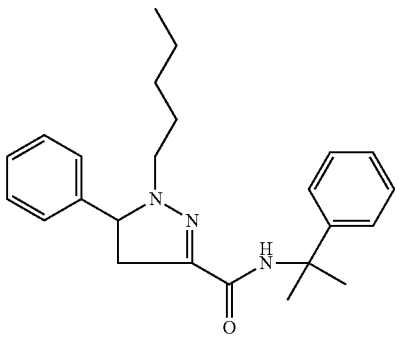

N-(1-Phenyl-1-methyl-ethyl)-1-(n-pentyl)-5-phenyl-4,5-dihydro-(1H)-pyrazole-3-carboxamide $^1$H-NMR (400 MHz, CDCl$_3$) δ 0.85 (t, J=6.9 Hz, 3H), 1.16-1.33 (m, 4H), 1.51-1.69 (m, 2H), 1.75 (s, 3H), 1.77 (s, 3H), 2.78 (dd, J=17.3 and 14.6 Hz, 1H), 2.92 (br t, J=7.1 Hz, 2H), 3.35 (dd, J=17.3 and 11 Hz, 1H), 4.38 (dd, J=14.4 and 11.1 Hz, 1H), 6.97 (br s, 1H), 7.19-7.24 (m, 1H), 7.27-7.41 (m, 7H), 7.45 (br d, J=7.2 Hz, 2H).

Compound 29

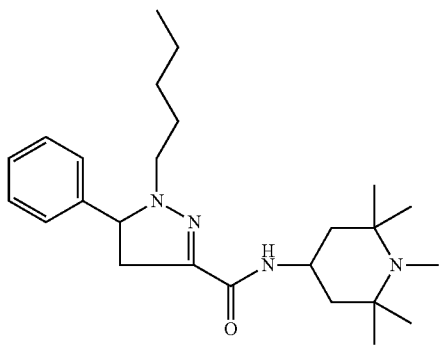

N-(N,2,2,6,6-pentamethylpiperidin-4-yl)-1-(n-pentyl)-5-phenyl-4,5-dihydro-(1H)-pyrazole-3-carboxamide $^1$H-NMR (400 MHz, CDCl$_3$) δ 0.85 (t, J=7.1 Hz, 3H), 1.10 (s, 6H), 1.16 (s, 6H), 1.19-1.30 (m, 4H), 1.37 (br t, J=11.4 Hz, 2H), 1.50-1.68 (m, 2H), 1.86 (dd, J=12.3 and 3.3 Hz, 2H), 2.26 (s, 3H), 2.81 (dd, J=17.5 and 14.4 Hz, 1H), 2.86-2.97 (m, 2H), 3.40 (dd, J=17.1 and 11.1 Hz, 1H), 4.14-4.30 (m, 1H), 4.39 (dd, J=14.4 and 11.1 Hz, 1H), 6.39 (br d, J=8.1 Hz, 1H), 7.27-7.40 (m, 5H).

Compound 30

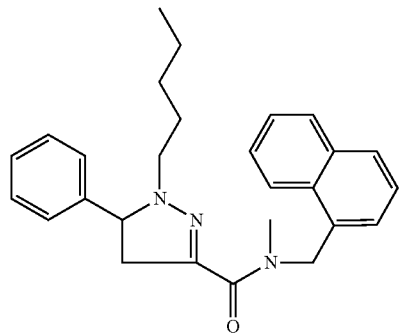

N-Methyl-N-(Naphthalen-1-yl-methyl)-1-(n-pentyl)-5-phenyl-4,5-dihydro-(1H)-pyrazole-3-carboxamide $^1$H-NMR (400 MHz, CDCl$_3$) (broad signals due to restricted amide bond rotation) δ 0.56-1.78 (m, 9H), 2.48-3.08 (m, 3H), 3.10 (br s) and 3.26 (br s: Together integrates for 3H), 3.40-3.59 (m, 1H), 4.15-4.40 (m, 1H), 5.18 (br s) and 5.50 (br d, J=16 Hz) and 5.64 (br d, J=16 Hz; Together integrates for 2H), 7.26-7.58 (m, 9H), 7.80 (br s, 1H), 7.88 (br d, J=7 Hz, 1H), 7.92-8.17 (m, 1H), Compound 31

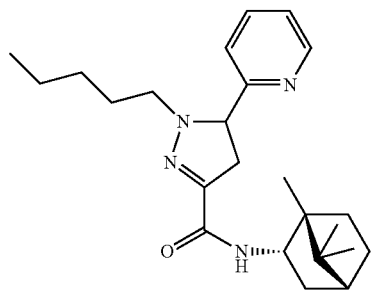

N-[endo-(1R,2S,4R)-1,7,7-trimethylbicyclo[2.2.1]hept-2-yl]-1-(n-pentyl)-5-(pyrid-2-yl)-4,5-dihydro-(1H)-pyrazole-3-carboxamide (diastereomeric mixture)

$^1$H-NMR (400 MHz, DMSO-d$_6$) δ 0.81-0.95 (m, 10H), 0.97 (s, 3H), 1.16-1.35 (m, 4H), 1.35-1.66 (m, 5H), 1.69 (t, J=4.4 Hz, 1H), 1.74-1.87 (m, 1H), 2.32-2.44 (m, 1H), 2.91-3.11 (m, 3H), 3.44-3.59 (m, 1H), 4.24-4.35 (m, 1H), 4.54-4.67 (m, 1H), 6.69 (br d, J=8.4 Hz, 1H), 7.20-7.27 (m, 1H), 7.46 (dd, J=7.8 and 4.5 Hz, 1H), 7.72 (br t, J=7.5 Hz, 1H), 8.58 (br t, J=4 Hz, 1H).

Compound 32

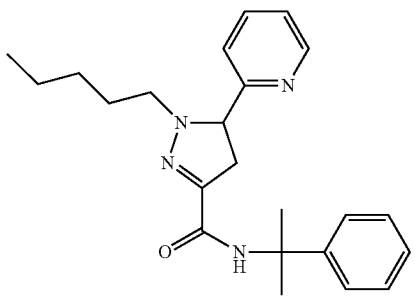

N-(1-Phenyl-1-methyl-ethyl)-1-(n-pentyl)-5-(pyrid-2-yl)-4,5-dihydro-(1H)-pyrazole-3-carboxamide $^1$H-NMR (400 MHz, DMSO-d$_6$) δ 0.84 (t, J=6.9 Hz, 3H), 1.17-1.31 (m, 4H), 1.52-1.65 (m, 2H), 1.73 (s, 3H), 1.75 (s, 3H), 2.88-3.10 (m, 3H), 3.40 (dd, J=17.3 and 11.6 Hz, 1H), 4.59 (dd, J=13.67 and 11.6 Hz, 1H), 7.02 (br s, 1H), 7.19-7.28 (m, 2H), 7.33 (br t, J=7.7 Hz, 2H), 7.40-7.48 (m, 3H), 7.74 (dt, J=7.7 and 1.8 Hz, 1H), 8.57 (br d, J=3.9 Hz, 1H).

Compound 33

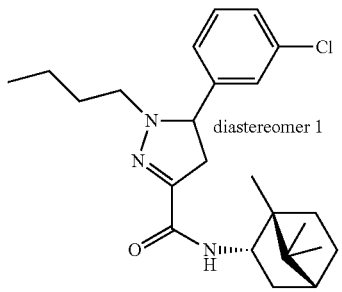

N-[endo-(1R,2S,4R)-1,7,7-trimethylbicyclo[2.2.1]hept-2-yl]-1-(n-butyl)-5-(3-chlorophenyl)-4,5-dihydro-(1H)-pyrazole-3-carboxamide (diastereomer 1)

Compounds 33 and 34 were separated from the corresponding diastereomeric mixture by flash chromatography (silicagel). Eluant: petroleum ether (40-60)/diethyl ether=4/1 v/v.

$^1$H-NMR (400 MHz, CDCl$_3$) δ 0.81-0.95 (m, 10H), 0.97 (s, 3H), 1.20-1.48 (m, 4H), 1.52-1.63 (m, 3H), 1.69 (t, J=4.5 Hz, 1H), 1.74-1.86 (m, 1H), 2.32-2.43 (m, 1H), 2.78 (dd, J=17.4 and 14.1 Hz, 1H), 2.95 (t, J=7.4 Hz, 2H), 3.38-3.48 (m, 1H) 4.25-4.34 (m, 1H), 4.38 (dd, J=14.1 and 11.4 Hz, 1H), 6.66 (br d, J=9.3 Hz, 1H), 7.20-7.39 (m, 4H).

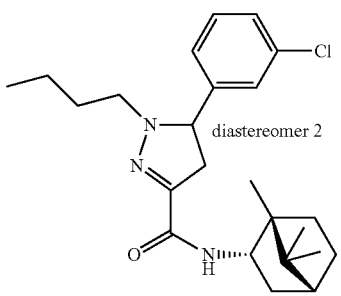

Compound 34

N-[endo-(1R,2S,4R)-1,7,7-trimethylbicyclo[2.2.1]hept-2-yl]-1-(n-butyl)-5-(3-chlorophenyl)-4,5-dihydro-(1H)-pyrazole-3-carboxamide (diastereomer 2)

$^1$H-NMR (400 MHz, CDCl$_3$) δ 0.82-0.95 (m, 10H), 0.97 (s, 3H), 1.21-1.47 (m, 4H) 1.51-1.65 (m, 3H), 1.69 (t, J=4.3 Hz, 1H), 1.75-1.86 (m, 1H), 2.33-2.43 (m, 1H), 2.79 (dd, J=17.3 and 14.3 Hz, 1H), 2.94 (t, J=7.2 Hz, 2H), 3.42 (dd, J=17.4 and 11.1 Hz, 1H), 4.26-4.41 (m, 2H), 6.65 (d, J=9 Hz, 1H), 7.23-7.31 (m, 3H), 7.39 (br s, 1H).

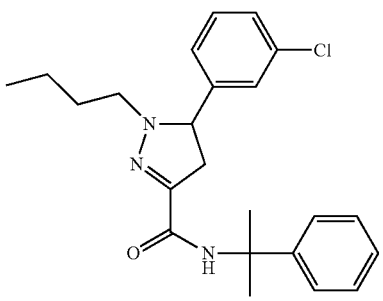

Compound 35

N-(1-Phenyl-1-methyl-ethyl)-1-(n-butyl)-5-(3-chlorophenyl)-4,5-dihydro-(1H)-pyrazole-3-carboxamide $^1$H-NMR (400 MHz, CDCl$_3$) δ 0.87 (t, J=7.4 Hz, 3H), 1.21-1.43 (m, 2H), 1.54-1.64 (m, 2H), 1.75 (s, 3H), 1.77 (s, 3H), 2.74 (dd, J=17.4 and 14.1 Hz, 1 H), 2.93 (t, J=7.3 Hz, 2H), 3.36 (dd, J=17.1 and 11.1 Hz, 1H), 4.35 (dd, J=14.3 and 11.3 Hz, 1H), 6.96 (br s, 1H), 7.21-7.30 (m, 4H), 7.31-7.38 (m, 3H), 7.45 (br d, J=8.1 Hz, 2H).

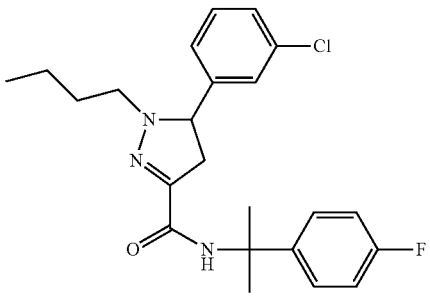

Compound 36

N-[1-(4-fluorophenyl)-1-methyl-ethyl]-1-(n-butyl)-5-(3-chlorophenyl)-4,5-dihydro-(1H)-pyrazole-3-carboxamide $^1$H-NMR (400 MHz, CDCl$_3$) δ 0.87 (t, J=7.4 Hz, 3H), 1.21-1.41 (m, 2H), 1.54-1.64 (m, 2H), 1.74 (s, 3H), 1.75 (s, 3H), 2.73 (dd, J=17.4 and 14.4 Hz, 1H), 2.93 (t, J=7.4 Hz, 2H), 3.35 (dd, J=17.3 and 11.3 Hz, 1H), 4.35 (dd, J=14.1 and 11.1 Hz, 1H), 6.93 (br s, 1H), 7.01 (br t, J=8.7 Hz, 2H), 7.21-7.31 (m, 3H), 7.36-7.44 (m, 3H).

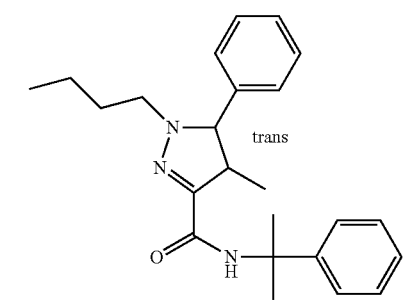

Compound 37

N-(1-Phenyl-1-methyl-ethyl)-1-(n-butyl)-trans-4-methyl-5-phenyl-4,5-dihydro-(1H)-pyrazole-3-carboxamide A Sepacore chromatographic purification was applied to purify the crude compound 37: Eluant: Dichloromethane.

$^1$H-NMR (400 MHz, CDCl$_3$) δ 0.86 (t, J=7.4 Hz, 3H), 1.19-1.38 (m, 5H), 1.51-1.61 (m, 2H), 1.74 (s, 3H), 1.77 (s, 3H), 2.89-2.97 (m, 2H), 3.14 (dq, J=13.4 and 6.7 Hz, 1H), 3.84 (d, J=13.2 Hz, 1H), 6.98 (br s, 1H), 7.23 (br t, J=7.4 Hz, 1H), 7.28-7.39 (m, 7H), 7.45 (br d, J=7.2 Hz, 2H).

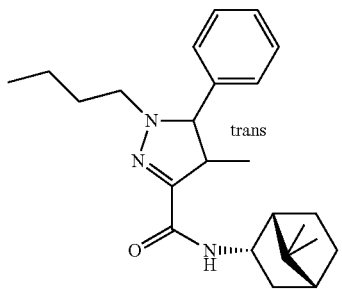

Compound 38

N-[endo-(1R,2S,4R)-1,7,7-trimethylbicyclo[2.2.1]hept-2-yl]-1-(n-butyl)-trans-4-methyl-5-phenyl-4,5-dihydro-(1H)-pyrazole-3-carboxamide (diastereomeric mixture)

Two successive Sepacore chromatographic purifications were applied to isolate compound 38 from the crude reaction mixture: Separation A: Eluant: petroleum ether (40-60)/diethyl ether=80/20. Separation B: Eluant: petroleum ether (40-60)/ethylacetate=90/10.

$^1$H-NMR (400 MHz, CDCl$_3$) δ 0.81-0.94 (m, 10H), 0.97 (s, 3H) 1.21-1.47 (m, 6H), 1.50-1.67 (m, 4H), 1.69 (t, J=4.5 Hz, 1H), 1.74-1.86 (m, 1H), 2.32-2.44 (m, 1H), 2.88-3.02 (m, 2H), 3.13-3.25 (m, 1H), 3.81-3.90 (m, 1H), 4.22-4.36 (m, 1H), 6.64-6.73 (m, 1H), 7.29-7.41 (m, 5H).

Compound 39

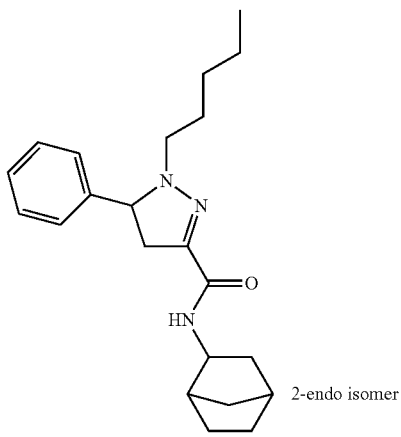

2-endo isomer

N-(Endo-bicyclo[2.2.1]hept-2-yl)-1-(n-pentyl)-5-phenyl-4,5-dihydro-(1H)-pyrazole-3-carboxamide (diastereomeric mixture)

$^1$H-NMR (400 MHz, CDCl$_3$) δ 0.85 (t, J=7.1 Hz, 3H), 1.16-1.38 (m, 7H), 1.40-1.68 (m, 6H), 2.06-2.17 (m, 1H), 2.24 (br s, 1H), 2.49 (br s, 1H), 2.82 (dd, J=16.5 and 14.4 Hz, 1H), 2.88-3.01 (m, 2H), 3.41 (dd, J=17.1 and 11.1 Hz, 1H), 4.13-4.24 (m, 1H), 4.35-4.47 (m, 1H), 6.60-6.73 (m, 1H), 7.28-7.43 (m, 5H).

Compounds 40-43

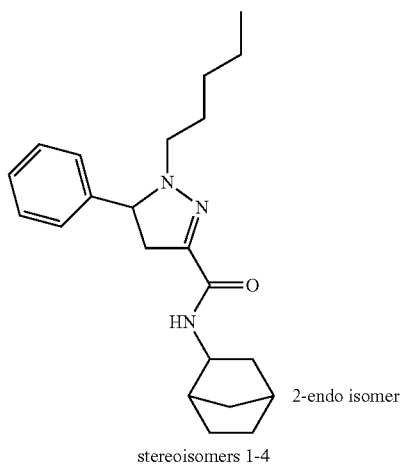

2-endo isomer
stereoisomers 1-4

Compound 12 was separated by preparative chiral HPLC into 4 separate stereoisomers (compounds 40, 41, 42 and 43, respectively).

N-(Exo-bicyclo[2.2.1]hept-2-yl)-1-(n-pentyl)-5-phenyl-4,5-dihydro-(1H)-pyrazole-3-carboxamide (compound 40) (stereoisomer 1; first eluting diastereomer; retention time=10.29 minutes; Diastereomeric excess=97%): [α$^{25}_D$]=+147°, c=0.9, methanol.

$^1$H-NMR (400 MHz, CDCl$_3$) δ 0.85 (t, J=7 Hz, 3H), 1.10-1.66 (m, 15H), 1.83 (ddd, J=13, 8 and 2.1 Hz, 1H), 2.25-2.33 (m, 2H), 2.81 (dd, J=17.3 and 14.3 Hz, 1H), 2.86-2.97 (m, 2H), 3.40 (dd, J=17.4 and 11.1 Hz, 1H), 3.79 (br td, J=7.6 and 3.4 Hz, 1H), 4.37 (dd, J=14.30 and 11 Hz, 1H), 6.45 (br d, J=7.5 Hz, 1H), 7.27-7.40 (m, 5H).

N-(Exo-bicyclo[2.2.1]hept-2-yl)-1-(n-pentyl)-5-phenyl-4,5-dihydro-(1H)-pyrazole-3-carboxamide (compound 41) (stereoisomer 2; second eluting diastereomer; retention time=12.57 minutes; Diastereomeric excess >99%): [α$^{25}_D$]=+158°, c=1.1, methanol.

$^1$H-NMR (400 MHz, CDCl$_3$) δ 0.85 (t, J=7 Hz, 3H), 1.11-1.65 (m, 15H), 1.83 (ddd, J=13, 8 and 2.1 Hz, 1H), 2.26-2.33 (m, 2H), 2.81 (dd, J=17.3 and 14.3 Hz, 1H), 2.86-2.98 (m, 2H), 3.40 (dd, J=17.4 and 11.1 Hz, 1H), 3.79 (br td, J=7.6 and 3.4 Hz, 1H), 4.38 (dd, J=14.4 and 11.1 Hz, 1H), 6.45 (br d, J=7.2 Hz, 1H), 7.27-7.38 (m, 5H).

N-(Exo-bicyclo[2.2.1]hept-2-yl)-1-(n-pentyl)-5-phenyl-4,5-dihydro-(1H)-pyrazole-3-carboxamide (compound 42) (stereoisomer 3; third eluting diastereomer; retention time=13.71 minutes; Diastereomeric excess >99%): [α$^{25}_D$]=−173°, c=1.0, methanol.

$^1$H-NMR (400 MHz, CDCl$_3$) δ 0.85 (t, J=7 Hz, 3H), 1.10-1.66 (m, 15H), 1.83 (ddd, J=13, 8 and 2.1 Hz, 1H), 2.24-2.34 (m, 2H), 2.81 (dd, J=17.3 and 14.3 Hz, 1H), 2.86-2.98 (m, 2H), 3.40 (dd, J=17.4 and 11.1 Hz, 1H), 3.79 (br td, J=7.6 and 3.4 Hz, 1H), 4.38 (dd, J=14.2 and 11.1 Hz, 1H), 6.45 (br d, J=7.5 Hz, 1H), 7.27-7.37 (m, 5H).

N-(Exo-bicyclo[2.2.1]hept-2-yl)-1-(n-pentyl)-5-phenyl-4,5-dihydro-(1H)-pyrazole-3-carboxamide (compound 43) (stereoisomer 4; fourth eluting diastereomer; retention time=23.01 minutes; Diastereomeric excess >99%): [α$^{25}_D$]=−162°, c=0.9, methanol.

$^1$H-NMR (400 MHz, CDCl$_3$) δ 0.85 (t, J=7 Hz, 3H), 1.10-1.66 (m, 15H), 1.83 (ddd, J=12.9, 8.1 and 2.1 Hz, 1H), 2.25-2.34 (m, 2H), 2.81 (dd, J=17.2 and 14.4 Hz, 1H), 2.85-2.98 (m, 2H), 3.40 (dd, J=17.2 and 11.1 Hz, 1H), 3.79 (br td, J=7.6 and 3.6 Hz, 1H), 4.37 (dd, J=14.2 and 11.1 Hz, 1H), 6.45 (br d, J=7.2 Hz, 1H), 7.27-7.40 (m, 5H).

Preparative chiral HPLC method: First step: A 250×30 mm column was used. Stationary phase: CHIRALPAK® AD=H 5 μm. n-Heptane/isopropanol=95/05 (v/v) was used as the mobile phase. Flow rate: 40 ml/minute. Temperature: 21.5° C. Detection UV 325 nm. Second step: A 250×30 mm column was used. Stationary phase: CHIRALPAK® IA 5 μm. n-Heptane/ethylacetate=85/15 (v/v) was used as the mobile phase. Flow rate: 40 ml/minute. Temperature: ambient. Detection UV 325 nm.

Analytical HPLC monitoring system: A 250×4.6 mm column was used. Stationary phase: CHIRALPAK® IA-H 5 μm. n-Heptane/ethylacetate=80/20 (v/v) was used as the mobile phase. Flow rate: 1 ml/minute. Temperature: 25° C. Detection: UV 300 nm.

Compound 44

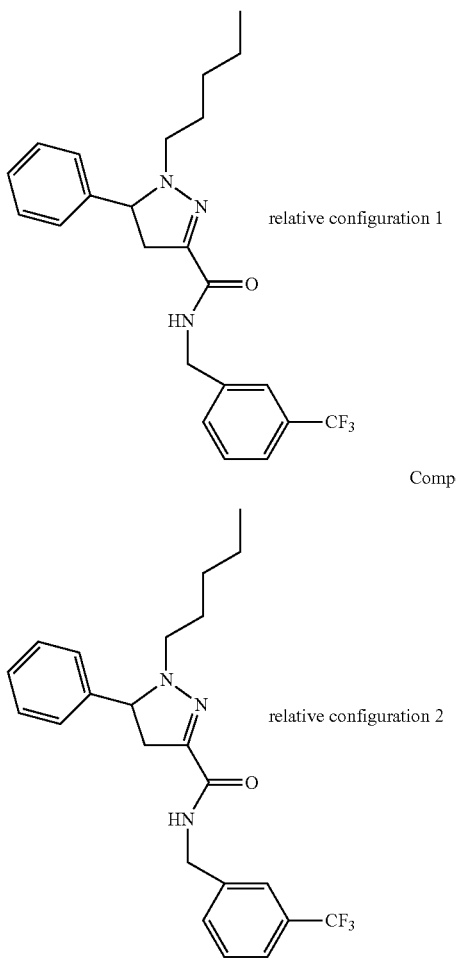

relative configuration 1

Compound 45 relative configuration 2

Racemic compound 22 (1.88 gram) was separated by preparative chiral HPLC into 2 separate enantiomers (compounds 44 and 45, respectively).

(+)-N-[3-(Trifluoromethyl)benzyl)]-1-(n-pentyl)-5-phenyl-4,5-dihydro-(1H)-pyrazole-3-carboxamide (compound 44)

$[\alpha^{25}_D]=124°$, c=1.0, methanol. $^1$H-NMR (400 MHz, CDCl$_3$) δ 0.83 (t, J=6.92 Hz, 3H), 1.15-1.30 (m, 4H), 1.51-1.65 (m, 2H), 2.81-2.99 (m, 3H), 3.45 (dd, J=17.3 and 11.3 Hz, 1H), 4.46 (dd, J=14.4 and 11.4 Hz, 1H), 4.59 (s, 2H), 7.28-7.39 (m, 5H), 7.43-7.50 (m, 1H), 7.52-7.60 (m, 3H). Enantiomeric excess: >98%.

(−)-N-[3-(Trifluoromethyl)benzyl)]-1-(n-pentyl)-5-phenyl-4,5-dihydro-(1H)-pyrazole-3-carboxamide (compound 45)

$[\alpha^{25}_D]=-132°$, c=0.8, methanol. $^1$H-NMR (400 MHz, CDCl$_3$) δ 0.83 (t, J=6.92 Hz, 3H), 1.15-1.30 (m, 4H), 1.51-1.65 (m, 2H), 2.81-2.99 (m, 3H), 3.45 (dd, J=17.3 and 11.3 Hz, 1H), 4.46 (dd, J=14.4 and 11.4 Hz, 1H), 4.59 (s, 2H), 7.28-7.39 (m, 5H), 7.43-7.50 (m, 1H), 7.52-7.60 (m, 3H). Enantiomeric excess: >98%.

Preparative chiral HPLC method: A 250×76 mm column was used. Stationary phase: CHIRALPAK® IA 20 μm. n-Heptane/dichloromethane=75/25 (v/v) was used as the mobile phase. Flow rate: 270 ml/minute. Temperature: 25° C. Detection UV 300 nm Analytical HPLC monitoring system: A 250×4.6 mm column was used. Stationary phase: CHIRALPAK® IA-H 5 μm. n-Heptane/dichloromethane=75/25 (v/v) was used as the mobile phase. Flow rate: 1 ml/minute. Temperature: 25° C. Detection: Diode array detection (DAD) 254 and 300 nm. Enantiomeric excess: >98%

Compound 46

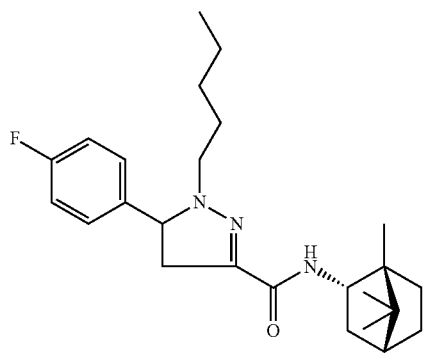

N-[endo-(1R,2S,4R)-1,7,7-trimethylbicyclo[2.2.1]hept-2-yl]-1-(n-pentyl)-5-(4-fluorophenyl)-4,5-dihydro-(1H)-pyrazole-3-carboxamide (diastereomeric mixture)

$^1$H-NMR (400 MHz, CDCl$_3$) δ 0.81-0.94 (m, 10H), 0.97 (s, 3H), 1.07-1.47 (m, 7H), 1.52-1.65 (m, 2H), 1.69 (t, J=4.4 Hz, 1H), 1.75-1.86 (m, 1H), 2.33-2.43 (m, 1H), 2.73-2.84 (m, 1H), 2.88-2.96 (m, 2H), 3.35-3.51 (m, 1H), 4.26-4.44 (m, 2H), 6.67 (br d, J=6 Hz, 1H), 7.04 (t, J=8.4 Hz, 2H), 7.31-7.39 (m, 2H).

Compound 47

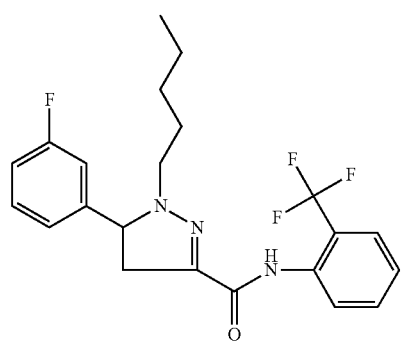

N-[3-(trifluoromethyl)benzyl]-1-(n-pentyl)-5-(3-fluorophenyl)-4,5-dihydro-(1H)-pyrazole-3-carboxamide $^1$H-NMR (400 MHz, CDCl$_3$) δ 0.81-0.91 (m, 3H), 1.16-1.35 (m, 4H), 1.52-1.65 (m, 2H), 2.84 (dd, J=17.4 and 14.1 Hz, 1H), 2.87-2.99 m, 2H), 3.46 (dd, J=17.4 and 11.4 Hz, 1H), 4.45 (dd, J=14.1 and 11.4 Hz, 1H), 4.60 (d, J=6.3 Hz, 2H), 7.01 (dt, J=8.1 and 2.1 Hz, 2H), 7.07-7.16 (m, 2H), 7.33 (dt, J=7.9 and 5.8 Hz, 1H), 7.43-7.50 (m, 1H), 7.51-7.61 (m, 3H).

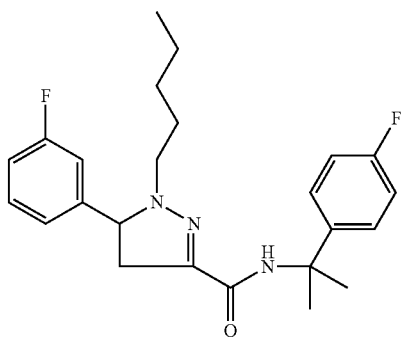

Compound 48

N-[1-(4-fluorophenyl)-1-methyl-ethyl]-1-(n-pentyl)-5-(3-fluorophenyl)-4,5-dihydro-(1H)-pyrazole-3-carboxamide ¹H-NMR (400 MHz, CDCl₃) δ 0.82-0.90 (m, 3H), 1.22-1.34 (m, 4H), 1.54-1.67 (m, 2H), 1.73 (s, 3H), 1.74 (s, 3H), 2.73 (dd, J=17.4 and 14.1 Hz, 1H), 2.93 (t, J=7.4 Hz, 2H), 3.35 (dd, J=17.4 and 11.1 Hz, 1H), 4.38 (dd, J=14.3 and 11.3 Hz, 1H), 6.94 (br s, 1H), 6.96-7.05 (m, 3H), 7.07-7.14 (m, 2H), 7.28-7.35 (m, 1H), 7.37-7.44 (m, 2H).

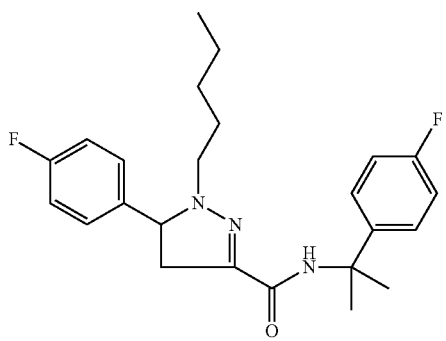

Compound 49

N-[1-(4-fluorophenyl)-1-methyl-ethyl]-1-(n-pentyl)-5-(4-fluorophenyl)-4,5-dihydro-(1H)-pyrazole-3-carboxamide ¹H-NMR (400 MHz, CDCl₃) δ 0.82-0.90 (m, 3H), 1.20-1.31 (m, 4H), 1.53-1.67 (m, 2H), 1.73 (s, 3H), 1.74 (s, 3H), 2.73 (dd, J=17.4 and 14.4 Hz, 1H), 2.91 (t, J=7.4 Hz, 2H), 3.33 (dd, J=17.4 and 11.1 Hz, 1H), 4.36 (dd, J=14.1 and 11.1 Hz, 1H), 6.95 (br s, 1H), 6.97-7.08 (m, 4H), 7.33 (dd, J=8.7 and 5.4 Hz, 2H), 7.41 (dd, J=8.9 and 5.3 Hz, 2H).

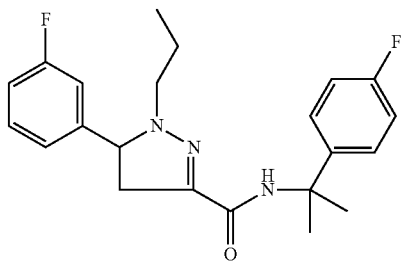

Compound 50

N-[1-(4-fluorophenyl)-1-methyl-ethyl]-1-(n-propyl)-5-(3-fluorophenyl)-4,5-dihydro-(1H)-pyrazole-3-carboxamide ¹H-NMR (400 MHz, CDCl₃) δ 0.89 (t, J=7.4 Hz, 3H), 1.55-1.71 (m, 2H), 1.73 (s, 3H), 1.74 (s, 3H), 2.73 (dd, J=17.3 and 14.3 Hz, 1H), 2.83-2.97 (m, 2H), 3.36 (dd, J=17.4 and 11.1 Hz, 1H), 4.38 (dd, J=14.3 and 11.3 Hz, 1H), 6.94 (brs, 1H), 6.96-7.05 (m, 3H), 7.07-7.15 (m, 2H), 7.28-7.35 (m, 1H), 7.40 (dd, J=8.7 and 5.4 Hz, 2H).

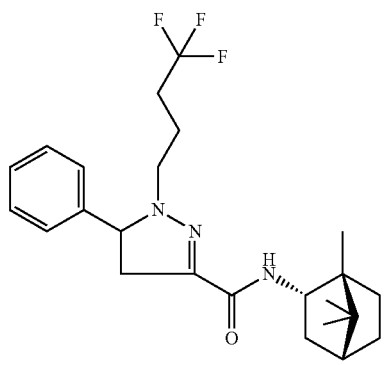

Compound 51 diastereomer 1

N-[endo-(1R,2S,4R)-1,7,7-trimethylbicyclo[2.2.1]hept-2-yl]-1-(4,4,4-trifluorobutyl)-5-phenyl-4,5-dihydro-(1H)-pyrazole-3-carboxamide (diastereomer 1)

Compounds 51 and 52 were obtained from the corresponding diasteromeric mixture via a flash chromatographic purification (silicagel). Eluant: petroleum ether (40-60)/ethylacetate=90/10 (v/v). Compound 52: second (slowest) eluting diastereomer: Compound 51: first (fastest) eluting diastereomer.

¹H-NMR (400 MHz, CDCl₃) δ 0.82-0.95 (m, 7H), 0.98 (s, 3H), 1.22-2.11 (m, 8H), 2.13-2.27 (m, 1H), 2.34-2.45 (m, 1H), 2.81-2.96 (m, 2H), 2.99-3.08 (m, 1H), 3.44 (dd, J=17.4 and 11.1 Hz, 1H), 4.26-4.40 (m, 2H), 6.65 (br d, J=9 Hz, 1H), 7.30-7.42 (m, 5H). [α²⁵_D]=102°, c=1, methanol.

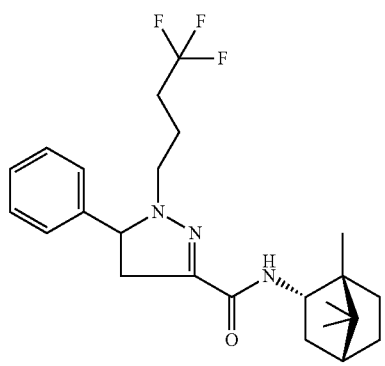

Compound 52 diastereomer 2

N-[endo-(1R,2S,4R)-1,7,7-trimethylbicyclo[2.2.1]hept-2-yl]-1-(4,4,4-trifluorobutyl)-5-phenyl-4,5-dihydro-(1H)-pyrazole-3-carboxamide (diastereomer 2)

$^1$H-NMR (400 MHz, CDCl$_3$) δ 0.83-0.94 (m, 7H), 0.97 (s, 3H), 1.20-1.32 (m, 1H), 1.38-1.49 (m, 1H), 1.54-1.63 (m, 1H), 1.70 (t, J=4.4 Hz, 1H), 1.75-1.88 (m, 2H), 1.89-2.08 (m, 2H), 2.13-2.29 (m, 1H), 2.32-2.44 (m, 1H), 2.81-2.95 (m, 2H), 2.97-3.07 (m, 1H), 3.42 (dd, J=17.4 and 10.8 Hz, 1H), 4.26-4.38 (m, 2H), 6.65 (br d, J=9.3 Hz, 1H), 7.29-7.41 (m, 5H). [α$^{25}_D$]=−102°, c=1, methanol.

N-[endo-(1R,2S,4R)-1,7,7-trimethylbicyclo[2.2.1]hept-2-yl]-1-propyl-5-(3-fluorophenyl)-4,5-dihydro-(1H)-pyrazole-3-carboxamide (diastereomer 2)

$^1$H-NMR (400 MHz, CDCl$_3$) δ 0.82-0.93 (m, 10H), 0.97 (s, 3H), 1.21-1.31 (m, 1H), 1.37-1.47 (m, 1H), 1.54-1.67 (m, 3H), 1.69 (t, J=4.4 Hz, 1H), 1.74-1.86 (m, 1H), 2.31-2.43 (m, 1H), 2.79 (dd, J=17.4 and 14.1 Hz, 1H), 2.85-2.99 (m, 2H), 3.44 (dd, J=17.1 and 11.1 Hz, 1H), 4.30 (br tt, J=9.1 and 2.4 Hz, 1H), 4.40 (dd, J=14.0 and 11.3 Hz, 1H), 6.66 (br d, J=9 Hz, 1H), 7.00 (dt, J=8.3 and 1.9 Hz, 1H), 7.08-7.15 (m, 2H), 7.31 (dd, J=7.8 and 6 Hz, 1H). [α$^{25}_D$]=145°, c=1, methanol.

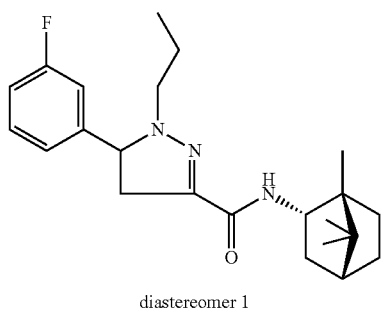

Compound 53 diastereomer 1

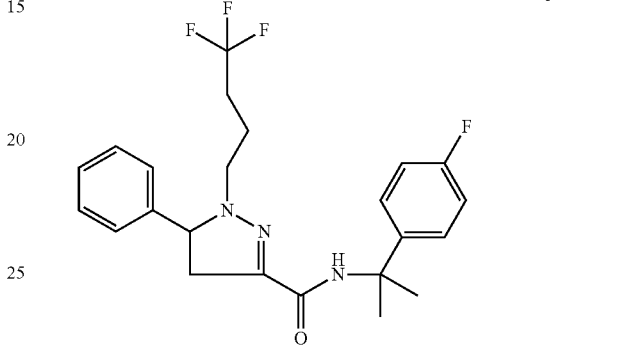

Compound 55

N-[endo-(1R,2S,4R)-1,7,7-trimethylbicyclo[2.2.1]hept-2-yl]-1-propyl-5-(3-fluorophenyl)-4,5-dihydro-(1H)-pyrazole-3-carboxamide (diastereomer 1)

Compounds 53 and 54 were obtained from the corresponding diasteromeric mixture via a flash chromatographic purification (silicagel). Eluant gradient: petroleum ether (40-60)/ethylacetate=95/5=>petroleum ether (40-60)/ethylacetate=90/10 (v/v). Compound 53: second (slowest) eluting diastereomer: Compound 54: first (fastest) eluting diastereomer.

$^1$H-NMR (400 MHz, CDCl$_3$) δ 0.83-0.94 (m, 10H), 0.97 (s, 3H), 1.21-1.30 (m, 1H), 1.36-1.47 (m, 1H), 1.54-1.73 (m, 4H), 1.74-1.86 (m, 1H), 2.31-2.43 (m, 1H), 2.80 (dd, J=17.3 and 14.3 Hz, 1H), 2.85-2.99 (m, 2H), 3.43 (dd, J=17.4 and 11.1 Hz, 1H), 4.25-4.35 (m, 1H), 4.38 (dd, J=14.1 and 11.1 Hz, 1H) 6.66 (br d, J=9 Hz, 1H) 7.00 (br t, J=8.3 Hz, 1H), 7.09-7.18 (m, 2H), 7.28-7.37 (m, 1H). [α$^{25}_D$]=−122°, c=1, methanol.

N-[1-(4-fluorophenyl)-1-methyl-ethyl]-1-(4,4,4-trifluorobutyl)-5-phenyl-4,5-dihydro-(1H)-pyrazole-3-carboxamide $^1$H-NMR (400 MHz, CDCl$_3$) δ 1.74 (s, 3H), 1.75 (s, 3H), 1.78-1.88 (m, 1H), 1.89-2.06 (m, 2H), 2.14-2.26 (m, 1H), 2.80 (dd, J=17.4 and 14.4 Hz, 1H), 2.85-2.93 (m, 1H), 2.98-3.06 (m, 1H), 3.35 (dd, J=17.4 and 10.8 Hz, 1H), 4.32 (dd, J=14.6 and 11 Hz, 1H), 6.93 (br s, 1H), 7.02 (t, J=8.7 Hz, 2H), 7.29-7.38 (m, 5H), 7.38-7.44 (m, 2H).

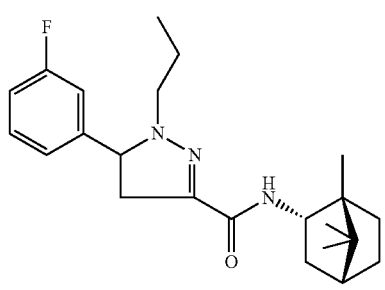

Compound 54 diastereomer 2

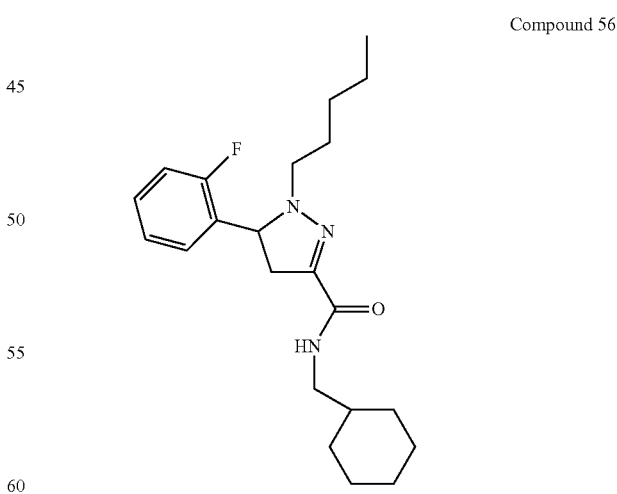

Compound 56

N-Cyclohexylmethyl-1-(n-pentyl)-5-(2-fluorophenyl)-4,5-dihydro-(1H)-pyrazole-3-carboxamide $^1$H-NMR (400 MHz, CDCl$_3$) δ 0.86 (t, J=7, 3H), 0.91-1.03 (m, 2H), 1.10-1.34 (m, 7H), 1.47-1.70 (m, 4H), 1.70-1.81 (m, 4H), 2.80 (dd, J=17.1 and 13.8 Hz, 1H), 2.88-3.01 (m, 2H), 3.12-3.25 (m, 2H), 3.48 (dd, J=17.1 and 11.4 Hz, 1H), 4.73 (dd, J=13.8 and 11.4 Hz, 1H), 6.67 (br t, J~6.5 Hz, 1H), 7.05 (dd, J=10.1 and 8.6 Hz, 1H), 7.15 (t, J=7.5 Hz, 1H), 7.24-7.31 (m, 1H), 7.48 (dt, J=7.5 and ~2 Hz, 1H).

2.17 (m, 1H), 2.24 (br t, J=4.5 Hz, 1H), 2.49 (br t, J=4.3 Hz, 1H), 2.79 (dd, J=17.3 and 13.7 Hz, 1H), 2.89-3.03 (m, 2H), 3.48 (dd, J=17.4 and 11.4 Hz, 1H), 4.13-4.23 (m, 1H), 4.70-4.78 (m, 1H), 6.63-6.69 (m, 1H), 7.02-7.08 (m, 1H), 7.13-7.18 (m, 1H), 7.24-7.31 (m, 1H), 7.45-7.52 (m, 1H).

Compound 57

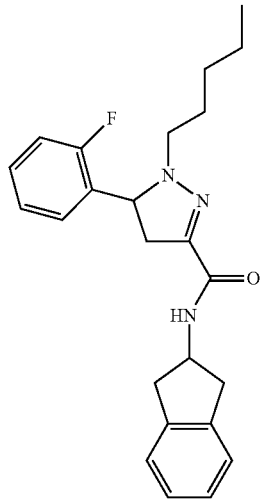

N-(Indan-2-yl)-1-(n-pentyl)-5-(2-fluorophenyl)-4,5-dihydro-(1H)-pyrazole-3-carboxamide $^1$H-NMR (400 MHz, CDCl$_3$) δ 0.81-0.86 (m, 3H), 1.13-1.31 (m, 4H) 1.51-1.64 (m, 2H), 2.81 (dd, J=17.4 and 13.8 Hz, 1H), 2.86-2.97 (m, 4H), 3.32-3.41 (m, 2H), 3.49 (dd, J=17.1 and 11.4 Hz, 1H), 4.74 (dd, J=13.7 and 11.6 Hz, 1H), 4.78-4.87 (m, 1H), 6.78 (br d, J=8.1 Hz, 1H), 7.01-7.08 (m, 1H) 7.12-7.17 (m, 1H), 7.17-7.22 (m, 2H), 7.22-7.31 (m, 3H), 7.42-7.49 (m, 1H).

Compound 58

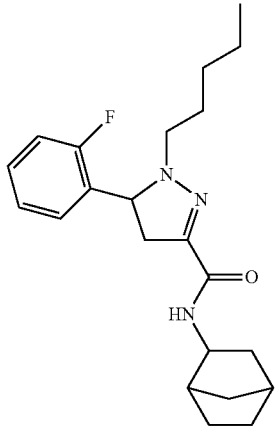

2-endo isomer

N-(Endo-bicyclo[2.2.1]hept-2-yl)-1-(n-pentyl)-5-(2-fluorophenyl)-4,5-dihydro-(1H)-pyrazole-3-carboxamide (diastereomeric mixture)

$^1$H-NMR (400 MHz, CDCl$_3$) δ 0.81-0.89 (m, 4H), 1.20-1.38 (m, 6H), 1.43-1.52 (m, 2H), 1.53-1.70 (m, 4H), 2.06-

Compound 59

N-(Cycloheptyl)-1-(n-pentyl)-5-(2-fluorophenyl)-4,5-dihydro-(1H)-pyrazole-3-carboxamide $^1$H-NMR (400 MHz, CDCl$_3$) δ 0.86 (t, J=7 Hz, 3H), 1.20-1.32 (m, 4H), 1.46-1.71 (m, 11H), 1.92-2.03 (m, 2H), 2.74-2.84 (m, 2H), 2.90-2.98 (m, 2H), 3.47 (dd, J=17.1 and 11.4 Hz, 1H), 3.96-4.07 (m, 1H), 4.72 (dd, J=13.8 and 11.1 Hz, 1H), 6.56 (br d, J=8.4 Hz, 1H), 7.01-7.08 (m, 1H), 7.12-7.18 (m, 1H), 7.24-7.31 (m, 1H), 7.46-7.51 (m, 1H).

Compound 60

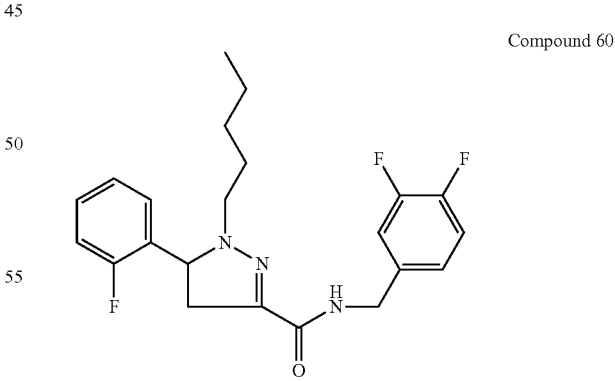

N-[3,4-difluorobenzyl]-1-(n-pentyl)-5-(2-fluorophenyl)-4,5-dihydro-(1H)-pyrazole-3-carboxamide $^1$H-NMR (400 MHz, CDCl$_3$) δ 0.85 (t, J=6.9 Hz, 3H), 1.17-1.33 (m, 4H), 1.54-1.70 (m, 2H), 2.84 (dd, J=17.3 and 13.7 Hz, 1H), 2.88-3.02 (m, 2H), 3.50 (dd, J=17.3 and 11.6 Hz, 1H), 4.43-4.54 (m, 2H), 4.79 (dd, J=13.8 and 11.7 Hz, 1H), 6.96 (br t, J=6.3 Hz, 1H), 7.02-7.20 (m, 5H), 7.25-7.32 (m, 1H), 7.47 (dt, J=7.5 and 1.8 Hz, 1H).

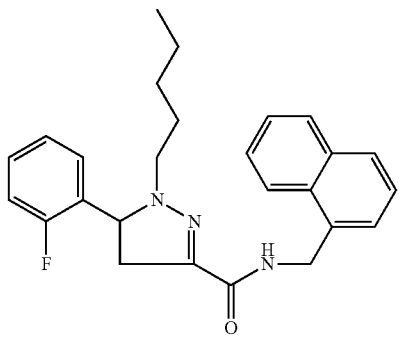

Compound 61

N-[Naphthalen-1-ylmethyl]-1-(n-pentyl)-5-(2-fluorophenyl)-4,5-dihydro-(1H)-pyrazole-3-carboxamide $^1$H-NMR (400 MHz, CDCl$_3$) δ 0.80 (t, J=6.9 Hz, 3H), 1.21 (m, 4H), 1.49-1.61 (m, 2H), 2.79-2.97 (m, 3H), 3.53 (dd, J=17.1 and 11.4 Hz, 1H), 4.71-4.80 (m, 1H), 4.95-5.06 (m, 2H), 6.84-6.90 (m, 1H)m 7.02-7.08 (m, 1H), 7.15 (t, J=7.5 Hz, 1H), 7.24-7.31 (m, 1H), 7.42-7.61 (m, 5H), 7.83 (d, J=8.1 Hz, 1H), 7.90 (d, J=8.1 Hz, 1H), 8.10 (d, J=8.1 Hz, 1H).

Compound 62

N-[2-(Indol-3-yl)ethyl]-1-(n-pentyl)-5-(2-fluorophenyl)-4,5-dihydro-(1H)-pyrazole-3-carboxamide $^1$H-NMR (400 MHz, CDCl$_3$) δ 0.86 (t, J=6.9 Hz, 3H), 1.17-1.32 (m, 4H), 1.52-1.64 (m, 2H), 2.81 (dd, J=17.3 and 13.7 Hz, 1H), 2.86-2.98 (m, 2H), 3.04 (t, J=6.9 Hz, 2H), 3.48 (dd, J=17.1 and 11.4 Hz, 1H), 3.68 (q, J=6.6 Hz, 2H), 4.68-4.78 (m, 1H), 6.77 (br t, J=6.2 Hz, 1H), 7.01-7.10 (m, 2H), 7.14 (q, J=7.1 Hz, 2H), 7.21 (t, J=7.5 Hz, 1H), 7.24-7.31 (m, 1H), 7.38 (d, J=8.1 Hz, 1H), 7.43-7.49 (m, 1H), 7.65 (d, J=7.8 Hz, 1H), 8.06 (br s, 1H).

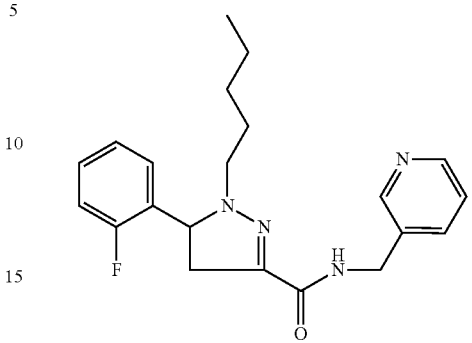

Compound 63

N-[(Pyridin-3-yl)methyl]-1-(n-pentyl)-5-(2-fluorophenyl)-4,5-dihydro-(1H)-pyrazole-3-carboxamide $^1$H-NMR (400 MHz, CDCl$_3$) δ 0.81-0.89 (m, 3H), 1.15-1.33 (m, 4H), 1.53-1.69 (m, 2H), 2.84 (dd, J=17.3 and 13.7 Hz, 1H), 2.89-3.02 (m, 2H), 3.50 (dd, J=17.3 and 11.6 Hz, 1H), 4.51-4.60 (m, 2H) 4.79 (dd, J=13.8 and 11.4 Hz, 1H), 6.98 (br t, J=6.5 Hz, 1H), 7.03-7.09 (m, 1H), 7.16 (t, J=7 Hz, 1H), 7.24-7.34 (m, 2H), 7.46 (dt, J=7.5 and 2 Hz, 1H), 7.69 (br d, J=7.8 Hz, 1H), 8.54 (br d, J=4.8 Hz, 1H), 8.58-8.62 (m, 1H).

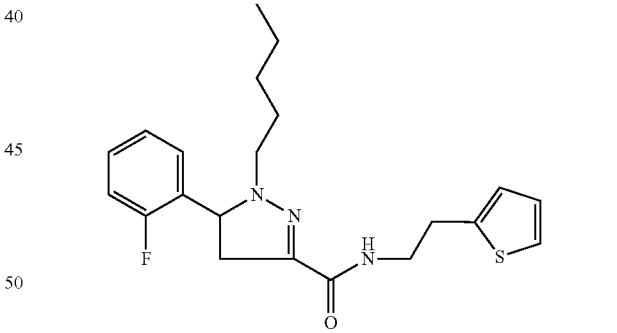

Compound 64

N-[2-(Thien-2-yl)ethyl]-1-(n-pentyl)-5-(2-fluorophenyl)-4,5-dihydro-(1H)-pyrazole-3-carboxamide $^1$H-NMR (400 MHz, CDCl$_3$) δ 0.84-0.90 (m, 3H), 1.18-1.34 (m, 4H), 1.56-1.67 (m, 2H), 2.80 (dd, J=17.1 and 13.8 Hz, 1H), 2.86-3.01 (m, 2H), 3.10 (t, J=6.9 Hz, 2H), 3.48 (dd, J=17.1 and 11.4 Hz, 1H), 3.62 (q, J=6.6 Hz, 2H), 4.75 (dd, J=13.8 and 11.4 Hz, 1H), 6.79 (br t, J=6.3 Hz, 1H), 6.88 (dd, J=3.2 and 1 Hz, 1H), 6.96 (dd, J=5.1 and 3.3 Hz, 1H), 7.02-7.09 (m, 1H), 7.13-7.19 (m, 2H), 7.24-7.31 (m, 1H), 7.44-7.50 (m, 1H).

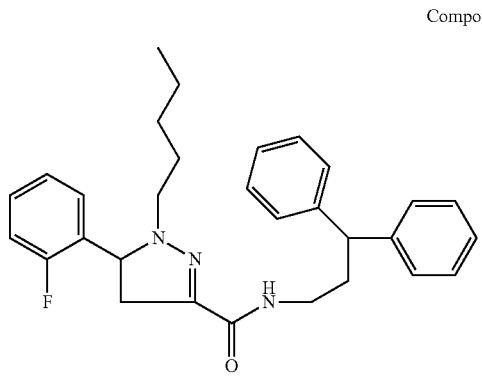

Compound 65

N-[3,3-diphenylpropyl]-1-(n-pentyl)-5-(2-fluorophenyl)-4,5-dihydro-(1H)-pyrazole-3-carboxamide $^1$H-NMR (400 MHz, CDCl$_3$) δ 0.87 (t, J=6.9 Hz, 3H), 1.20-1.34 (m, 4H), 1.55-1.69 (m, 2H), 2.31-2.39 (m, 2H), 2.77 (dd, J=17.4 and 13.8 Hz, 1H), 2.85-2.99 (m, 2H), 3.31 (q, J=8 Hz, 2H), 3.45 (dd, J=17.1 and 11.4 Hz, 1H), 4.00 (t, J=7.8 Hz, 1H), 4.72 (dd, J=14 and 11.23 Hz, 1H), 6.59 (br t, J=6.6 Hz, 1H), 7.01-7.09 (m, 1H), 7.13-7.20 (m, 3H), 7.24-7.31 (m, 9H), 7.47 (dt, J=7.5 and 2 Hz, 1H).

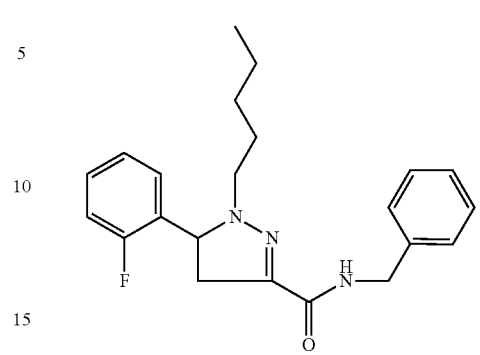

Compound 67

N-Benzyl-1-(n-pentyl)-5-(2-fluorophenyl)-4,5-dihydro-(1H)-pyrazole-3-carboxamide 1H-NMR (400 MHz, CDCl$_3$) δ 0.84 (t, J=6.9 Hz, 3H), 1.17-1.32 (m, 4H), 1.54-1.66 (m, 2H), 2.84 (dd, J=17.1 and 13.8 Hz, 1H), 2.86-3.00 (m, 2H), 3.51 (dd, J=17.4 and 11.4 Hz, 1H), 4.50-4.58 (m, 2H), 4.76 (dd, J=13.8 and 11.4 Hz, 1H), 6.92 (br t, J=6 Hz, 1H), 7.02-7.09 (m, 1H), 7.16 (dt, J=7.5 and 1.2 Hz, 1H), 7.25-7.32 (m, 3H), 7.33-7.39 (m, 3H), 7.47 (dt, J=7.1 and 1.3 Hz, 1H).

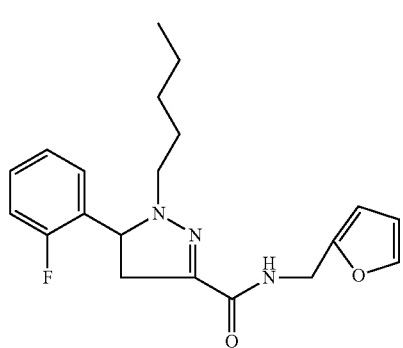

Compound 66

N-[(Furan-2-yl)methyl]-1-(n-pentyl)-5-(2-fluorophenyl)-4,5-dihydro-(1H)-pyrazole-3-carboxamide $^1$H-NMR (400 MHz, CDCl$_3$) δ 0.82-0.90 (m, 3H), 1.17-1.35 (m, 4H), 1.54-1.69 (m, 2H), 2.82 (dd, J=17.3 and 13.7 Hz, 1H), 2.87-3.01 (m, 2H), 3.49 (dd, J=17.3 and 11.6 Hz, 1H), 4.48-4.60 (m, 2H), 4.76 (dd, J=13.7 and 11.6 Hz, 1H), 6.26-6.37 (m, 2H), 6.90 (br t, J=6 Hz, 1H), 7.02-7.09 (m, 1H), 7.12-7.18 (m, 1H), 7.24-7.32 (m, 1H), 7.36-7.40 (m, 1H), 7.46 (dt, J=8.2 and 2 Hz, 1H).

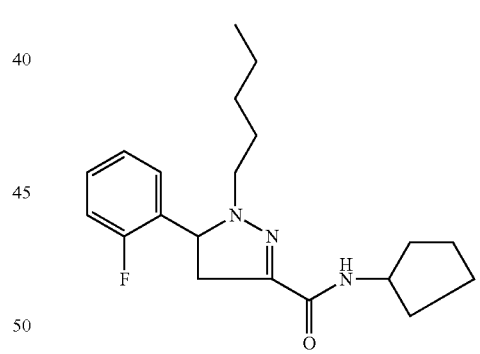

Compound 68

N-Cyclopentyl-1-(n-pentyl)-5-(2-fluorophenyl)-4,5-dihydro-(1H)-pyrazole-3-carboxamide $^1$H-NMR (400 MHz, CDCl$_3$) δ 0.86 (t, J=6.9 Hz, 3H), 1.18-1.35 (m, 4H), 1.41-1.53 (m, 2H), 1.55-1.80 (m, 6H), 1.97-2.10 (m, 2H), 2.79 (dd, J=17.4 and 13.8 Hz, 1H), 2.87-3.01 (m, 2H), 3.48 (dd, J=17.4 and 11.4 Hz, 1H), 4.27 (sextet, J=7.1 Hz, 1H), 4.72 (dd, J=14 and 11.3 Hz, 1H), 6.54 (br d, J=7.8 Hz, 1H), 7.05 (dd, J=11 and 7.7 Hz, 1H), 7.15 (t, J=7.4 Hz, 1H), 7.24-7.32 (m, 1H), 7.48 (dt, J=7.4 and 1.6 Hz, 1H).

Compound 69

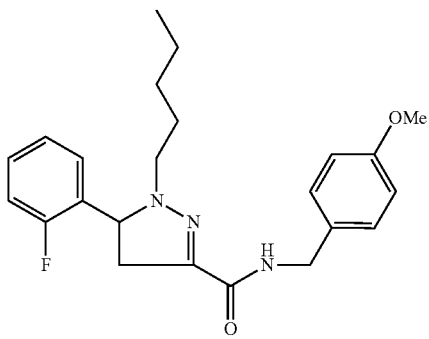

N-(4-Methoxybenzyl)-1-(n-pentyl)-5-(2-fluorophenyl)-4,5-dihydro-(1H)-pyrazole-3-carboxamide ¹H-NMR (400 MHz, CDCl₃) δ 0.84 (t, J=6.9 Hz, 3H), 1.17-1.32 (m, 4H), 1.54-1.67 (m, 2H), 2.82 (dd, J=17.4 and 13.8 Hz, 1H), 2.87-2.99 (m, 2H), 3.50 (dd, J=17.1 and 11.4 Hz, 1H), 3.81 (s, 3H), 4.46-4.49 (m, 2H), 4.75 (dd, J=14.1 and 11.4 Hz, 1H), 6.82-6.91 (m, 3H), 7.05 (dd, J=11 and 7.7 Hz, 1H), 7.15 (t, J=7.5 Hz, 1H), 7.24-7.31 (m, 3H), 7.47 (dt, J=7.5 and 1.8 Hz, 1H).

Compound 70

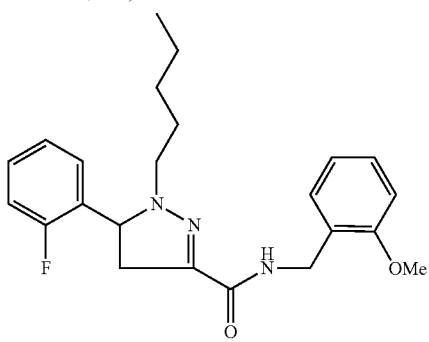

N-(2-Methoxybenzyl)-1-(n-pentyl)-5-(2-fluorophenyl)-4,5-dihydro-(1H)-pyrazole-3-carboxamide ¹H-NMR (400 MHz, CDCl₃) δ 0.86 (t, J=6.9 Hz, 3H), 1.18-1.33 (m, 4H), 1.56-1.67 (m, 2H), 2.80 (dd, J=17.1 and 13.8 Hz, 1H), 2.86-2.99 (m, 2H), 3.49 (dd, J17.1 and 11.4 Hz, 1H), 3.88 (s, 3H), 4.52-4.56 (m, 2H), 4.73 (dd, J=14 and 11.3 Hz, 1H), 6.87-6.96 (m, 2H), 7.05 (dd, J=9.8 and 8.9 Hz, 1H), 7.08-7.18 (m, 2H), 7.23-7.34 (m, 3H), 7.47 (dt, J=7.6 and 2 Hz, 1H).

Compound 71

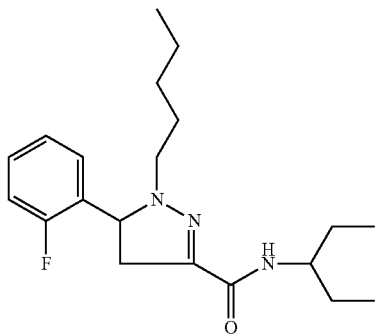

N-[(1-ethyl)propyl]-1-(n-pentyl)-5-(2-fluorophenyl)-4,5-dihydro-(1H)-pyrazole-3-carboxamide ¹H-NMR (400 MHz, CDCl₃) δ 0.82-0.89 (m, 3H), 0.90-0.98 (m, 6H), 1.19-1.34 (m, 4H), 1.39-1.53 (m, 2H), 1.54-1.70 (m, 4H), 2.81 (dd, J=17.1 and 13.8 Hz, 1H), 2.89-3.03 (m, 2H), 3.49 (dd, J=17.3 and 11.23 Hz, 1H), 3.79-3.91 (m, 1H), 4.75 (dd, J=13.8 and 11.4 Hz, 1H), 6.38 (br d, J=9.3 Hz, 1H), 7.01-7.09 (m, 1H), 7.16 (t, J=7.5 Hz, 1H), 7.24-7.32 (m, 1H), 7.49 (dt, J=7.5 and 1.8 Hz, 1H).

Compound 72

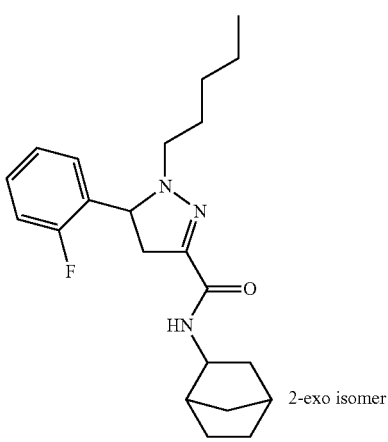

2-exo isomer

N-(Exo-bicyclo[2.2.1]hept-2-yl)-1-(n-pentyl)-5-(2-fluorophenyl)-4,5-dihydro-(1H)-pyrazole-3-carboxamide (diastereomeric mixture)

1H-NMR (400 MHz, CDCl₃) δ 0.86 (t, J=6.9 Hz, 3H), 1.11-1.19 (m, 1H), 1.19-1.33 (m, 7H), 1.38-1.69 (m, 5H), 1.79-1.87 (m, 1H), 2.26-2.33 (m, 2H), 2.79 (dd, J=17.4 and 13.8 Hz, 1H), 2.88-3.01 (m, 2H), 3.47 (dd, J=17.4 and 11.4 Hz, 1H), 3.79 (dt, J=7.7 and 3.4 Hz, 1H), 4.68-4.77 (m, 1H), 6.48 (br d, J=7.5 Hz, 1H), 7.05 (dd, J=9.8 and 8.6 Hz, 1H), 7.12-7.18 (m, 1H), 7.24-7.31 (m, 1H), 7.44-7.51 (m, 1H).

Compound 73

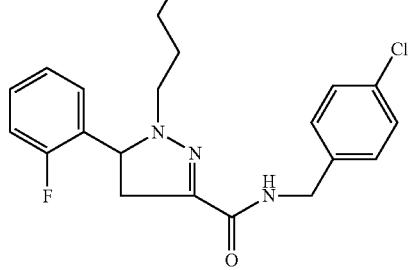

N-(4-chlorobenzyl)-1-(n-pentyl)-5-(2-fluorophenyl)-4,5-dihydro-(1H)-pyrazole-3-carboxamide $^1$H-NMR (400 MHz, CDCl$_3$) δ 0.84 (t, J=6.9 Hz, 3H), 1.16-1.32 (m, 4H), 1.52-1.67 (m, 2H), 2.83 (dd, J=17.3 and 13.7 Hz, 1H), 2.88-3.01 (m, 2H), 3.50 (dd, J=17.4 and 11.4 Hz, 1H), 4.46-4.55 (m, 2H), 4.78 (dd, J=13.8 and 11.4 Hz, 1H), 6.95 (br t, J=6.3 Hz, 1H), 7.02-7.09 (m, 1H), 7.12-7.19 (m, 1H), 7.24-7.34 (m, 5H), 7.46 (tt, J=7.5 and 2 Hz, 1H).

s, 3H), 2.81 (dd, J=17.4 and 13.8 Hz, 1H), 2.90-3.10 (m, 4H), 3.49 (dd, J=17.1 and 11.4 Hz, 1H), 4.75 (dd, J=14 and 11.23 Hz, 1H), 6.69 (t, J=6.8 Hz, 1H), 7.02-7.08 (m, 1H), 7.16 (br t, J~8, 1H), 7.24-7.31 (m, 1H), 7.49 (dt, J=7.4 and 2 Hz, 1H).

Compound 74

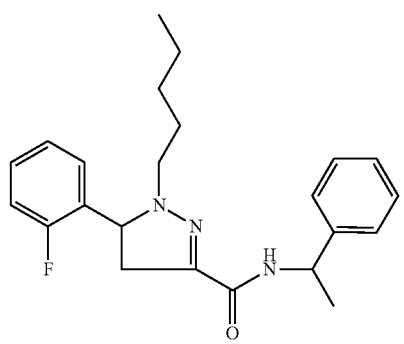

N-(1-Phenyl-ethyl)-1-(n-pentyl)-5-(2-fluorophenyl)-4,5-dihydro-(1H)-pyrazole-3-carboxamide (1:1 diasteromeric mixture)

$^1$H-NMR (400 MHz, CDCl$_3$) δ 0.80-0.90 (m, 3H), 1.17-1.33 (m, 4H), 1.53-1.70 (m, 5H), 2.73-2.87 (m, 1H), 2.88-3.02 (m, 2H), 3.42-3.54 (m, 1H), 4.69-4.80 (m, 1H), 5.20 (quintet, J=7.3 Hz, 1H), 6.85 (br d, J=8.4 Hz, 1H), 7.01-7.08 (m, 1H), 7.11-7.19 (m, 1H), 7.23-7.31 (m, 2H), 7.32-7.41 (m, 4H), 7.43-7.51 (m, 1H).

Compound 76

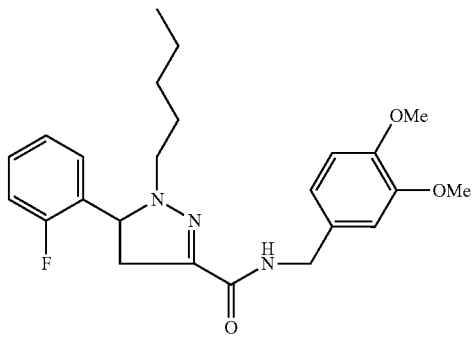

N-(3,4-Dimethoxybenzyl)-1-(n-pentyl)-5-(2-fluorophenyl)-4,5-dihydro-(1H)-pyrazole-3-carboxamide $^1$H-NMR (400 MHz, CDCl$_3$) δ 0.84 (t, J=6.9 Hz, 3H), 1.15-1.32 (m, 4H), 1.54-1.66 (m, 2H), 2.83 (dd, J=17.1 and 13.8 Hz, 1H), 2.86-3.00 (m, 2H), 3.51 (dd, J=17.3 and 11.6 Hz, 1H), 3.88 (s, 3H), 3.89 (s, 3H), 4.43-4.52 (m, 2H), 4.76 (dd, J=14 and 11.6 Hz, 1H), 6.82-6.92 (m, 4H), 7.03-7.09 (m, 1H), 7.16 (t, J=7.2 Hz, 1H), 7.25-7.32 (m, 1H), 7.47 (dt, J=7.5 and 2 Hz, 1H).

Compound 75

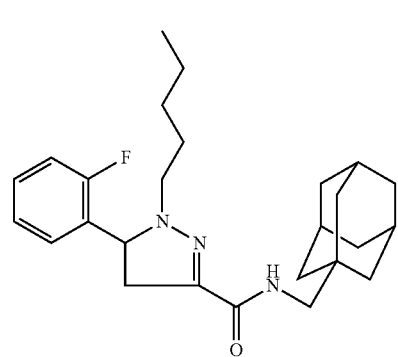

N-(Adamantylmethyl)-1-(n-pentyl)-5-(2-fluorophenyl)-4,5-dihydro-(1H)-pyrazole-3-carboxamide $^1$H-NMR (400 MHz, CDCl$_3$) δ 0.84-0.89 (m, 3H), 1.21-1.35 (m, 4H), 1.51-1.57 (m, 6H), 1.57-1.77 (m, 6H), 2.00 (br Compound 77

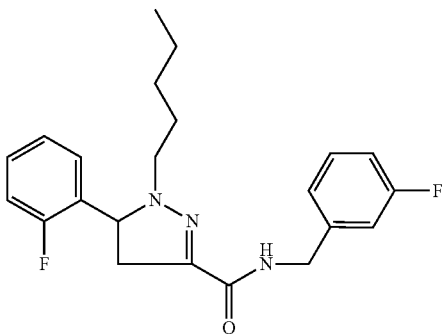

N-(3-Fluorobenzyl)-1-(n-pentyl)-5-(2-fluorophenyl)-4,5-dihydro-(1H)-pyrazole-3-carboxamide $^1$H-NMR (400 MHz, CDCl$_3$) δ 0.82-0.88 (m, 3H), 1.17-1.33 (m, 4H), 1.53-1.71 (m, 2H), 2.84 (dd, J=17.3 and 13.7

Hz, 1H), 2.90-3.03 (m, 2H), 3.51 (dd, J=17.3 and 11.6 Hz, 1H), 4.48-4.58 (m, 2H), 4.79 (dd, J=13.8 and 11.4 Hz, 1H), 6.93-7.02 (m, 2H), 7.02-7.13 (m, 3H), 7.16 (t, J=7.5 Hz, 1H), 7.25-7.35 (m, 2H), 7.47 (dt, J=7.5 and 2 Hz, 1H).

1H), 6.99-7.09 (m, 4H), 7.15 (t, J=7.5 Hz, 1H), 7.24-7.31 (m, 1H), 7.46 (dt, J=7.5 and 2 Hz, 1H), 7.50 (d, J=7.8 Hz, 1H), 8.10 (br s, 1H).

Compound 78

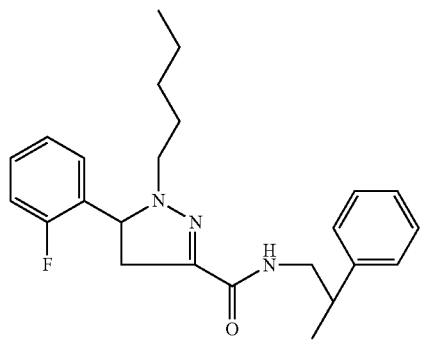

N-(2-Phenyl-propyl)-1-(n-pentyl)-5-(2-fluorophenyl)-4,5-dihydro-(1H)-pyrazole-3-carboxamide (1:1 diasteromeric mixture)

$^1$H-NMR (400 MHz, CDCl$_3$) δ 0.86 (t, J=7 Hz, 3H), 1.17-1.30 (m, 4H), 1.32 (d, J=6.9 Hz, 3H), 1.52-1.63 (m, 2H), 2.72-3.06 (m, 4H), 3.34-3.51 (m, 2H), 3.58-3.67 (m, 1H), 4.65-4.76 (m, 1H), 6.57 (br t, J=6.3 Hz, 1H), 7.04 (dd, J=9.8 and 8.9 Hz, 1H), 7.11-7.17 (m, 1H), 7.21-7.30 (m, 4H), 7.30-7.36 (m, 2H), 7.42-7.49 (m, 1H).

Compound 80

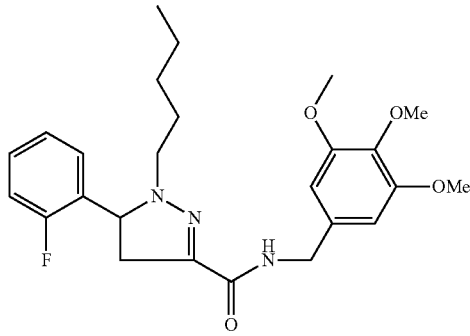

N-(3,4,5-Trimethoxybenzyl)-1-(n-pentyl)-5-(2-fluorophenyl)-4,5-dihydro-(1H)-pyrazole-3-carboxamide $^1$H-NMR (400 MHz, CDCl$_3$) δ 0.84 (t, J=6.9 Hz, 3H), 1.18-1.31 (m, 4H), 1.55-1.66 (m, 2H), 2.84 (dd, J=17.3 and 13.7 Hz, 1H), 2.89-3.01 (m, 2H), 3.52 (dd, J=17.3 and 11.6 Hz, 1H), 3.84 (s, 3H), 3.87 (s, 6H), 4.42-4.52 (m, 2H), 4.78 (dd, J=13.8 and 11.4 Hz, 1H), 6.57 (s, 2H), 6.91 (br t, J=6.2 Hz, 1H), 7.06 (dd, J=9.6 and 8.7 Hz, 1H), 7.16 (t, J=7.5 Hz, 1H), 7.25-7.32 (m, 1H), 7.44-7.50 (m, 1H).

Compound 79

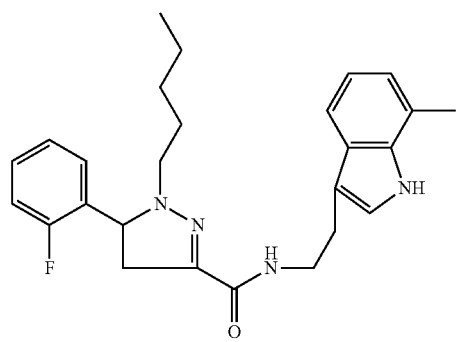

N-[2-(7-methyl-indol-3-yl)ethyl]-1-(n-pentyl)-5-(2-fluorophenyl)-4,5-dihydro-(1H)-pyrazole-3-carboxamide $^1$H-NMR (400 MHz, CDCl$_3$) δ 0.86 (t, J=6.9 Hz, 3H), 1.18-1.31 (m, 4H), 1.53-1.65 (m, 2H), 2.49 (s, 3H), 2.80 (dd, J=17.1 and 13.8 Hz, 1H), 2.83-2.97 (m, 2H), 3.03 (t, J=7.1 Hz, 2H), 3.48 (dd, J=17.1 and 11.4 Hz, 1H), 3.68 (q, J=6.9 Hz, 2H), 4.72 (dd, J=13.8 and 11.4 Hz, 1H), 6.78 (t, J=6.2 Hz, Compound 81

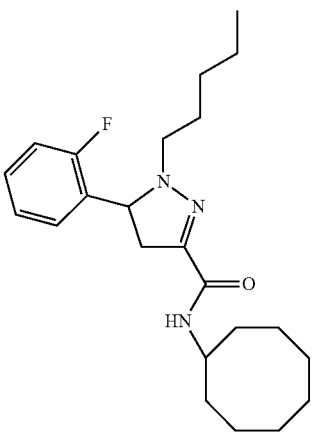

N-(Cyclooctyl)-1-(n-pentyl)-5-(2-fluorophenyl)-4,5-dihydro-(1H)-pyrazole-3-carboxamide $^1$H-NMR (400 MHz, CDCl$_3$) δ 0.86 (t, J=6.92 Hz, 3H), 1.18-1.34 (m, 4H), 1.50-1.75 (m, 14H), 1.82-1.95 (m, 2H), 2.79 (dd, J=17.4 and 13.8 Hz, 1H), 2.87-3.02 (m, 2H), 3.47 (dd, J=17.3 and 11.3 Hz, 1H), 4.01-4.11 (m, 1H), 4.72 (dd, J=14 and 11.3 Hz, 1H), 6.57 (br d, J=8.4 Hz, 1H), 7.01-7.09 (m, 1H), 7.12-7.18 (m, 1H), 7.24-7.31 (m, 1H), 7.45-7.51 (m, 1H).

Hz, 1H), 4.67-4.82 (m, 3H), 6.99 (br t, J=6.6 Hz, 1H), 7.02-7.09 (m, 1H), 7.15 (t, J=8.1 Hz, 1H), 7.25-7.31 (m, 1H), 7.38 (t, J=7.7 Hz, 1H), 7.46 (dt, J=7.5 and 1.8 Hz, 1H), 7.54 (t, J=7.7 Hz, 1H), 7.60-7.68 (m, 2H).

Compound 82

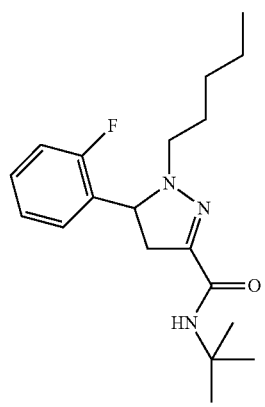

N-(tert-Butyl)-1-(n-pentyl)-5-(2-fluorophenyl)-4,5-dihydro-(1H)-pyrazole-3-carboxamide $^1$H-NMR (400 MHz, CDCl$_3$) δ 0.86 (t, J=7.2 Hz, 3H), 1.20-1.33 (m, 4H), 1.42 (s, 9H), 1.56-1.68 (m, 2H), 2.77 (dd, J=17.1 and 13.8 Hz, 1H), 2.92 (br t, J=7.1 Hz, 2H), 3.45 (dd, J=17.3 and 11.3 Hz, 1H), 4.70 (dd, J=14 and 11.3 Hz, 1H), 6.50 (br s,1H), 7.01-7.08 (m, 1H), 7.12-7.18 (m, 1H), 7.24-7.31 (m, 1H), 7.48 (dt, J=7.5 and 1.8 Hz, 1H).

Compound 84

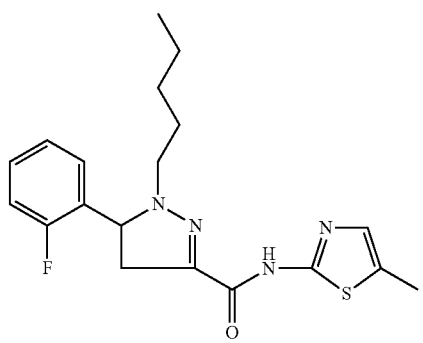

N-(5-Methyl-thiazol-2-yl)-1-(n-pentyl)-5-(2-fluorophenyl)-4,5-dihydro-(1H)-pyrazole-3-carboxamide $^1$H-NMR (400 MHz, CDCl$_3$) δ 0.85-0.89 (m, 3H), 1.19-1.34 (m, 4H), 1.59-1.69 (m, 2H), 2.40 (s, 3H), 2.93 (dd, J=17 and 13.1 Hz, 1H), 2.97-3.14 (m, 2H), 3.56 (dd, J=17.1 and 12.3 Hz, 1H), 4.96 (t, J=12.6 Hz, 1H), 7.05-7.12 (m, 2H), 7.18 (t, J=7.4 Hz, 1H), 7.28-7.34 (m, 1H), 7.43 (dt, J=7.5 and 1.8 Hz, 1H), 10.02 (br s, 1H).

Compound 83

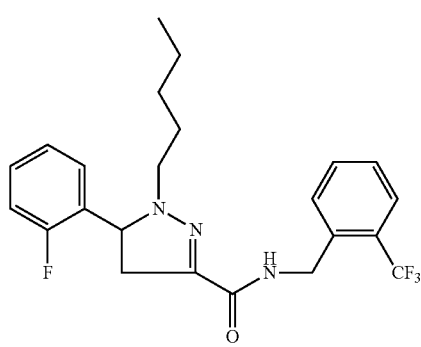

N-(2-(Trifluoromethyl)benzyl)-1-(n-pentyl)-5-(2-fluorophenyl)-4,5-dihydro-(1H)-pyrazole-3-carboxamide 1H-NMR (400 MHz, CDCl$_3$) δ 0.85 (t, J=6.9 Hz, 3H), 1.17-1.33 (m, 4H), 1.54-1.70 (m, 2H), 2.83 (dd, J=17.1 and 13.8 Hz, 1H), 2.88-3.02 (m, 2H), 3.50 (dd, J=17.3 and 11.6

Compound 85

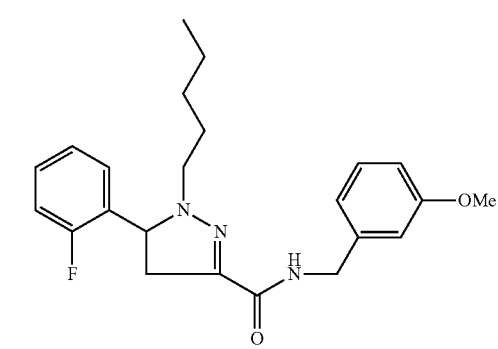

N-(3-Methoxybenzyl)-1-(n-pentyl)-5-(2-fluorophenyl)-4,5-dihydro-(1H)-pyrazole-3-carboxamide $^1$H-NMR (400 MHz, CDCl$_3$) δ 0.84 (t, J=6.9 Hz, 3H), 1.17-1.32 (m, 4H), 1.54-1.68 (m, 2H), 2.83 (dd, J=17.1 and 13.8 Hz, 1H), 2.88-3.00 (m, 2H), 3.51 (dd, J=17.3 and 11.6 Hz, 1H), 3.81 (s, 3H), 4.48-4.57 (m, 2H), 4.76 (dd, J=13.8 and 11.4 Hz, 1H), 6.81-6.85 (m, 1H), 6.87-6.95 (m, 3H), 7.02-7.09 (m, 1H), 7.16 (t, J=6.9 Hz, 1H), 7.24-7.31 (m, 2H), 7.47 (dt, J=7.5 and 1.8 Hz, 1H).

Compound 86

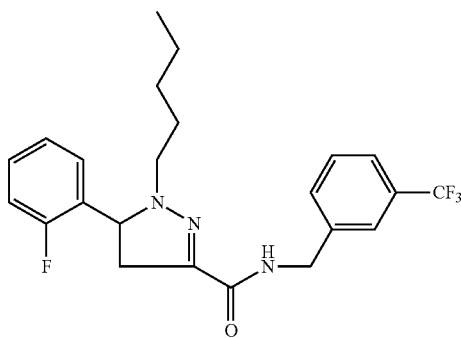

N-[3-(Trifluoromethyl)benzyl]-1-(n-pentyl)-5-(2-fluorophenyl)-4,5-dihydro-(1H)-pyrazole-3-carboxamide $^1$H-NMR (400 MHz, CDCl$_3$) δ 0.80-0.88 (m, 3H), 1.16-1.33 (m, 4H), 1.53-1.69 (m, 2H), 2.85 (dd, J=17.3 and 13.7 Hz, 1H), 2.90-3.03 (m, 2H), 3.51 (dd, J=17.1 and 11.7 Hz, 1H), 4.56-4.64 (m, 2H), 4.81 (dd, J=13.8 and 11.7 Hz, 1H), 7.02-7.10 (m, 2H), 7.16 (t, J=7.5 Hz, 1H), 7.25-7.33 (m, 1H), 7.43-7.50 (m, 2H), 7.52-7.57 (m, 2H), 7.58 (br s, 1H).

Compound 87

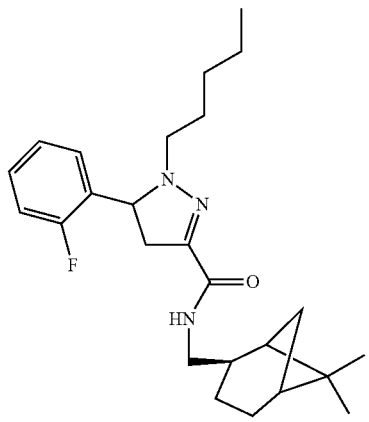

N-[(1R,2S,5R)-rel-6,6-dimethylbicyclo[3.1.1.]heptan-2-methyl]-1-(n-pentyl)-5-(2-fluorophenyl)-4,5-dihydro-(1H)-pyrazole-3-carboxamide (mixture of diastereoisomers) (from (−)-cis-myrtanylamine (CAS 38235-68-6))

$^1$H-NMR (400 MHz, CDCl$_3$) δ 0.84-0.93 (m, 4H), 1.06 (s, 3H), 1.21 (d, J=2.4 Hz, 3H), 1.22-1.34 (m, 4H), 1.48-1.69 (m, 3H), 1.82-2.03 (m, 5H), 2.22-2.32 (m, 1H), 2.34-2.42 (m, 1H), 2.75-2.85 (m, 1H), 2.88-3.01 (m, 2H), 3.28-3.41 (m, 2H), 3.43-3.53 (m, 1H), 4.74 (dd, J=13.8 and 11.4 Hz, 1H), 6.64 (br t, J=6.3 Hz, 1H), 7.02-7.08 (m, 1H), 7.15 (t, J=7.5 Hz, 1H), 7.24-7.31 (m, 1H), 7.45-7.51 (m, 1H).

Compound 88

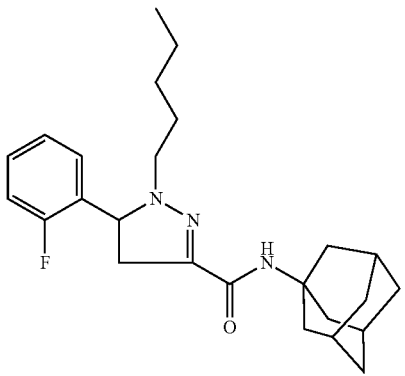

N-(Adamant-1-yl)-1-(n-pentyl)-5-(2-fluorophenyl)-4,5-dihydro-(1H)-pyrazole-3-carboxamide $^1$H-NMR (400 MHz, CDCl$_3$) δ 0.86 (t, J=7.1 Hz, 3H), 1.18-1.35 (m, 4H), 1.52-1.75 (m, 8H), 2.05-2.13 (m, 9H), 2.75 (dd, J=17.3 and 14 Hz, 1H), 2.92 (t, J=7.4 Hz, 2H), 3.44 (dd, J=17.3 and 11.3 Hz, 1H), 4.69 (dd, J=14 and 11.3 Hz, 1H), 6.39 (br s, 1H), 7.01-7.08 (m, 1H), 7.15 (t, J=7.4 Hz, 1H), 7.23-7.31 (m, 1H), 7.45-7.51 (m, 1H).

Compound 89

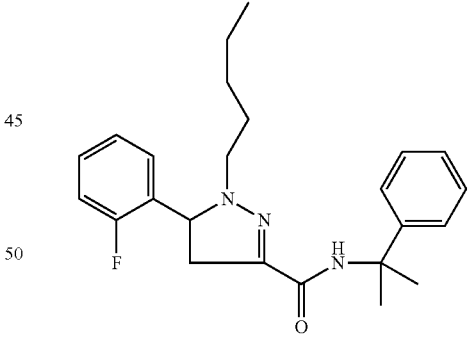

N-[1-phenyl-1-methyl-ethyl]-1-(n-pentyl)-5-(2-fluorophenyl)-4,5-dihydro-(1H)-pyrazole-3-carboxamide $^1$H-NMR (400 MHz, CDCl$_3$) δ 0.86 (t, J=6.9 Hz, 3H), 1.19-1.35 (m, 4H), 1.55-1.70 (m, 2H), 1.76 (s, 3H), 1.77 (s, 3H), 2.76 (dd, J=17.5 and 13.8 Hz, 1H), 2.91-2.99 (m, 2H), 3.42 (dd, J=17.3 and 11.3 Hz, 1H), 4.72 (dd, J=14 and 11.3 Hz, 1H), 6.96 (br s, 1H), 7.01-7.07 (m, 1H), 7.15 (t, J=7.4 Hz, 1H), 7.20-7.30 (m, 2H), 7.34 (t, J=7.7 Hz, 2H), 7.42-7.52 (m, 3H).

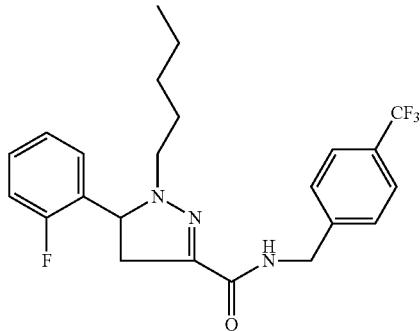

Compound 90

N-[4-(Trifluoromethyl)benzyl]-1-(n-pentyl)-5-(2-fluorophenyl)-4,5-dihydro-(1H)-pyrazole-3-carboxamide $^1$H-NMR (400 MHz, CDCl$_3$) δ 0.85 (t, J=6.9 Hz, 3H), 1.15-1.34 (m, 4H), 1.53-1.69 (m, 2H), 2.85 (dd, J=17.3 and 13.7 Hz, 1H), 2.90-3.03 (m, 2H), 3.51 (dd, J=17.3 and 11.6 Hz, 1H), 4.54-4.64 (m, 2H), 4.79 (dd, J=13.8 and 11.4 Hz, 1H), 6.98-7.10 (m, 2H), 7.16 (t, J=7.5 Hz, 1H), 7.24-7.33 (m, 1H), 7.43-7.50 (m, 3H), 7.60 (d, J=8.1 Hz, 2H).

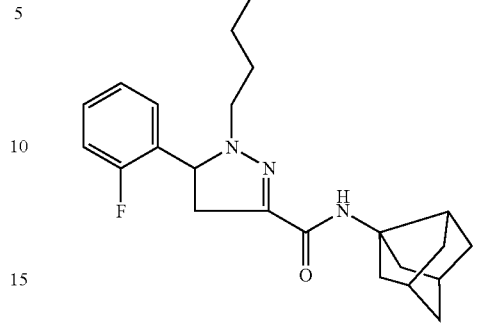

Compound 92

N-(Noradamant-1-yl)-1-(n-pentyl)-5-(2-fluorophenyl)-4,5-dihydro-(1H)-pyrazole-3-carboxamide $^1$H-NMR (400 MHz, CDCl$_3$) δ 0.83-0.90 (m, 3H), 1.17-1.35 (m, 4H), 1.51-1.71 (m, 6H), 1.91-1.98 (m, 2H), 2.01-2.10 (m, 2H), 2.10-2.19 (m, 2H), 2.29 (br s, 2H), 2.50 (br t, J=6.8 Hz, 1H), 2.79 (dd, J=17.4 and 13.8 Hz, 1H), 2.93 (t, J=7.2 Hz, 2H), 3.46 (dd, J=17.3 and 11.3 Hz, 1H), 4.72 (dd, J=14 and 11.3 Hz, 1H), 6.79 (br s, 1H), 7.05 (ddd, J=10.2, 8.1 and 1.2 Hz, 1H), 7.15 (br t, J=6.9 Hz, 1H), 7.24-7.32 (m, 1H), 7.48 (dt, J=7.5 and 2.1 Hz, 1H).

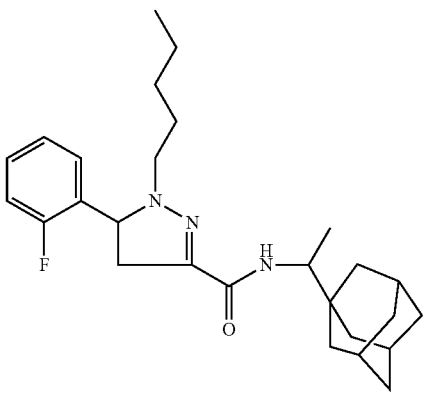

Compound 91

N-[1-(Adamant-1-yl)-ethyl]-1-(n-pentyl)-5-(2-fluorophenyl)-4,5-dihydro-(1H)-pyrazole-3-carboxamide (diastereomeric mixture)

$^1$H-NMR (400 MHz, CDCl$_3$) δ 0.83-0.90 (m, 3H), 1.06-1.13 (m, 3H), 1.20-1.36 (m, 4H), 1.49-1.77 (m, 14H), 1.98-2.04 (m, 3H), 2.81 (dd, J=17.3 and 14 Hz, 1H), 2.89-3.03 (m, 2H), 3.49 (dd, J=17.1 and 11.1 Hz, 1H), 3.72-3.82 (m, 1H), 4.68-4.79 (m, 1H), 6.51 (br d, J=10.2 Hz, 1H), 7.01-7.09 (m, 1H), 7.12-7.19 (m, 1H), 7.24-7.31 (m, 1H), 7.46-7.55 (m, 1H).

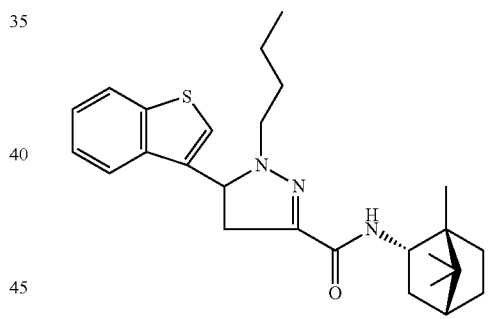

Compound 93 diastereomer 1

N-[endo-(1R,2S,4R)-1,7,7-trimethylbicyclo[2.2.1]hept-2-yl]-1-(n-butyl)-5-(benzothien-3-yl)-4,5-dihydro-(1H)-pyrazole-3-carboxamide (diastereomer 1)

Compounds 93 and 94 were obtained from the corresponding diasteromeric mixture via a Sepacore column (40×150 mm) chromatographic purification. Eluant gradient: petroleum ether (40-60)/diethyl ether=90/10=>petroleum ether (40-60)/diethyl ether=80/20 (v/v)). Compound 93: first (fastest) eluting diastereomer: Compound 94: second (slowest) eluting diastereomer:

$^1$H-NMR (400 MHz, CDCl$_3$) δ 0.82-1.02, (m, 13H), 1.20-1.49 (m, 4H), 1.59-1.67 (m, 3H), 1.70 (t, J=4.5 Hz, 1H), 1.75-1.87 (m, 1H), 2.38 (m, 1H), 2.91-3.11 (m, 3H), 3.51 (dd, J=17.4 and 11.4 Hz, 1H), 4.38-4.48 (m, 1H), 4.80 (dd, J=14.4 and 11.4 Hz, 1H), 6.71 (br d, J=9.3 Hz, 1H), 7.37 (dd, J=6.2 and 3.2 Hz, 2H), 7.40 (s, 1H), 7.75-7.81 (m, 1H), 7.86-7.91 (m, 1H).

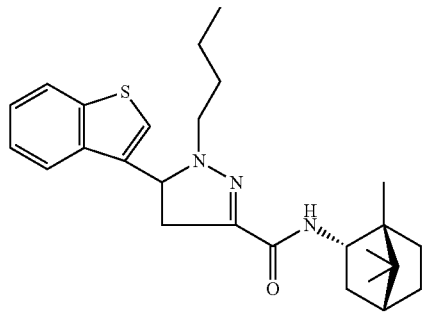

Compound 94 diastereomer 2

N-[endo-(1R,2S,4R)-1,7,7-trimethylbicyclo[2.2.1]hept-2-yl]-1-(n-butyl)-5-(benzothien-3-yl)-4,5-dihydro-(1H)-pyrazole-3-carboxamide (diastereomer 2)

$^1$H-NMR (400 MHz, CDCl$_3$) δ 0.82-1.03 (m, 13H), 1.20-1.51 (m, 4H). 1.62-1.68 (m, 3H), 1.70 (t, J=4.4 Hz, 1H), 1.76-1.88 (m, 1H), 2.34-2.47 (m, 1H), 2.90-3.11 (m, 3H), 3.50 (dd, J=17.3 and 11.3 Hz, 1H), 4.27-4.37 (m, 1H), 4.78 (dd, J=14.4 and 11.4 Hz, 1H), 6.71 (br d, J=9 Hz, 1H), 7.35-7.45 (m, 3H), 7.77-7.83 (m, 1H), 7.86-7.92 (m, 1H).

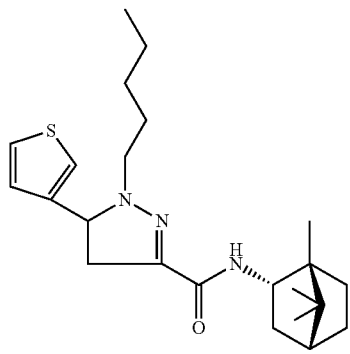

Compound 95

N-[endo-(1R,2S,4R)-1,7,7-trimethylbicyclo[2.2.1]hept-2-yl]-1-(n-pentyl)-5-(thien-3-yl)-4,5-dihydro-(1H)-pyrazole-3-carboxamide (diastereomeric mixture)

$^1$H-NMR (400 MHz, CDCl$_3$) δ 0.83-0.93 (m, 10H), 0.97 (s, 3H), 1.20-1.34 (m, 5H), 1.36-1.46 (m, 1H), 1.54-1.65 (m, 3H), 1.69 (t, J=4.5 Hz, 1H), 1.73-1.86 (m, 1H), 2.32-2.42 (m, 1H), 2.80-2.90 (m, 1H), 2.90-3.04 (m, 2H), 3.31-3.41 (m, 1H), 4.26-4.34 (m, 1H), 4.46-4.56 (m, 1H), 6.66 (br d, J=9 Hz, 1H), 7.08-7.13 (m, 1H), 7.18-7.22 (m, 1H), 7.31-7.35 (m, 1H).

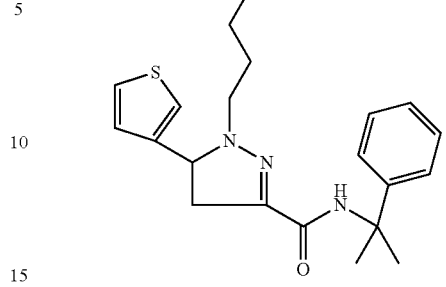

Compound 96

N-(1-phenyl-1-methyl-ethyl)-1-(n-pentyl)-5-(thien-3-yl)-4,5-dihydro-(1H)-pyrazole-3-carboxamide $^1$H-NMR (400 MHz, CDCl$_3$) δ 0.83-0.90 (m, 3H), 1.20-1.33 (m, 4H), 1.53-1.68 (m, 2H), 1.76 (s, 3H), 1.77 (s, 3H), 2.80 (dd, J=17.1 and 14.1 Hz, 1H), 2.87-3.01 (m, 2H), 3.29 (dd, J=17.1 and 10.8 Hz, 1H), 4.49 (dd, J=14.1 and 10.8 Hz, 1H), 6.96 (br s, 1H), 7.08-7.12 (m, 1H), 7.18-7.21 (m, 1H), 7.23 (br t, J=7.2 Hz, 1H), 7.30-7.38 (m, 3H), 7.45 (br d, J=7.2 Hz, 2H).

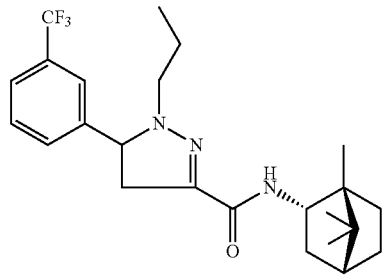

Compound 97 diastereomer 1

N-[endo-(1R,2S,4R)-1,7,7-trimethylbicyclo[2.2.1]hept-2-yl]-1-(n-propyl)-5-(3-(trifluoromethyl)phenyl)-4,5-dihydro-(1H)-pyrazole-3-carboxamide (diastereomer 1)

Compounds 97 and 98 were obtained from the corresponding diasteromeric mixture via a Sepacore column (40×150 mm) chromatographic purification. Eluant gradient: petroleum ether (40-60)/diethyl ether=90/10=>petroleum ether (40-60)/diethyl ether=60/40 (v/v)). Compound 97: second (slowest) eluting diastereomer: Compound 98: first (fastest) eluting diastereomer.

$^1$H-NMR (400 MHz, CDCl$_3$) δ 0.84-0.93 (m, 10H), 0.97 (s, 3H), 1.21-1.30 (m, 1H), 1.38-1.47 (m, 1H), 1.56-1.68 (m, 3H), 1.70 (t, J=4.4 Hz, 1H), 1.76-1.86 (m, 1H), 2.33-2.43 (m, 1H), 2.80 (dd, J=17.4 and 14.4 Hz, 1H), 2.82-2.98 (m, 2H), 3.46 (dd, J=17.4 and 11.1 Hz, 1H), 4.26-4.34 (m, 1H), 4.45 (dd, J=14.4 and 11.1 Hz, 1H), 6.67 (br d, J=9.1 Hz, 1H), 7.46-7.51 (m, 1H), 7.55-7.61 (m, 2 H), 7.67 (br s, 1H).

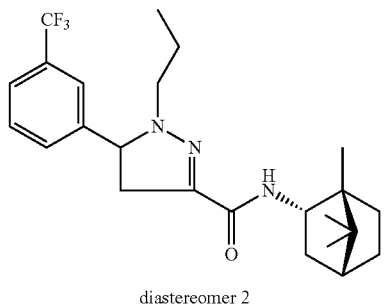

Compound 98 diastereomer 2

N-[endo-(1R,2S,4R)-1,7,7-trimethylbicyclo[2.2.1]hept-2-yl]-1-(n-propyl)-5-(3-(trifluoromethyl)phenyl)-4,5-dihydro-(1H)-pyrazole-3-carboxamide (diastereomer 2)

¹H-NMR (400 MHz, CDCl₃) δ 0.82-0.94 (m, 10H), 0.97 (s, 3H), 1.20-1.35 (m, 1H), 1.38-1.48 (m, 1H), 1.54-1.67 (m, 3H), 1.69 (t, J=4.4 Hz, 1H), 1.75-1.86 (m, 1H), 2.33-2.42 (m, 1H), 2.79 (dd, J=17.3 and 14.3 Hz, 1H), 2.85-3.00 (m, 2H), 3.48 (dd, J=17.4 and 11.4 Hz, 1H), 4.25-4.35 (m, 1H), 4.47 (dd, J=14.1 and 11.1 Hz, 1H), 6.68 (br d, J=9.1 Hz, 1H), 7.46-7.51 (m, 1H), 7.55-7.60 (m, 2H), 7.65 (br s, 1H).

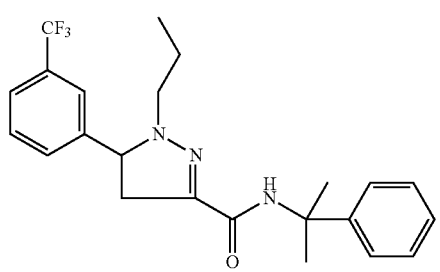

Compound 99

N-(1-phenyl-1-methyl-ethyl)-1-(n-propyl)-5-(3-(trifluoromethyl)phenyl)-4,5-dihydro-(1H)-pyrazole-3-carboxamide ¹H-NMR (400 MHz, CDCl₃) δ 0.88 (t, J=7.4 Hz, 3H), 1.55-1.71 (m, 2H), 1.76 (s, 3H), 1.77 (s, 3H), 2.75 (dd, J=17.4 and 14.4 Hz, 1H), 2.80-2.98 (m, 2H), 3.41 (dd, J=17.4 and 11.1 Hz, 1H), 4.44 (dd, J=14.4 and 11.1 Hz, 1H), 6.97 (br s, 1H), 7.21-7.27 (m, 1H), 7.35 (br t, J=7.7 Hz, 2H), 7.43-7.52 (m, 3H), 7.55-7.60 (m, 2H), 7.65 (br s, 1H).

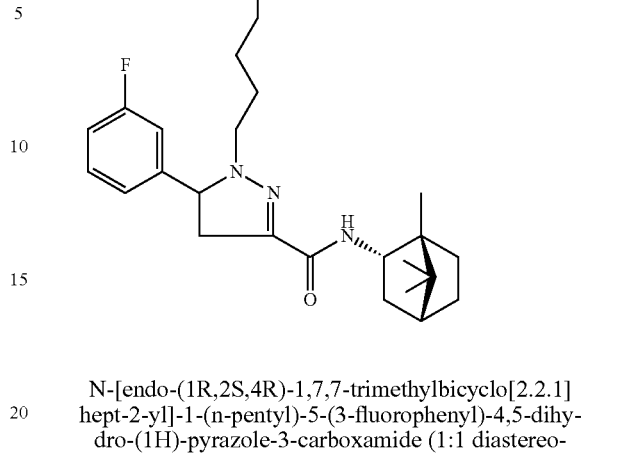

Compound 100

N-[endo-(1R,2S,4R)-1,7,7-trimethylbicyclo[2.2.1]hept-2-yl]-1-(n-pentyl)-5-(3-fluorophenyl)-4,5-dihydro-(1H)-pyrazole-3-carboxamide (1:1 diastereomeric mixture)

¹H-NMR (400 MHz, CDCl₃) δ 0.81-0.94 (m, 10H), 0.97 (s, 3H), 1.20-1.35 (m, 5H), 1.37-1.47 (m, 1H), 1.54-1.65 (m, 3H), 1.67-1.72 (m, 1H), 1.75-1.87 (m, 1H), 2.32-2.42 (m, 1H), 2.73-2.84 (m, 1H), 2.91-2.99 (m, 2H), 3.38-3.49 (m, 1H), 4.26-4.45 (m, 2H), 6.66 (br d, J=6.6 Hz, 1H), 7.00 (dt, J=8.4 and 2.4 Hz, 1H), 7.08-7.17 (m, 2H), 7.28-7.35 (m, 1H).

Compound 101

N-[endo-(1R,2S,4R)-1,7,7-trimethylbicyclo[2.2.1]hept-2-yl]-1-(n-pentyl)-5-(2-fluorophenyl)-4,5-dihydro-(1H)-pyrazole-3-carboxamide (diastereomeric mixture)

To a magnetically stirred solution of E-2-oxo-4-(2-fluorophenyl)-but-3-enoic acid [endo-(1R,2S,4R)-1,7,7-trimethylbicyclo[2.2.1]hept-2-ylamide] (Intermediate X-3) (1.5 g, 4.83 mmol) in ethanol (50 ml) was successively added acetic acid (660 ml, 11.58 mmol) and n-pentylhydrazine (Intermediate XI-1) (1.45 ml, 9.65 mmol) and the resulting mixture was reacted in a nitrogen atmosphere at 60° C. for 8 hours in an oil bath. The reaction mixture was allowed to attain room temperature and concentrated in vacuo. The residue was dissolved in dichloromethane, washed with water and subsequently dried over MgSO₄, filtered and concentrated in vacuo. Further chromatographic purification using Sepacore equipment (eluant: petroleum ether/ethylacetate=95/5 (v/v)) gave compound 101 (940 mg, 46% yield) as an oil.

¹H-NMR (400 MHz, CDCl₃) δ 0.83-0.94 (m, 10H), 1.20-1.85 (m, 14H), 2.32-2.42 (m, 1H), 2.74-2.85 (m, 1H), 2.91-3.02 (m, 2H), 3.43-3.54 (m, 1H), 4.26-4.36 (m, 1H), 4.69-4.80 (m, 1H), 6.63-6.70 (m, 1H), 7.02-7.09 (m, 1H), 7.12-7.19 (m, 1H), 7.25-7.31 (m, 1H), 7.46-7.54 (m, 1H).

Compound 102

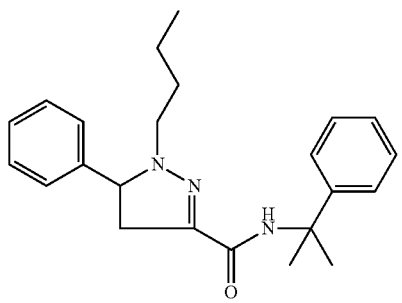

N-(1-phenyl-1-methyl-ethyl)-1-(n-butyl)-5-phenyl-4,5-dihydro-(1H)-pyrazole-3-carboxamide Compound 102 was obtained from E-2-oxo-4-phenyl-but-3-enoic acid [1-phenyl-1-methyl-ethyl]amide and n-butylhydrazine analogously to the procedure described for compound 101.

¹H-NMR (400 MHz, CDCl₃) δ 0.85 (t, J=7, 3H), 1.20-1.39 (m, 2H), 1.53-1.63 (m, 2H), 1.76 (s, 3H), 1.77 (s, 3H), 2.77 (dd, J=17 and 14, 1H), 2.90-2.96 (m, 2H), 3.35 (dd, J=17 and 11, 1H), 4.37 (dd, J=14 and 11, 1H), 6.97 (br s, 1H), 7.21-7.48 (m, 10H).

Compound 103

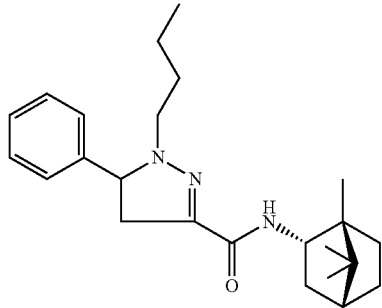

N-[endo-(1R,2S,4R)-1,7,7-trimethylbicyclo[2.2.1]hept-2-yl]-1-(n-butyl)-5-phenyl-4,5-dihydro-(1H)-pyrazole-3-carboxamide (diastereomeric mixture)

Compound 103 was obtained from E-2-oxo-4-phenyl-but-3-enoic acid [endo-(1R,2S,4R)-1,7,7-trimethylbicyclo[2.2.1]hept-2-ylamide] (Intermediate X-2) and n-butylhydrazine analogously to the procedure described for compound 101.

¹H-NMR (400 MHz, CDCl₃) δ 0.83-0.95 (m, 10H), 0.97 (s, 3H), 1.21-1.86 (m, 9H), 2.32-2.42 (m, 1H), 2.77-2.88 (m, 1H), 2.91-2.99 (m, 2H), 3.35-3.46 (m, 1H), 4.26-4.46 (m, 2H), 6.66 (br d, J~8, 1H), 7.28-7.40 (m, 5H).

Compound 104

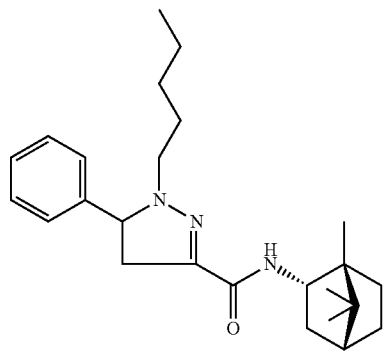

N-[endo-(1R,2S,4R)-1,7,7-trimethylbicyclo[2.2.1]hept-2-yl]-1-(n-pentyl)-5-phenyl-4,5-dihydro-(1H)-pyrazole-3-carboxamide (diastereomeric mixture)

Compound 104 was obtained from E-2-oxo-4-phenyl-but-3-enoic acid [endo-(1R,2S,4R)-1,7,7-trimethylbicyclo[2.2.1]hept-2-ylamide] (Intermediate X-2) and n-pentylhydrazine (Intermediate XI-1) analogously to the procedure described for compound 101.

¹H-NMR (400 MHz, CDCl₃) δ 0.83-0.94 (m, 10H), 0.97 (s, 3H), 1.20-1.47 (m, 5H), 1.54-1.65 (m, 3H), 1.69 (t, J~6, 1H), 1.75-1.85 (m, 1H), 2.32-2.42 (m, 1H), 2.82 (dd, J=17 and 14, 1H), 2.92-2.98 (m, 2H), 3.41 (dd, J=17 and 11, 1H), 4.26-4.35 (m, 1H), 4.41 (dd, J=14 and 11, 1H), 6.67 (br d, J~8, 1H), 7.28-7.39 (m, 5H).

Compound 105

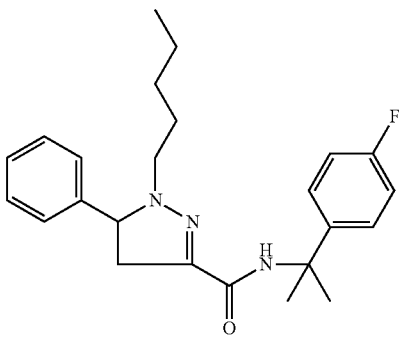

N-(1-(4-fluorophenyl)-1-methyl-ethyl)-1-(n-pentyl)-5-phenyl-4,5-dihydro-(1H)-pyrazole-3-carboxamide Compound 6 was obtained from E-2-oxo-4-phenyl-but-3-enoic acid [1-(4-fluorophenyl)-1-methyl-ethyl]amide and n-pentylhydrazine (Intermediate XI-1) analogously to the method described for compound 101.

¹H-NMR (400 MHz, CDCl₃) δ 0.85 (t, J=7, 3H), 1.20-1.31 (m, 4H), 1.54-1.67 (m, 2H), 1.74 (s, 3H), 1.75 (s, 3H), 2.77 (dd, J=17 and 14, 1H), 2.90-2.97 (m, 2H), 3.35 (dd, J=17 and 11, 1H), 4.38 (dd, J=14 and 11, 1H), 6.94 (br s, 1H), 6.98-7.04 (m, 2H), 7.27-7.43 (m, 7H).

Compound 106

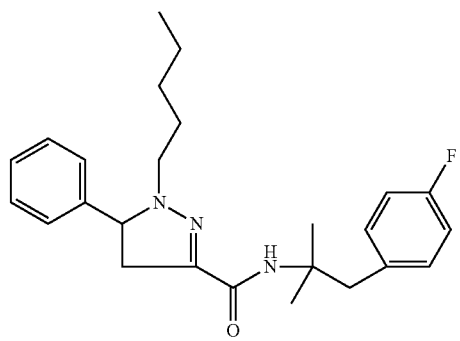

N-(2-(4-fluorophenyl)-1,1-dimethyl-ethyl)-1-(n-pentyl)-5-phenyl-4,5-dihydro-(1H)-pyrazole-3-carboxamide Compound 106 was obtained from E-2-oxo-4-phenyl-but-3-enoic acid [2-(4-fluorophenyl)-2,2-dimethyl-ethyl]amide (Intermediate X-4) and n-pentylhydrazine (Intermediate XI-1) analogously to the procedure described for compound 101.

¹H-NMR (400 MHz, CDCl₃) δ 0.85 (t, J=7, 3H), 1.16-1.27 (m, 4H), 1.36 (s, 3H), 1.39 (s, 3H), 1.50-1.62 (m, 2H), 2.77-2.94 (m, 4H), 3.04 (d, J=13, 1H), 3.10 (d, J=13, 1H), 3.41 (dd, J=18 and 12, 1H), 4.39 (dd, J=14 and 11, 1H), 6.38 (br s, 1H), 6.94-7.01 (m, 2H), 7.10-7.16 (m, 2H), 7.28-7.38 (m, 5H).

Furthermore, the compounds 107-118 were obtained analogously to the method described for compound 101.

Compound 107

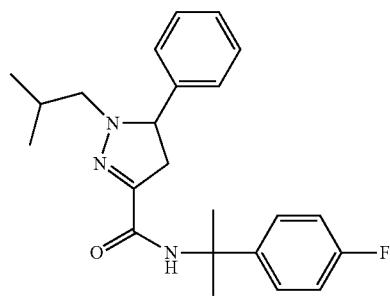

N-[1-(4-fluorophenyl)-1-methyl-ethyl]-1-isobutyl-5-phenyl-4,5-dihydro-(1H)-pyrazole-3-carboxamide ¹H-NMR (400 MHz, CDCl₃) δ 0.85 (d, J=6.6 Hz, 3H), 0.88 (d, J=6.6 Hz, 3H), 1.73 (s, 3H), 1.75 (s, 3H), 1.96-2.07 (m, 1H), 2.54 (dd, J=12.6 and 9 Hz, 1H), 2.77 (dd, J=17.4 and 14.1 Hz, 1H), 2.84 (dd, J=12.6 and 5.1 Hz, 1H), 3.34 (dd, J=17.4 and 11.1 Hz, 1H), 4.34 (dd, J=14.4 and 11.1 Hz, 1H), 6.93 (br s, 1H), 7.01 (t, J=8.9 Hz, 2H), 7.27-7.37 (m, 5H), 7.38-7.44 (m, 2H).

Compound 108

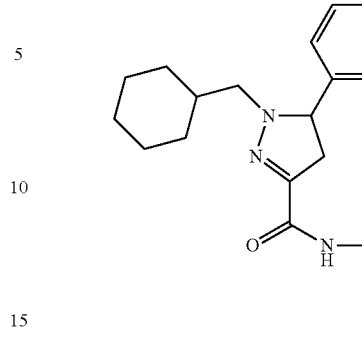

N-[1-(4-fluorophenyl)-1-methyl-ethyl]-1-cyclohexyl-methyl-5-phenyl-4,5-dihydro-(1H)-pyrazole-3-carboxamide ¹H-NMR (400 MHz, CDCl₃) δ 0.67-0.90 (m, 2H), 1.05-1.29 (m, 4H), 1.51-1.72 (m, 4H), 1.74 (s, 3H), 1.75 (s, 3H), 1.82-1.90 (m, 1H), 2.61 (dd, J=12.8 and 8.9 Hz, 1H), 2.76 (dd, J=17.3 and 14.3 Hz, 1H), 2.83 (dd, J=12.6 and 5.1 Hz, 1H), 3.33 (dd, J=17.3 and 11 Hz, 1H), 4.33 (dd, J=14.4 and 11.1 Hz, 1H), 6.93 (br s, 1H), 7.01 (t, J=8.7 Hz, 2H), 7.27-7.37 (m, 5H), 7.39-7.43 (m, 2H).

Compound 109

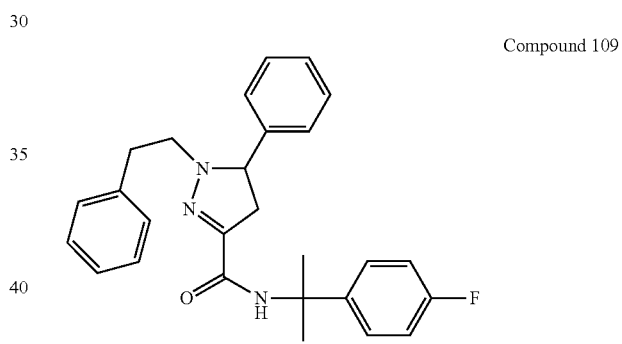

N-[1-(4-fluorophenyl)-1-methyl-ethyl]-1-phenethyl-5-phenyl-4,5-dihydro-(1H)-pyrazole-3-carboxamide ¹H-NMR (400 MHz, CDCl₃) δ 1.74 (s, 3H), 1.75 (s, 3H), 2.77 (dd, J=17.4 and 14.4 Hz, 1H), 2.84-2.93 (m, 1H), 2.95-3.03 (m, 1H), 3.13-3.29 (m, 2H), 3.33 (dd, J=17.4 and 11.1 Hz, 1H), 4.43 (dd, J=14.4 and 11.1 Hz, 1H), 6.91 (br s, 1H), 7.02 (t, J=8.7 Hz, 2H), 7.14 (d, J=6.9 Hz, 2H), 7.16-7.35 (m, 8H), 7.38-7.44 (m, 2H).

Compound 110

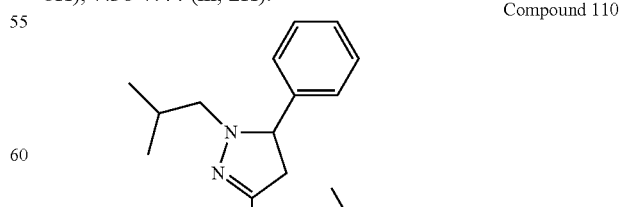

N-[endo-(1R,2S,4R)-1,7,7-trimethylbicyclo[2.2.1]
hept-2-yl]-1-isobutyl-5-phenyl-4,5-dihydro-(1H)-
pyrazole-3-carboxamide (diastereomeric mixture)

$^1$H-NMR (400 MHz, DMSO-$d_6$) δ 0.81-0.95 (m, 13H), 0.96 (s, 3H), 1.22-1.30 (m, 1H), 1.37-1.47 (m, 1H), 1.55-1.67 (m, 1H), 1.69 (t, J=4.5 Hz, 1H), 1.75-1.85 (m, 1H), 1.96-2.08 (m, 1H), 2.32-2.43 (m, 1H), 2.52-2.60 (m, 1H), 2.78-2.88 (m, 2H), 3.36-3.46 (m, 1H), 4.26-4.41 (m, 2H), 6.67 (br d, J~8 Hz, 1H), 7.27-7.40 (m, 5H).

Compound 111

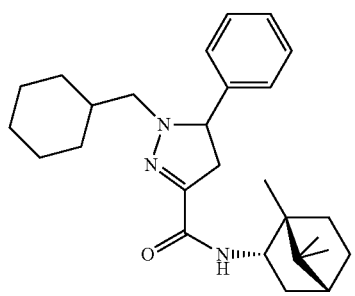

N-[endo-(1R,2S,4R)-1,7,7-trimethylbicyclo[2.2.1]
hept-2-yl]-1-cyclohexylmethyl-5-phenyl-4,5-dihy-
dro-(1H)-pyrazole-3-carboxamide (diastereomeric
mixture)

$^1$H-NMR (400 MHz, DMSO-$d_6$) δ 0.70-0.95 (m, 9H), 0.98 (s, 3H), 1.04-1.32 (m, 5H), 1.37-1.48 (m, 1H), 1.55-1.90 (m, 8H), 2.32-2.43 (m, 1H), 2.60-2.70 (m, 1H), 2.77-2.89 (m, 2H), 3.35-3.46 (m, 1H), 4.26-4.42 (m, 2H), 6.65 (br d, J~9 Hz, 1H), 7.27-7.39 (m, 5H).

Compound 112

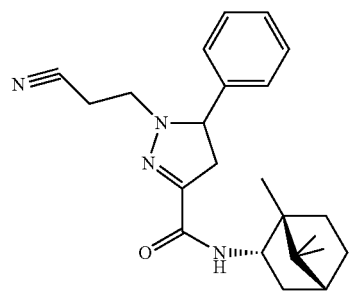

N-[endo-(1R,2S,4R)-1,7,7-trimethylbicyclo[2.2.1]
hept-2-yl]-1-(2-cyano-ethyl)-5-phenyl-4,5-dihydro-
(1H)-pyrazole-3-carboxamide (diastereomeric mix-
ture)

$^1$H-NMR (400 MHz, DMSO-$d_6$) δ 0.82-0.95 (m, 7H), 0.97 (s, 3H), 1.22-1.32 (m, 1H), 1.38-1.49 (m, 1H), 1.54-1.65 (m, 1H), 1.70 (t, J=4.7 Hz, 1H), 1.75-1.88 (m, 1H), 2.34-2.44 (m, 1H), 2.61-2.77 (m, 2H), 2.88 (dd, J=17.6 and 14.3 Hz, 1H), 3.20 (t, J=6.8 Hz, 2H), 3.46 (dd, J=17.4 and 10.8 Hz, 1H), 4.26-4.35 (m, 1H), 4.39 (dd, J=14.4 and 10.8 Hz, 1H), 6.67 (br d, J=9 Hz, 1H), 7.31-7.44 (m, 5H).

Compound 113

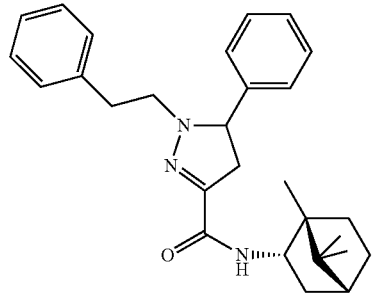

N-[endo-(1R,2S,4R)-1,7,7-trimethylbicyclo[2.2.1]
hept-2-yl]-1-phenethyl-5-phenyl-4,5-dihydro-(1H)-
pyrazole-3-carboxamide (diastereomeric mixture)

$^1$H-NMR (400 MHz, DMSO-$d_6$) δ 0.85-0.96 (m, 7H), 0.98 (s, 3H), 1.20-1.32 (m, 1H), 1.39-1.48 (m, 1H), 1.55-1.65 (m, 1H) 1.70 (t, J=4.5 Hz, 1H), 1.76-1.88 (m, 1H) 2.33-2.43 (m, 1H), 2.77-2.93 (m, 2H), 2.95-3.04 (m, 1H), 3.16-3.30 (m, 2H), 3.42 (dd, J=17.4 and 11.1 Hz, 1H), 4.26-4.35 (m, 1H), 4.45 (dd, J=14.4 and 11.1 Hz, 1H), 6.65 (br d, J=9.3 Hz, 1H), 7.10-7.40 (m, 10H).

Compound 114

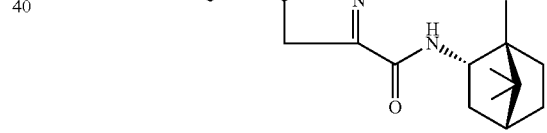

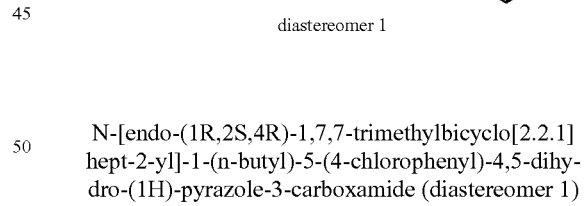

diastereomer 1

N-[endo-(1R,2S,4R)-1,7,7-trimethylbicyclo[2.2.1]
hept-2-yl]-1-(n-butyl)-5-(4-chlorophenyl)-4,5-dihy-
dro-(1H)-pyrazole-3-carboxamide (diastereomer 1)

Compounds 114 and 115 were obtained from the corresponding diasteromeric mixture via a flash chromatographic purification. Eluant: petroleum ether (40-60)/diethyl ether=75/25. Compound 115: first (fastest) eluting diastereomer: Compound 114: second (slowest) eluting diastereomer.

$^1$H-NMR (400 MHz, CDCl$_3$) δ 0.81-0.93 (m, 10H), 0.97 (s, 3H), 1.08-1.65 (m, 7H), 1.69 (t, J=4.5 Hz, 1H), 1.74-1.85 (m, 1H), 2.33-2.42 (m, 1H), 2.78 (dd, J=17.1 and 14.4 Hz, 1H), 2.92 (t, J=7.4 Hz, 2H), 3.40 (dd, J=17.4 and 11.1 Hz, 1H), 4.26-4.34 (m, 1H), 4.36 (dd, J=14.4 and 11.1 Hz, 1H), 6.65 (br d, J=9.3 Hz, 1H), 7.33 (s, 4H).

Compound 115

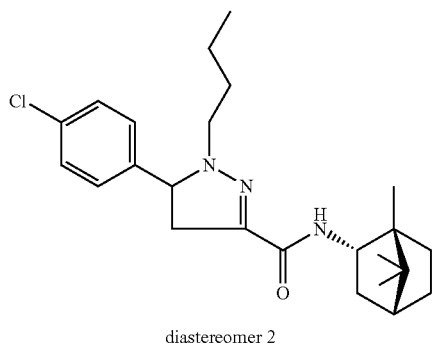

diastereomer 2

N-[endo-(1R,2S,4R)-1,7,7-trimethylbicyclo[2.2.1]
hept-2-yl]-1-(n-butyl)-5-(4-chlorophenyl)-4,5-dihydro-(1H)-pyrazole-3-carboxamide (diastereomer 2)

$^1$H-NMR (400 MHz, CDCl$_3$) δ 0.82-0.93 (m, 10H), 0.97 (s, 3H), 1.18-1.63 (m, 7H), 1.69 (t, J=4.5 Hz, 1H), 1.75-1.85 (m, 1H), 2.32-2.42 (m, 1H), 2.77 (dd, J=17.3 and 14.3 Hz, 1H), 2.93 (t, J=7.4 Hz, 2H), 3.37-3.46 (m, 1H), 4.26-4.34 (m, 1H), 4.38 (dd, J=14.1 and 11.1 Hz, 1H), 6.66 (br d, J=9.3 Hz, 1H), 7.29-7.35 (m, 4H).

Compound 116

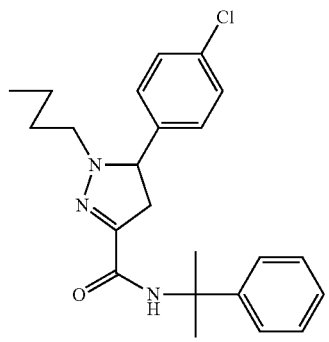

N-[1-phenyl-1-methyl-ethyl]-1-n-butyl-5-(4-chlorophenyl)-4,5-dihydro-(1H)-pyrazole-3-carboxamide $^1$H-NMR (400 MHz, CDCl$_3$) δ 0.86 (t, J=7.4 Hz, 3H), 1.20-1.38 (m, 2H), 1.53-1.63 (m, 2H), 1.76 (s, 3H), 1.77 (s, 3H), 2.72 (dd, J=17.3 and 14.3 Hz, 1H), 2.90 (t, J=7.4 Hz, 2H), 3.34 (dd, J=17.4 and 11.1 Hz, 1H), 4.34 (dd, J=14.4 and 11.1 Hz, 1H), 6.95 (br s, 1H), 7.20-7.26 (m, 1H), 7.28-7.37 (m, 6H), 7.45 (d, J=7.8 Hz, 2H).

Compound 117

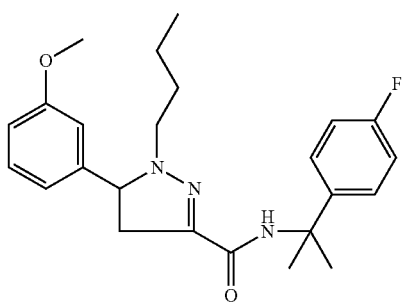

N-(1-(4-fluorophenyl)-1-methyl-ethyl)-1-(n-butyl)-5-(3-methoxyphenyl)-4,5-dihydro-(1H)-pyrazole-3-carboxamide $^1$H-NMR (400 MHz, CDCl$_3$) δ 0.85-0.89 (m, 3H), 1.22-1.39 (m, 2H), 1.55-1.66 (m, 2H), 1.73 (s, 3H), 1.74 (s, 3H), 2.76 (dd, J=17.3 and 14.5 Hz, 1H), 2.88-3.01 (m, 2H), 3.33 (dd, J=17.3 and 11.1 Hz, 1H), 3.80 (s, 3H), 4.35 (dd, J=14.5 and 11.1 Hz, 1H), 6.84 (ddd, J=8.12, 2.4 and 1.1 Hz, 1H), 6.91-6.96 (m, 3H), 6.97-7.05 (m, 2H), 7.23-7.28 (m, 1H), 7.38-7.44 (m, 2H).

Compound 118

N-[endo-(1R,2S,4R)-1,7,7-trimethylbicyclo[2.2.1]
hept-2-yl]-1-(n-butyl)-5-(3-methoxyphenyl)-4,5-dihydro-(1H)-pyrazole-3-carboxamide (1:1 diastereomeric mixture)

$^1$H-NMR (400 MHz, CDCl$_3$) δ 0.84-0.94 (m, 10H), 0.97 (s, 3H), 1.22-1.47 (m, 4H), 1.54-1.66 (m, 3H), 1.69 (t, J=4.4 Hz, 1H), 1.75-1.86 (m, 1H), 2.32-2.43 (m, 1H), 2.76-2.87 (m, 1H), 2.89-3.03 (m, 2H), 3.36-3.45 (m, 1H), 3.81/3.82 (double s, 3H), 4.26-4.43 (m, 2H), 6.63-6.71 (m, 1H), 6.81-6.87 (m, 1H), 6.92-6.97 (m, 2H), 7.23-7.30 (m, 1H).

Example 5

Pharmacological Methods

In Vitro Affinity for Cannabinoid-CB$_1$ Receptors

The affinity of the compounds of the invention for cannabinoid CB$_1$ receptors can be determined using membrane preparations of Chinese hamster ovary (CHO) cells in which the human cannabinoid CB$_1$ receptor is stably transfected in conjunction with [$^3$H]CP-55,940 as radioligand. After incubation of a freshly prepared cell membrane preparation with the [$^3$H]-ligand, with or without addition of one or more compounds of the invention, separation of bound and free ligand is performed by filtration over glassfiber filters. Radioactivity on the filter is measured by liquid scintillation counting.

In Vitro Affinity for Cannabinoid-CB$_2$ Receptors

The affinity of the compounds of the invention for cannabinoid CB$_2$ receptors can be determined using membrane preparations of CHO cells in which the human cannabinoid CB$_2$ receptor is stably transfected in conjunction with [$^3$H] CP-55,940 as radioligand. After incubation of a freshly prepared cell membrane preparation with the [$^3$H]-ligand, with or without addition of one or more compounds of the invention, separation of bound and free ligand is performed by filtration over glassfiber filters. Radioactivity on the filter is measured by liquid scintillation counting.

In Vitro Cannabinoid-$CB_1$ Receptor (Ant)Agonism

In vitro $CB_1$ receptor antagonism/agonism can be assessed with the human $CB_1$ receptor cloned in CHO cells. CHO cells are grown in a Dulbecco's Modified Eagle's medium (DMEM) culture medium, supplemented with 10% heat-inactivated fetal calf serum. Medium is aspirated and replaced by DMEM, without fetal calf serum, but containing [$^3$H]-arachidonic acid and incubated overnight in a cell culture stove (5% $CO_2$/95% air; 37° C.; water-saturated atmosphere). During this period [$^3$H]-arachidonic acid is incorporated in membrane phospholipids. On the test day, medium is aspirated and cells are washed three times using 0.5 ml DMEM, containing 0.2% bovine serum albumin (BSA). $CB_1$ agonist stimulation leads to activation of $PLA_2$ followed by release of [$^3$H]-arachidonic acid into the medium. This $CB_1$ agonist-induced release is concentration-dependently antagonized by $CB_1$ receptor antagonists, such as for example rimonabant.

In Vitro Cannabinoid-$CB_2$ Receptor (Ant)Agonism

Functional activity at the cannabinoid $CB_2$ receptor was assessed using a forskolin-stimulated cAMP accumulation assay. The ability of compounds to stimulate and inhibit adenylate cyclase activity was assessed in Chinese ovarian hamster (CHO) $K_1$ cells expressing human CB2 (Euroscreen, Brussel) receptor. CHO cells were grown in a CHO-S-SFM-II culture medium, supplemented with 10% heat-inactivated foetal calf serum, 2 mM glutamine, 400 µg/ml Hygromycine B and 500 µg/ml G418 at 37° C. in 93% air/5% $CO_2$. For incubation with test compounds, confluent cultures grown in 24 well plates were used. Each condition or substance was routinely tested in quadruplicate. Cells were loaded with 1 mCi [$^3$H]-adenine in 0.5 ml medium per well. After 2 hours, cultures were washed with 0.5 ml PBS containing 1 mM IBMX and incubated for 20 minutes with 0.5 ml PBS containing 1 mM IBMX and $3\times10^{-7}$ M forskolin with or without the test compound. Antagonistic effects of test compounds were determined as inhibition of 0.1 µM JWH-133-decreased [$^3$H]cAMP formation. After aspiration the reaction was stopped with 1 ml trichloroacetic acid (5% w/v). The [$^3$H]-ATP and [$^3$H]-cAMP formed in the cellular extract were assayed as follows: a volume of 0.8 ml of the extract was passed over Dowex (50WX-4200-400 mesh) and aluminum oxide columns, eluted with water and 0.1M imidazole (pH=7.5). Eluates were mixed with 7 ml Ultima-Flo [AP] and the β-radioactivity was counted with a liquid scintillation counter. The conversion of [$^3$H]-ATP into [$^3$H]-cAMP was expressed as the ratio in percentage radioactivity in the cAMP fraction as compared to the combined radioactivity in both cAMP and ATP fractions, and basal activity was subtracted to correct for spontaneous activity. Reference compounds used to assess cannabinoid $CB_2$ receptor mediated adenylate cyclase activity were the full cannabinoid $CB_2$ receptor agonists JWH-133 (Huffman, 1999$^b$) and WIN 55,212-2 (Huffman, 1999$^a$), and the inverse agonist or antagonist SR-144528 (Rinaldi-Carmona, 1998). Compounds were studied in a concentration range of $10^{-10}$ M to $10^{-6}$ M. $pEC_{50}$ and the $pA_2$ were calculated according to Cheng-Prusoff equation (Cheng and Prusoff, 1973). Two independent experiments were performed in triplicate.

Example 6

Pharmaceutical Test Results

| | Affinity for $CB_1$- and $CB_2$- receptors, and in vitro agonistic activity on $CB_1$- receptors | | |
|---|---|---|---|
| | receptor binding | | Functional $CB_1$ assays |
| Cmp | Human $CB_1$ affinity $pK_i$ | Human $CB_2$ affinity $pK_i$ | Human $CB_1$ agonism $pEC_{50}$ |
| 1 | 8.1 | 8.3 | 8.1 |
| 4 | 7.5 | 7.1 | 7.4 |
| 7 | 6.9 | 6.3 | 6.2 |
| 12 | 7.1 | 7.4 | 7.4 |
| 14 | 7.5 | 6.6 | 6.3 |
| 22 | 7.2 | 6.5 | 7.1 |
| 27 | 7.8 | 8.1 | 7.9 |
| 28 | 8.2 | 7.0 | 8.1 |
| 32 | 8.1 | 8.0 | 7.4 |
| 37 | 7.8 | 7.0 | 8.1 |
| 101 | 8.2 | 8.1 | 8.2 |
| 102 | 7.4 | 7.4 | 7.0 |
| 103 | 7.1 | 7.6 | 7.5 |
| 104 | 8.2 | 7.6 | 8.5 |
| 105 | 7.8 | 6.9 | 8.8 |
| 108 | 7.6 | 7.5 | 7.8 |
| 110 | 7.3 | 7.3 | 6.5 |

The compounds of the invention have a high affinity for cannabinoid-$CB_1$ and $CB_2$ receptors, and are agonists on $CB_1$ receptors. Surprising, because 1,3,5-trisubstituted pyrazoline derivatives described in e.g., WO 2005/074920, WO 2005/077911 and WO 2007/009689, as cannabinoid $CB_1$ receptor 'modulating' agents, a definition embracing agonists, invariably were shown to be antagonists.

Example 7

Pharmaceutical Preparations

For clinical use, compounds of formula (I) can be formulated into pharmaceutical compositions that are important and novel embodiments of the invention because they contain the compounds, more particularly specific compounds disclosed herein. Types of pharmaceutical compositions that may be used include, but are not limited to, tablets, chewable tablets, capsules (including microcapsules), solutions, parenteral solutions, ointments (creams and gels), suppositories, suspensions, and other types disclosed herein or apparent to a person skilled in the art from the specification and general knowledge in the art. The active ingredient, for instance, may also be in the form of an inclusion complex in cyclodextrins, their ethers or their esters. The compositions are used for oral, intravenous, subcutaneous, tracheal, bronchial, intranasal, pulmonary, transdermal, buccal, rectal, parenteral or other ways to administer. The pharmaceutical formulation contains at least one compound of formula (I) in a mixture with a pharmaceutically acceptable adjuvant, diluent and/or carrier. In one embodiment, the total amount of active ingredients may be in amounts, for example, from about 0.1% (w/w) to about 95% (w/w) of the formulation, and from 0.5% to 50% (w/w), and further from 1% to 25% (w/w).

The compounds of the invention can be brought into forms suitable for administration by means of usual processes using auxiliary substances such as liquid or solid, powdered ingredients, such as the pharmaceutically customary liquid or solid fillers and extenders, solvents, emulsifiers, lubricants, flavorings, colorings and/or buffer substances. Frequently used auxiliary substances include magnesium carbonate, titanium dioxide, lactose, saccharose, sorbitol, mannitol and other sugars or sugar alcohols, talc, lactoprotein, gelatin, starch, amylopectin, cellulose and its derivatives, animal and vegetable oils such as fish liver oil, sunflower, groundnut or sesame oil, polyethylene glycol and solvents such as, for example, sterile water and mono- or polyhydric alcohols such as glycerol, as well as with disintegrating agents and lubricating agents such as magnesium stearate, calcium stearate, sodium stearyl fumarate and polyethylene glycol waxes. The mixture may then be processed into granules or pressed into tablets. A tablet is prepared using the ingredients below:

| Ingredient | Quantity (mg/tablet) |
|---|---|
| COMPOUND No. 1 | 10 |
| Cellulose, microcrystalline | 200 |
| Silicon dioxide, fumed | 10 |
| Stearic acid | 10 |
| Total | 230 |

The components are blended and compressed to form tablets each weighing 230 mg.

The active ingredients may be separately premixed with the other non-active ingredients, before being mixed to form a formulation. The active ingredients may also be mixed with each other, before being mixed with the non-active ingredients to form a formulation.

Soft gelatin capsules may be prepared with capsules containing a mixture of the active ingredients of the invention, vegetable oil, fat, or other suitable vehicle for soft gelatin capsules. Hard gelatin capsules may contain granules of the active ingredients. Hard gelatin capsules may also contain the active ingredients together with solid powdered ingredients such as lactose, saccharose, sorbitol, mannitol, potato starch, corn starch, amylopectin, cellulose derivatives or gelatin.

Dosage units for rectal administration may be prepared (i) in the form of suppositories that contain the active substance mixed with a neutral fat base; (ii) in the form of a gelatin rectal capsule that contains the active substance in a mixture with a vegetable oil, paraffin oil or other suitable vehicle for gelatin rectal capsules; (iii) in the form of a ready-made micro enema; or (iv) in the form of a dry micro enema formulation to be reconstituted in a suitable solvent just prior to administration.

Liquid preparations may be prepared in the form of syrups, elixirs, concentrated drops or suspensions, e.g. solutions or suspensions containing the active ingredients and the remainder consisting, for example, of sugar or sugar alcohols and a mixture of ethanol, water, glycerol, propylene glycol and polyethylene glycol. If desired, such liquid preparations may contain coloring agents, flavoring agents, preservatives, saccharine and carboxymethyl cellulose or other thickening agents. Liquid preparations may also be prepared in the form of a dry powder, reconstituted with a suitable solvent prior to use. Solutions for parenteral administration may be prepared as a solution of a formulation of the invention in a pharmaceutically acceptable solvent. These solutions may also contain stabilizing ingredients, preservatives and/or buffering ingredients. Solutions for parenteral administration may also be prepared as a dry preparation, reconstituted with a suitable solvent before use.

Also provided according to the present invention are formulations and 'kits of parts' comprising one or more containers filled with one or more of the ingredients of a pharmaceutical composition of the invention, for use in medical therapy. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration. The use of formulations of the invention in the manufacture of medicaments for use in the treatment of a condition in which activation of cannabinoid $CB_1$ receptors is required or desired, and methods of medical treatment or comprising the administration of a therapeutically effective total amount of at least one compound of formula (I), to a patient suffering from, or susceptible to, a condition in which activation of cannabinoid $CB_1$ receptors is required or desired.

By way of example and not of limitation, several pharmaceutical compositions are given, comprising exemplary active compounds for systemic use or topical application. Other compounds of the invention or combinations thereof, may be used in place of (or in addition to) said compounds. The concentration of the active ingredient may be varied over a wide range as discussed herein. Amounts and types of ingredients that may be included are known in the art.

Bibliography

To the extent in which the following references are useful to one skilled in the art, or to more fully describe this invention, they are incorporated herein by reference. Neither these, nor any other documents or quotes cited herein, nor citations to any references, are admitted to be prior art documents or citations.

Akaji, K. et al., *Tetrahedron Lett.*, 35, 3315-3318, 1994.
Albericio, F., et al., *Tetrahedron Lett.*, 38, 4853-4856, 1997.
Annan et al., J. Am. Chem. Soc. 1989, 111, 8895-8901
Bach et al., Tetrahedron, 1994, 50, 7543-7556
Barnes, M. P., Expert Opin. Pharmacother. 2006, 7, 607-615)
Berge, S. M.: "*Pharmaceutical salts*", J. Pharmaceutical Science, 66, 1-19 (1977).
Bickel, M. H., "*The pharmacology and Biochemistry of N-oxides*", *Pharmacological Reviews*, 21(4), 325-355, 1969.
Bodanszky, M. and A. Bodanszky: *The Practice of Peptide Synthesis*, Springer-Verlag, New York, ISBN: 0-387-57505-7, 1994.
Byrn et al., Pharmaceutical Research, 12(7), 945-954, 1995.
Chem. Ber. 1965, 98, 1588-1597
Cheng, Y. and Prusoff, W. H., *Biochem. Pharmacol.*, 22, 3099-3108, 1973
Croxford, J. L., "*Therapeutic potential of cannabinoids in CNS disease*", *CNS Drugs*, 17, 179-202, 2003.
Croxford, J. L. and Miller, S. D. "Towards cannabis and cannabinoid treatment of multiple sclerosis", *Drugs Today (Barc)*, 40, 663-676, 2004.
Drysdale, A. J. and Platt, B., "*Cannabinoids: mechanisms and therapeutic applications in the CNS*", Curr. Med. Chem., 10, 2719-2732, 2003
Dwyer & Meilor,: "*Chelating agents and Metal Chelate*", Academic Press, chapter 7, 1964.
Huffman et al., Curr. Med. Chem., 6, 705-720, 1999[a]
Huffman et al., Bioorg. Med. Chem., 7, 2905-2914, 1999[b]
Hurst, D. P. et al., Mol. Pharmacol., 62, 1274-1287, 2002
Lange, J. H. M. and Kruse, C. G. *Drug Discov. Today*, 10, 693-702, 2005

Levin, J. I., Turos, E. and Weinreb, S. M., *Synth Commun.*, 12, 989-993, 1982

Ligresti, A., et al., *"Possible endocannabinoid control of colorectal cancer growth"*, Gastro-enterology, 125, 677-687, 2003.

Martin, E. W. (Editor), *"Remington: The Science and Practice of Pharmacy"*, Mack Publishing Company, 19th Edition, Easton, Pa., Vol 2., Chapter 83, 1447-1462, 1995.

Montalbetti, C. A. G. N. & V. Falque, *Tetrahedron*, 61, 10827-52. 2005.

Pertwee, R. G., Life Sci., 76, 1307-1324, 2005

Reggio, P. H., Curr. Pharm. Des., 9, 1607-1633, 2003

Rinaldi-Carmona et al., J. Pharmacol. Exp. Ther., 284, 644-650, 1998

Shim, J., et al., J. Med. Chem., 45, 1447-1459, 2002.

Smith, M. B. and March, J., *"Advanced organic chemistry, reactions, mechanisms and structure"*, fifth edition, John Wiley & Sons, Inc., New York, 2001, p. 275.

Smith, P. F., *"Medicinal cannabis extracts for the treatment of multiple sclerosis"*, Curr. Opin. Investig. Drugs, 5, 727-730, 2004

WO 2005/074920, WO 2005/077911 and WO 2007/009689

What is claimed is:

1. A compound of formula (I)

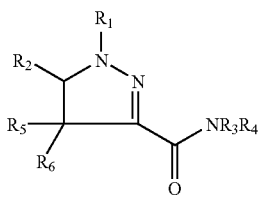

or a tautomer, stereoisomer, N-oxide, or a pharmacologically acceptable salt of any of the foregoing,
wherein:
$R_1$ is chosen from:
$C_{3-10}$ linear alkyl, $C_{4-10}$ branched alkyl, $C_{4-10}$ alkenyl, $C_{4-10}$ alkynyl, $C_{3-10}$-heteroalkyl, $C_{5-8}$-cycloalkyl-$C_{1-5}$-alkyl, and $C_{5-8}$-heterocycloalkyl-$C_{1-5}$-alkyl, each of which may be optionally substituted with 1-5 substituents, wherein the substituents are the same or different, and are chosen from methyl, ethyl, hydroxy, amino, cyano and fluoro,
aryl-$C_{1-3}$-alkyl, heteroaryl-$C_{1-3}$-alkyl, aryl-$C_{1-3}$-heteroalkyl, and heteroaryl-$C_{1-3}$-heteroalkyl, wherein the aryl or heteroaryl groups are optionally substituted with 1-5 substituents Y, wherein each Y is the same or different, and is chosen from $C_{1-3}$-alkyl, $C_{1-3}$-alkoxy, hydroxy, halogen, trifluoromethyl, trifluoromethylthio, trifluoromethoxy, nitro, amino, mono- or dialkyl($C_{1-2}$)-amino, mono- or dialkyl($C_{1-2}$)-amido, ($C_{1-3}$)-alkyl sulfonyl, dimethylsulfamido, $C_{1-3}$-alkoxycarbonyl, carboxyl, trifluoromethylsulfonyl, cyano, carbamoyl, sulfamoyl, phenyl, and acetyl, and
2-cyano-ethyl;
$R_2$ is chosen from aryl and heteroaryl, each of which may be optionally substituted with 1-5 substituents Y as defined above;
$R_3$ is chosen from:
linear and branched $C_{3-10}$ alkyl, $C_{3-8}$ cycloalkyl, $C_{5-10}$ bicycloalkyl, $C_{6-10}$ tricycloalkyl and $C_{8-11}$ tetracycloalkyl, each of which may be optionally substituted with 1-5 substituents, wherein the substituents are the same or different, and are chosen from methyl, ethyl, hydroxy, amino, and fluoro,
$C_{3-8}$ cycloalkyl substituted with aryl and heteroaryl, wherein the aryl and heteroaryl are optionally substituted with 1-5 substituents Y as defined above,
2,2,2-trifluoroethyl and 2-fluoroethyl,
$C_{5-8}$ heterocycloalkyl, $C_{6-10}$ bicycloheteroalkyl, and $C_{7-10}$ tricycloheteroalkyl, each of which may be optionally substituted with 1-5 substituents, wherein the substituents are the same or different, and are chosen from methyl, ethyl, hydroxy, amino, and fluoro,
$C_{3-8}$ cycloalkyl-$C_{1-3}$-alkyl, $C_{5-10}$-bicycloalkyl-$C_{1-3}$-alkyl, and $C_{6-10}$-tricycloalkyl-$C_{1-3}$-alkyl, each of which may be optionally substituted with 1-5 substituents, wherein the substituents are the same or different, and are chosen from methyl, ethyl, hydroxy, amino, and fluoro,
branched and linear $C_{3-8}$ heterocycloalkyl-$C_{1-3}$-alkyl, $C_{5-10}$ bicycloheteroalkyl-$C_{1-3}$-alkyl, and $C_{6-10}$ tricycloheteroalkyl-$C_{1-3}$-alkyl, each of which may be optionally substituted with 1-5 substituents, wherein the substituents are the same or different, and are chosen from methyl, ethyl, hydroxy, amino, and fluoro,
aryl and heteroaryl, each of which may be optionally substituted with 1-5 substituents Y as defined above,
aryl-$C_{1-5}$-alkyl, heteroaryl-$C_{1-5}$-alkyl, and diaryl-$C_{1-5}$-alkyl, wherein the aryl or heteroaryl groups are optionally substituted with 1-5 substituents Y as defined above,
linear and branched $C_{4-8}$ alkenyl and $C_{4-8}$ alkynyl, each of which may be optionally substituted with 1-3 fluorine atoms, and
branched and linear $C_{2-10}$ heteroalkyl, comprising 1-2 heteroatoms chosen from N, O, or S;
$R_4$ is chosen from hydrogen and $C_{1-4}$ alkyl;
$R_5$ is chosen from hydrogen and $C_{1-2}$ alkyl, optionally substituted with 1-3 fluorine atoms; and
$R_6$ is chosen from hydrogen and $C_{1-2}$ alkyl, optionally substituted with 1-3 fluorine atoms.

2. A compound according to claim 1, or a tautomer, stereoisomer, N-oxide, or a pharmacologically acceptable salt of any of the foregoing, wherein:
$R_1$ is chosen from:
$C_{3-10}$ linear alkyl, $C_{4-10}$ branched alkyl, and $C_{5-8}$-cycloalkyl-$C_{1-5}$-alkyl, each of which may be optionally substituted with 1-3 substituents, wherein the substituents are the same or different, and are chosen from methyl, ethyl, cyano, and fluoro;
aryl-$C_{1-3}$-alkyl, wherein the aryl group is optionally substituted with 1-3 substituents Y, wherein each Y is the same or different, and is chosen from $C_{1-3}$-alkyl, $C_{1-3}$-alkoxy, halogen, trifluoromethyl, trifluoro-methoxy, nitro, cyano, and phenyl, and
2-cyano-ethyl;
$R_2$ is chosen from phenyl, thienyl, benzothienyl, and pyridyl, each of which may be optionally substituted with 1 or 2 substituents, wherein the substituents are the same or different, and are chosen from halogen, methyl, $CF_3$, $OCH_3$, and $OCF_3$;
$R_3$ is chosen from:
linear and branched $C_{3-10}$ alkyl, $C_{3-8}$ cycloalkyl, $C_{5-10}$ bicycloalkyl, and $C_{6-10}$ tricycloalkyl, each of which may be optionally substituted with 1-3 substituents, wherein the substituents are the same or different, and are chosen from methyl, ethyl, hydroxy, amino, fluoro, and aryl, $C_{5-8}$ heterocycloalkyl optionally substituted with 1-5 substituents, wherein the substituents are the same or different, and are chosen from methyl, ethyl, and fluoro, $C_{3-8}$ cycloalkyl-$C_{1-3}$-alkyl, $C_{5-10}$-bicycloalkyl-$C_{1-3}$-alkyl, and $C_{6-10}$-tricycloalkyl-$C_{1-3}$-alkyl, each of which may be optionally substituted with 1-5 substituents, wherein the substituents are the same or different, and are chosen from methyl, ethyl, and fluoro, aryl and heteroaryl, each of which may be optionally substituted with 1-5 substituents Y, wherein each Y is the same or different, and is chosen from $C_{1-3}$-alkyl, $C_{1-3}$-alkoxy, halogen, trifluoromethyl, trifluoromethylthio, trifluoromethoxy, nitro, cyano, and phenyl, aryl-$C_{1-5}$-alkyl, heteroaryl-$C_{1-5}$-alkyl, and diaryl-$C_{1-5}$-alkyl, wherein the aryl and heteroaryl groups are optionally substituted with 1-5 substituents, wherein the substituents are the same or different, and are chosen from $C_{1-3}$-alkyl, $C_{1-3}$-alkoxy, halogen, trifluoromethyl, trifluoromethylthio, trifluoromethoxy, nitro, cyano, and phenyl, and branched and linear $C_{2-10}$ heteroalkyl, comprising 1-2 heteroatoms chosen from N, O, and S; and $R_4$, $R_5$, and $R_6$ are as defined in claim 1.

3. A compound according to claim 2, or a tautomer, stereoisomer, N-oxide, or a pharmacologically acceptable salt of any of the foregoing,
wherein:
$R_1$ is chosen from:
$C_{3-8}$ linear alkyl, $C_{4-8}$ branched alkyl, and $C_{5-6}$-cycloalkyl-$C_{1-5}$-alkyl, each of which may be optionally substituted with 1-3 substituents, wherein the substituents are the same or different, and are chosen from cyano and fluoro; and
aryl-$C_{1-3}$-alkyl and 2-cyano-ethyl;
$R_2$ is chosen from phenyl, thienyl, benzothienyl, and pyridyl, each of which may be optionally substituted with halogen, methyl, $CF_3$, $OCH_3$, and $OCF_3$; and
$R_3$, $R_4$, $R_5$, and $R_6$ have the meanings as defined in claim 2.

4. A compound according to claim 3, or a tautomer, stereoisomer, N-oxide, or a pharmacologically acceptable salt of any of the foregoing,
wherein:
$R_1$ is chosen from 2-cyano-ethyl, n-propyl, n-butyl, 4,4,4-trifluorobutyl, isobutyl, n-pentyl, cyclohexylmethyl, and phenethyl;
$R_2$ is chosen from 2-fluorophenyl, 3-(trifluoromethyl)phenyl, 3-chlorophenyl, 3-fluorophenyl, 3-methoxyphenyl, 4-chlorophenyl, 4-fluorophenyl, benzothien-3-yl, pyrid-2-yl, thien-3-yl, and phenyl;
$R_3$ is chosen from 3-(trifluoromethyl)benzyl, 3-(trifluoromethyl)benzyl, 1-(4-fluorophenyl)-1-methyl-ethyl, 1-phenyl-1-methyl-ethyl, 1-phenyl-ethyl, 2-indanyl, 2-(4-fluorophenyl)-1,1-dimethyl-ethyl, 2-(trifluoromethyl)benzyl, 2,2-dimethylpropyl, 2,2-diphenylethyl, 2,2-diphenylpropyl, 2-methoxybenzyl, 2-phenyl-propyl, 2-phenyl-trans-cyclopropyl, 2-trifluoromethyl)phenyl, 3,4,5-trimethoxybenzyl, 3,4-dimethoxybenzyl, 3-fluorobenzyl, 3-methoxybenzyl, 4-chlorobenzyl, 4-methoxybenzyl, 5-methyl-thiazol-2-yl, adamant-1-yl, adamant-2-yl, adamantylmethyl, benzyl, cycloheptyl, cyclohexylmethyl, cyclooctyl, endo-bicyclo[2.2.1]hept-2-yl, exo-bicyclo[2.2.1]hept-2-yl, indan-2-yl, N,2, 2,6,6-pentamethylpiperidin-4-yl, naphth-1-yl, naphthalen-1-yl-methyl, noradamant-1-yl, pyridin-3-ylmethyl, quinolin-3-yl, tert-butyl, (1-ethyl)propyl, (1R,2S,5R)-rel-6,6-dimethylbicyclo[3.1.1.]heptan-2-methyl, (3-dimethylamino)-2,2-dimethylpropyl, (furan-2-yl)methyl, (pyridin-3-yl)-methyl, 1-(4-fluorophenyl)-1-methyl-ethyl, 1-(adamant-1-yl)-ethyl, 1-phenyl-1-methyl-ethyl, 2-(4-fluorophenyl)ethyl, 2-(7-methyl-indol-3-yl)ethyl, 2-(indol-3-yl)ethyl, 2-(thien-2-yl)ethyl, 3-(trifluoromethyl)benzyl, 3,3-diphenylpropyl, 3,4-difluorobenzyl, 4-(trifluoromethyl)benzyl, endo-(1R,2S,4R)-1,7,7-trimethylbicyclo[2.2.1]hept-2-yl, naphthalen-1-yl-methyl, benzyl, cyclohexylmethyl, cyclopentyl, methyl-N-(Naphthalen-1-yl-methyl), and phenyl;
$R_4$ is chosen from hydrogen and methyl;
$R_5$ is chosen from hydrogen and methyl; and
$R_6$ is hydrogen.

5. A compound according to claim 1, or a tautomer, stereoisomer, N-oxide, or a pharmacologically acceptable salt of any of the foregoing, wherein said compound is an optically active enantiomer.

6. A medicament, comprising a compound according to claim 1, or a pharmacologically acceptable salt thereof.

7. A pharmaceutical composition comprising, a compound of claim 1, or a pharmaceutically acceptable salt thereof, and at least one pharmaceutically acceptable carrier and/or at least one pharmaceutically acceptable auxiliary substance.

8. A pharmaceutical composition according to claim 7, for the treatment of multiple sclerosis, traumatic brain injury, pain, appetite disorders, epilepsy, Alzheimer's disease, Tourette's syndrome, cerebral ischaemia or gastrointestinal disorders.

9. A pharmaceutical composition according to claim 7, further comprising at least one additional therapeutic agent.

10. A method of treating at least one disorder or condition mediated by cannabinoid receptors in a mammal, comprising administering to said mammal, a therapeutically acceptable amount of a compound of formula (I), or a pharmaceutically acceptable salt thereof, wherein the disorder or condition is chosen from multiple sclerosis, traumatic brain injury, pain including chronic pain, neuropathic pain, acute pain and inflammatory pain, osteoporosis, appetite disorders, epilepsy, Alzheimer's disease, Tourette's syndrome, cerebral ischaemia and gastrointestinal disorders.

11. A compound of formula (X):

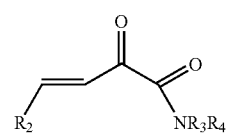

wherein:
$R_2$ is chosen from aryl and heteroaryl, each of which may be optionally substituted with 1-5 substituents Y as defined above;
$R_3$ is hydrogen;
$R_4$ is chosen from:
$C_{6-10}$ bicycloalkyl and $C_{7-10}$ tricycloalkyl, each of which may be optionally substituted with 1-5 substituents, wherein the substituents are the same or different, and are chosen from methyl, ethyl, hydroxyl, amino, and fluoro; and 2-phenyl-1,1-dimethyl-ethyl, and 1-phenyl-1-methyl-ethyl, wherein the phenyl groups are optionally substituted with 1-5 substituents Y, wherein each Y is the same or different, and is chosen from $C_{1-3}$-alkyl, $C_{1-3}$-alkoxy, hydroxy, halogen, trifluoromethyl, trifluoromethylthio, trifluoromethoxy, nitro, amino, mono- or dialkyl($C_{1-2}$)-amino, mono- or dialkyl($C_{1-2}$)-amido, ($C_{1-3}$)-alkyl sulfonyl, dimethylsulfamido, $C_{1-3}$-alkoxycarbonyl, carboxyl, trifluoromethylsulfonyl, cyano, carbamoyl, sulfamoyl, phenyl, and acetyl.

* * * * *